United States Patent
Qin et al.

(10) Patent No.: US 11,981,740 B2
(45) Date of Patent: *May 14, 2024

(54) BAFF-R ANTIBODIES AND USES THEREOF

(71) Applicants: CITY OF HOPE, Duarte, CA (US);
BOARD OF REGENTS, THE UNIVERSITY OF TEXAS SYSTEM, Austin, TX (US)

(72) Inventors: Hong Qin, Duarte, CA (US); Larry W. Kwak, Duarte, CA (US); Jingxing Li, Duarte, CA (US); Kexin Huang, Duarte, CA (US)

(73) Assignees: CITY OF HOPE, Duarte, CA (US); BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 408 days.

This patent is subject to a terminal disclaimer.

(21) Appl. No.: 17/403,698

(22) Filed: Aug. 16, 2021

(65) Prior Publication Data
US 2022/0041743 A1 Feb. 10, 2022

Related U.S. Application Data

(63) Continuation of application No. 16/307,434, filed as application No. PCT/US2017/036181 on Jun. 6, 2017, now Pat. No. 11,136,405.

(60) Provisional application No. 62/346,324, filed on Jun. 6, 2016.

(51) Int. Cl.
| | | |
|---|---|---|
| C07K 16/28 | (2006.01) | |
| A61P 35/00 | (2006.01) | |
| C07K 16/30 | (2006.01) | |
| A61K 39/00 | (2006.01) | |

(52) U.S. Cl.
CPC .......... C07K 16/2878 (2013.01); A61P 35/00 (2018.01); C07K 16/3061 (2013.01); *A61K 2039/505* (2013.01); *C07K 2317/24* (2013.01); *C07K 2317/622* (2013.01); *C07K 2317/732* (2013.01); *C07K 2317/77* (2013.01); *C07K 2319/02* (2013.01); *C07K 2319/03* (2013.01); *C07K 2319/33* (2013.01)

(58) Field of Classification Search
CPC ............ C07K 16/2878; C07K 16/3061; C07K 2317/24; C07K 2317/622; C07K 2317/732; C07K 2317/77; C07K 2319/02; C07K 2319/03; C07K 2319/33; C07K 14/7051; A61P 35/00; A61P 7/06; A61K 2039/505; A61K 2039/5158; A61K 39/0011

See application file for complete search history.

(56) References Cited

U.S. PATENT DOCUMENTS

| | | |
|---|---|---|
| 2002/0165156 A1 | 11/2002 | Browning et al. |
| 2015/0118240 A1 | 4/2015 | Finney et al. |
| 2018/0181888 A1 | 6/2018 | Ihara et al. |

FOREIGN PATENT DOCUMENTS

| | | | |
|---|---|---|---|
| CN | 1083389 A | 3/1994 | |
| CN | 101120021 A | 2/2008 | |
| CN | 104364265 A | 2/2015 | |
| CN | 105143263 A | 12/2015 | |
| CN | 113307868 A | 8/2021 | |
| JP | 2008526205 A | 7/2008 | |
| JP | 2015525204 A | 9/2015 | |
| WO | 2006073941 A2 | 7/2006 | |
| WO | 2011119901 A1 | 9/2011 | |
| WO | WO 2010/007082 * | 1/2012 | ............. C07K 16/28 |
| WO | 2013013013 A2 | 1/2013 | |
| WO | 2016009030 A2 | 1/2016 | |
| WO | 2016061142 A1 | 4/2016 | |
| WO | 2017189959 A1 | 11/2017 | |
| WO | 2017214170 A2 | 12/2017 | |
| WO | 2017214170 A3 | 12/2017 | |

OTHER PUBLICATIONS

CN201780034709.5, "Notice of Decision to Grant", dated Jul. 4, 2022, 2 pages.
JP2019-516100, "Notice of Decision to Grant", dated Apr. 4, 2023, 5 pages.
JP2022-017156, "Office Action", dated Aug. 8, 2023, 8 pages.
CN201780034709.5 , "Office Action" with Machine translation, dated Nov. 23, 2021, 15 pages.
Wu et al., "The Expression Research of B Lymphocyte Subsets, B-cell Activating Factor and its Receptor BR3 in Peripheral Blood from Patients with Ankylosing Spondylitis", Laboratory Medicine, vol. 26, No. 12, Dec. 2011, pp. 818-822.
U.S. Appl. No. 16/307,434, "Non-Final Office Action", dated Feb. 8, 2021, 7 pages.
U.S. Appl. No. 16/307,434, "Notice of Allowance", dated May 20, 2021, 8 pages.
Adam et al., "B-Cell Maturation Antigen (BCMA)-Specific Chimeric Antigen Receptor T Cells (CART-BCMA) for Multiple Myeloma (MM): Initial Safety and Efficacy from a Phase I Study : Blood Journal", Blood, Jan. 1, 2016, 6 pages.

(Continued)

*Primary Examiner* — Nelson B Moseley, II
(74) *Attorney, Agent, or Firm* — Kilpatrick Townsend & Stockton LLP

(57) ABSTRACT

Provided herein are BAFF-R antibodies as well as compositions and methods of making and using the same. The antibodies provided herein are, inter alia, useful for the treatment of cancer and autoimmune diseases.

20 Claims, 45 Drawing Sheets

Specification includes a Sequence Listing.

(56) References Cited

OTHER PUBLICATIONS

Ali et al., "T Cells Expressing an Anti-b-cell Maturation Antigen Chimeric Antigen Receptor Cause Remissions of Multiple Myeloma", Blood, vol. 128, No. 13, Jul. 13, 2016, pp. 1688-1700.
Davila et al., "Biology and Clinical Application of CAR T Cells for B Cell Malignancies", International Journal of Hematology, vol. 104, No. 1, Jun. 4, 2016, pp. 6-17.
Eisenberg, "Combination Biologics: 1 Stone, 2 Birds", Blood, vol. 110, No. 12, Dec. 1, 2007, p. 3817.
Guan et al., "B Cell-Activating Factor Belonging to the Tnf Family (Baff)-r Is the Principal Baff Receptor Facilitating BAFF Costimulation of Circulating T and B Cells", The Journal of Immunology, the American Association of Immunologists, US, vol. 173, No. 2, Jul. 15, 2004, pp. 807-817.
JP2019-516100, "Office Action", dated Feb. 24, 2021, 12 pages.
Parameswaran et al., "Effector-Mediated Eradication of Precursor B Acute Lymphoblastic Leukemia with a Novel Fc-Engineered Monoclonal Antibody Targeting the BAFF-R", Molecular Cancer Therapeutics, vol. 13, No. 6, May 13, 2014, pp. 1567-1577.
PCT/US2017/036181, "International Preliminary Report on Patentability", dated Dec. 20, 2018, 11 pages.
PCT/US2017/036181, "International Search Report and Written Opinion", dated Dec. 1, 2017, 19 pages.
PCT/US2017/036181, "Invitation to Pay Add'l Fees and Partial Search Report", dated Oct. 4, 2017, 13 pages.
Syed et al., "Remissions of Multiple Myeloma During a First-in-Humans Clinical Trial of T Cells Expressing an Anti-B-Cell Maturation Antigen Chimeric Antigen Receptor:Blood Journal", Blood, URL:http://www.bloodjournal.org/content/126/23/LBA-1?sso-checked=true&utm_source=TrendMD&utm_medium=cpc&utm_campaign=Blood_TrendMD_0, Jan. 1, 2015, 5 pages.
EP17739364.2, "Office Action", dated Feb. 23, 2022, 7 pages.
Lin et al., "Anti-BR3 Antibodies: A New Class of B-cell Immunotherapy Combining Cellular Depletion and Survival Blockade", Blood, vol. 110, No. 12, Dec. 1, 2007, pp. 3959-3967.
Mcwilliams et al., "Anti-BAFF-R Antibody VAY-736 Demonstrates Promising Preclinical Activity in CLL and Enhances Effectiveness of Ibrutinib", Blood Advances, vol. 3, No. 3, Feb. 12, 2019, pp. 447-460.
Qin et al., "Novel BAFF-Receptor Antibody to Natively Folded Recombinant Protein Eliminates Drug Resistant Human B-cell Malignancies In Vivo", Clinical Cancer Research, vol. 24, No. 5, Mar. 1, 2018, pp. 1114-1123.
JP2019-516100, "Office Action" with English translation, dated Oct. 5, 2021, 4 pages.
CN201780034709.5, "Office Action", dated Mar. 30, 2022, 6 pages.
Kim et al., "B-Cell-Activating Factor is a Regulator of Adipokines and a Possible Mediator Between Adipocytes and Macrophages", Experimental & Molecular Medicine, vol. 45, 2013, 8 pages.
Zhou et al., "BAFF Level in Bone Marrow and Expression of BAFF Receptor on BCells in Multiple Myeloma Patients", Journal of Experimental Hematology, vol. 20, No. 5, 2012, pp. 1131-1134.
JP2022-017156, "Office Action", dated Jan. 4, 2023, 2 pages.
JP2022-017156, "Notice of Allowance" with machine translation, Jan. 30, 2024, 4 pages.

* cited by examiner

Hybridoma clones screened by ELISA for antibody production

| Clone | (h)BAFF-R-expressing cells (OD 450 nm) | Parental L cell (OD 450 nm) |
|---|---|---|
| C53 | 0.552 | 0.095 |
| C55 | 1.067 | 0.102 |
| C67 | 0.615 | 0.093 |
| C90 | 0.645 | 0.116 |
| C39 | 0.137 | 0.091 |

FIG. 7B

SEQUENCE LISTING

```
<160> NUMBER OF SEQ ID NOS: 32

<210> SEQ ID NO 1
<211> LENGTH: 10
<212> TYPE: PRT
<213> ORGANISM: mus musculus

<400> SEQUENCE: 1

Glu Ser Val Asp Asn Tyr Gly Ile Ser Phe
1               5                   10

<210> SEQ ID NO 2
<211> LENGTH: 3
<212> TYPE: PRT
<213> ORGANISM: mus musculus

<400> SEQUENCE: 2

Ala Ala Ser
```

-continued

```
<210> SEQ ID NO 3
<211> LENGTH: 9
<212> TYPE: PRT
<213> ORGANISM: mus musculus

<400> SEQUENCE: 3

Gln Gln Ser Lys Glu Val Pro Trp Thr
1               5

<210> SEQ ID NO 4
<211> LENGTH: 8
<212> TYPE: PRT
<213> ORGANISM: mus musculus

<400> SEQUENCE: 4

Gly Asp Ser Ile Thr Ser Gly Tyr
1               5

<210> SEQ ID NO 5
<211> LENGTH: 7
<212> TYPE: PRT
<213> ORGANISM: mus muculus

<400> SEQUENCE: 5

Ile Ser Tyr Ser Gly Ser Thr
1               5

<210> SEQ ID NO 6
<211> LENGTH: 12
<212> TYPE: PRT
<213> ORGANISM: mus muculus

<400> SEQUENCE: 6

Ala Ser Pro Asn Tyr Pro Phe Tyr Ala Met Asp Tyr
1               5                   10

<210> SEQ ID NO 7
<211> LENGTH: 6
<212> TYPE: PRT
<213> ORGANISM: mus musculus

<400> SEQUENCE: 7

Gln Asp Ile Ser Asn Tyr
1               5

<210> SEQ ID NO 8
<211> LENGTH: 3
<212> TYPE: PRT
<213> ORGANISM: mus muculus

<400> SEQUENCE: 8

Tyr Thr Ser
1

<210> SEQ ID NO 9
<211> LENGTH: 7
<212> TYPE: PRT
<213> ORGANISM: mus muculus

<400> SEQUENCE: 9

Phe Ser Glu Leu Pro Trp Thr
1               5
```

<210> SEQ ID NO 10
<211> LENGTH: 10
<212> TYPE: PRT
<213> ORGANISM: mus muculus

<400> SEQUENCE: 10

Gly Phe Ser Leu Ser Thr Ser Gly Met Gly
1               5                   10

<210> SEQ ID NO 11
<211> LENGTH: 7
<212> TYPE: PRT
<213> ORGANISM: mus muculus

<400> SEQUENCE: 11

Ile Trp Trp Asp Asp Asp Lys
1               5

<210> SEQ ID NO 12
<211> LENGTH: 10
<212> TYPE: PRT
<213> ORGANISM: mus muculus

<400> SEQUENCE: 12

Ala Arg Ser Phe Gly Tyr Gly Leu Asp Tyr
1               5                   10

<210> SEQ ID NO 13
<211> LENGTH: 411
<212> TYPE: DNA
<213> ORGANISM: artificial sequence
<220> FEATURE:
<223> OTHER INFORMATION: synthetic construct

<400> SEQUENCE: 13
atgtacagga tgcaactcct gtcttgcatt gcactaagtc ttgcacttgt cacgaattca      60
gacattgtgc tgacccaatc tccagcttct ttggctgtgt ctctagggca gagggccacc     120
atctcctgca gagccagcga aagtgttgat aattatggca ttagttttat gaactggttc     180
caacagaaac caggacagcc acccaaactc ctcatctatg ctgcatccaa ccaaggatcc     240
ggggtccctg ccaggtttag tggcagtggg tctgggacag acttcagcct caacatccat     300
cctatggagg aggatgatac tgcaatgtat ttctgtcagc aaagtaagga ggttccgtgg     360
acgttcggtg gaggcaccaa gctggaaatc aaaaccatgg aaatcaaacg t              411

<210> SEQ ID NO 14
<211> LENGTH: 137
<212> TYPE: PRT
<213> ORGANISM: artificial sequence
<220> FEATURE:
<223> OTHER INFORMATION: synthetic construct

<400> SEQUENCE: 14

Met Tyr Arg Met Gln Leu Leu Ser Cys Ile Ala Leu Ser Leu Ala Leu
1               5                   10                  15

Val Thr Asn Ser Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Asn Tyr Gly Ile Ser Phe Met Asn Trp Phe Gln Gln Lys Pro
    50                  55                  60

```
Gly Gln Pro Pro Lys Leu Leu Ile Tyr Ala Ala Ser Asn Gln Gly Ser
 65                  70                  75                  80

Gly Val Pro Ala Arg Phe Ser Gly Ser Gly Ser Gly Thr Asp Phe Ser
                 85                  90                  95

Leu Asn Ile His Pro Met Glu Glu Asp Asp Thr Ala Met Tyr Phe Cys
            100                 105                 110

Gln Gln Ser Lys Glu Val Pro Trp Thr Phe Gly Gly Gly Thr Lys Leu
        115                 120                 125

Glu Ile Lys Thr Met Glu Ile Lys Arg
    130                 135
```

```
<210> SEQ ID NO 15
<211> LENGTH: 420
<212> TYPE: DNA
<213> ORGANISM: artificial sequence
<220> FEATURE:
<223> OTHER INFORMATION: synthetic construct

<400> SEQUENCE: 15
atgtacagga tgcaactcct gtcttgcatt gcactaagtc ttgcacttgt cacgaattcg      60
gaggtgcagc tgcaggagtc tggacctagc ctcgtgaaac cttctcagac tctgtccctc     120
acctgttctg tcactggcga ctccatcacc agtggttact ggaactggat ccggaaattc     180
ccagggaata acttgagta catggggtac ataagctaca gtggtagcac ttactacaat     240
ccatctctca aaagtcgaat ctccatcact cgagacacat ccaagaacca gtactacctg     300
cagttaaatt ctgtgacacc tgaggacaca gccacatatt actgtgcaag ccccaattac     360
cccttctatg ctatggacta ctggggtcaa ggaacctcag tcaccgtctc ctcagatatc     420
```

```
<210> SEQ ID NO 16
<211> LENGTH: 140
<212> TYPE: PRT
<213> ORGANISM: artificial sequence
<220> FEATURE:
<223> OTHER INFORMATION: synthetic construct

<400> SEQUENCE: 16

Met Tyr Arg Met Gln Leu Leu Ser Cys Ile Ala Leu Ser Leu Ala Leu
 1               5                  10                  15

Val Thr Asn Ser Glu Val Gln Leu Gln Glu Ser Gly Pro Ser Leu Val
            20                  25                  30

Lys Pro Ser Gln Thr Leu Ser Leu Thr Cys Ser Val Thr Gly Asp Ser
        35                  40                  45

Ile Thr Ser Gly Tyr Trp Asn Trp Ile Arg Lys Phe Pro Gly Asn Lys
    50                  55                  60

Leu Glu Tyr Met Gly Tyr Ile Ser Tyr Ser Gly Ser Thr Tyr Tyr Asn
 65                  70                  75                  80

Pro Ser Leu Lys Ser Arg Ile Ser Ile Thr Arg Asp Thr Ser Lys Asn
                 85                  90                  95

Gln Tyr Tyr Leu Gln Leu Asn Ser Val Thr Pro Glu Asp Thr Ala Thr
            100                 105                 110

Tyr Tyr Cys Ala Ser Pro Asn Tyr Pro Phe Tyr Ala Met Asp Tyr Trp
        115                 120                 125

Gly Gln Gly Thr Ser Val Thr Val Ser Ser Asp Ile
    130                 135                 140
```

```
<210> SEQ ID NO 17
<211> LENGTH: 403
```

```
<212> TYPE: DNA
<213> ORGANISM: artificial sequence
<220> FEATURE:
<223> OTHER INFORMATION: synthetic construct

<400> SEQUENCE: 17
atggagaccg acaccctgct gctctgggtg ctgctgctct gggtgcccgg ctccaccgga      60
gagatcgtgc tgacccagag ccctgccacc ctgtctctga gccctggcga gagagctacc     120
ctgtcctgca gagcctccga gtccgtggac aactacggca tctccttcct gaactggttc     180
cagcagaagc ccggccaggc ccccagactg ctgatctacg ccgcctctaa tcgggccacc     240
ggcatccctg ccagattctc cggatctggc tccggcaccg actttaccct gaccatctcc     300
agcctggaac ccgaggactt cgccgtgtac tactgccagc agtccaaaga ggtgccctgg     360
acctttggcg gaggcaccaa ggtggaaatc aagcggaccg tgg                       403

<210> SEQ ID NO 18
<211> LENGTH: 134
<212> TYPE: PRT
<213> ORGANISM: artificial sequence
<220> FEATURE:
<223> OTHER INFORMATION: synthetic construct

<400> SEQUENCE: 18

Met Glu Thr Asp Thr Leu Leu Leu Trp Val Leu Leu Leu Trp Val Pro
1               5                   10                  15

Gly Ser Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Ser
        35                  40                  45

Val Asp Asn Tyr Gly Ile Ser Phe Leu Asn Trp Phe Gln Gln Lys Pro
    50                  55                  60

Gly Gln Ala Pro Arg Leu Leu Ile Tyr Ala Ala Ser Asn Arg Ala Thr
65                  70                  75                  80

Gly Ile Pro Ala Arg Phe Ser Gly Ser Gly Ser Gly Thr Asp Phe Thr
                85                  90                  95

Leu Thr Ile Ser Ser Leu Glu Pro Glu Asp Phe Ala Val Tyr Tyr Cys
            100                 105                 110

Gln Gln Ser Lys Glu Val Pro Trp Thr Phe Gly Gly Gly Thr Lys Val
        115                 120                 125

Glu Ile Lys Arg Thr Val
    130

<210> SEQ ID NO 19
<211> LENGTH: 403
<212> TYPE: DNA
<213> ORGANISM: artificial sequence
<220> FEATURE:
<223> OTHER INFORMATION: synthetic construct

<400> SEQUENCE: 19
atggagaccg acaccctgct gctctgggtg ctgctgctct gggtgcccgg ctccaccgga      60
gacatcgtgc tgacccagag ccctgccacc ctgtctctga gccctggcga gagagctacc     120
ctgtcctgca gagcctccga gtccgtggac aactacggca tctccttcat gaactggttc     180
cagcagaagc ccggccaggc ccccagactg ctgatctacg ccgcctctaa tcgggccacc     240
ggcatccctg ccagattctc cggatctggc tccggcaccg actttaccct gaccatctcc     300
agcctggaac ccgaggactt cgccgtgtac tactgccagc agtccaaaga ggtgccctgg     360
```

```
acctttggcg gaggcaccaa ggtggaaatc aagcggaccg tgg            403
```

<210> SEQ ID NO 20
<211> LENGTH: 134
<212> TYPE: PRT
<213> ORGANISM: artificial sequence
<220> FEATURE:
<223> OTHER INFORMATION: synthetic construct

<400> SEQUENCE: 20

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Glu Ser
        35                  40                  45

Val Asp Asn Tyr Gly Ile Ser Phe Met Asn Trp Phe Gln Gln Lys Pro
    50                  55                  60

Gly Gln Ala Pro Arg Leu Leu Ile Tyr Ala Ala Ser Asn Arg Ala Thr
65                  70                  75                  80

Gly Ile Pro Ala Arg Phe Ser Gly Ser Gly Ser Gly Thr Asp Phe Thr
                85                  90                  95

Leu Thr Ile Ser Ser Leu Glu Pro Glu Asp Phe Ala Val Tyr Tyr Cys
            100                 105                 110

Gln Gln Ser Lys Glu Val Pro Trp Thr Phe Gly Gly Gly Thr Lys Val
        115                 120                 125

Glu Ile Lys Arg Thr Val
    130
```

<210> SEQ ID NO 21
<211> LENGTH: 403
<212> TYPE: DNA
<213> ORGANISM: artificial sequence
<220> FEATURE:
<223> OTHER INFORMATION: synthetic construct

<400> SEQUENCE: 21

```
atggagaccg acaccctgct gctctgggtg ctgctgctct gggtgcccgg ctccaccgga      60
gacatcgtga tgacccagag ccccctccagc ctgtctgcct ctgtgggcga cagagtgacc    120
atcacctgtc gggcctccga gtccgtggac aactacggca tctccttcat gaactggttc    180
cagcagaagc ccggcaaggc ccccaagctg ctgatctacg ccgcctctaa tctgggctct    240
ggcgtgccct ctagattctc cggatctggc tccggcaccg actttaccct gaccatctcc    300
agcctgcagc ccgaggactt cgccacctac tactgccagc agtccaaaga ggtgccctgg    360
acctttggcc agggcaccaa ggtggaaatc aagcggaccg tgg                      403
```

<210> SEQ ID NO 22
<211> LENGTH: 134
<212> TYPE: PRT
<213> ORGANISM: artificial sequence
<220> FEATURE:
<223> OTHER INFORMATION: synthetic construct

<400> SEQUENCE: 22

```
Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Ser Ser Leu Ser
            20                  25                  30
```

Ala Ser Val Gly Asp Arg Val Thr Ile Thr Cys Arg Ala Ser Glu Ser
            35                  40                  45

Val Asp Asn Tyr Gly Ile Ser Phe Met Asn Trp Phe Gln Gln Lys Pro
    50                  55                  60

Gly Lys Ala Pro Lys Leu Leu Ile Tyr Ala Ala Ser Asn Leu Gly Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
                100                 105                 110

Gln Gln Ser Lys Glu Val Pro Trp Thr Phe Gly Gln Gly Thr Lys Val
            115                 120                 125

Glu Ile Lys Arg Thr Val
            130

<210> SEQ ID NO 23
<211> LENGTH: 426
<212> TYPE: DNA
<213> ORGANISM: artificial sequence
<220> FEATURE:
<223> OTHER INFORMATION: synthetic construct

<400> SEQUENCE: 23
atggacccca agggcagcct gagctggaga atcctgctgt tcctgagcct ggccttcgag        60
ctgagctacg gccaggtgca gctgcaggaa tctggccctg gcctcgtgaa gccttcccag       120
accctgtccc tgacctgcac cgtgtccggc gactctatca cctccggcta ctggaactgg       180
atccggcagc atcctggcaa gggcctggag tatatcggct acatctccta ctccggctcc       240
acctactaca accccagcct gaagtccaga gtgaccatct cccgggacac ctccaagaac       300
cagttctccc tgaagctgtc ctccgtgacc gctgctgata ccgccgtgta ctactgcgcc       360 tccccccaact acccattcta cgccatggac tactggggcc agggcaccct cgtgaccgtg       420
tcctct                                                                  426

<210> SEQ ID NO 24
<211> LENGTH: 142
<212> TYPE: PRT
<213> ORGANISM: artificial sequence
<220> FEATURE:
<223> OTHER INFORMATION: synthetic construct

<400> SEQUENCE: 24

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Gln Thr Leu Ser Leu Thr Cys Thr Val
            35                  40                  45

Ser Gly Asp Ser Ile Thr Ser Gly Tyr Trp Asn Trp Ile Arg Gln His
    50                  55                  60

Pro Gly Lys Gly Leu Glu Tyr Ile Gly Tyr Ile Ser Tyr Ser Gly Ser
65                  70                  75                  80

Thr Tyr Tyr Asn Pro Ser Leu Lys Ser Arg Val Thr Ile Ser Arg Asp
                85                  90                  95

Thr Ser Lys Asn Gln Phe Ser Leu Lys Leu Ser Ser Val Thr Ala Ala
            100                 105                 110

```
Asp Thr Ala Val Tyr Tyr Cys Ala Ser Pro Asn Tyr Pro Phe Tyr Ala
            115                 120                 125

Met Asp Tyr Trp Gly Gln Gly Thr Leu Val Thr Val Ser Ser
    130                 135                 140

<210> SEQ ID NO 25
<211> LENGTH: 426
<212> TYPE: DNA
<213> ORGANISM: artificial sequence
<220> FEATURE:
<223> OTHER INFORMATION: synthetic construct

<400> SEQUENCE: 25
atggacccca agggcagcct gagctggaga atcctgctgt tcctgagcct ggccttcgag      60
ctgagctacg gcgaagtgca gctgcaggaa tctggccctg gcctcgtgaa gccttcccag     120
accctgtccc tgacctgcac cgtgtccggc gactctatca cctccggcta ctggaactgg     180
atccggcagc atcctggcaa gggcctggag tatatcggct acatctccta ctccggctcc     240
acctactaca accccagcct gaagtccaga gtgaccatct cccgggacac ctccaagaac     300
cagtactccc tgaagctgtc ctccgtgacc gctgctgata ccgccgtgta ctactgcgcc     360
tcccccaact acccctteta cgccatggac tactggggcc agggcaccct cgtgaccgtg     420
tcctct                                                                426

<210> SEQ ID NO 26
<211> LENGTH: 142
<212> TYPE: PRT
<213> ORGANISM: artificial sequence
<220> FEATURE:
<223> OTHER INFORMATION: synthetic construct

<400> SEQUENCE: 26

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Gln Glu Ser Gly
            20                  25                  30

Pro Gly Leu Val Lys Pro Ser Gln Thr Leu Ser Leu Thr Cys Thr Val
        35                  40                  45

Ser Gly Asp Ser Ile Thr Ser Gly Tyr Trp Asn Trp Ile Arg Gln His
    50                  55                  60

Pro Gly Lys Gly Leu Glu Tyr Ile Gly Tyr Ile Ser Tyr Ser Gly Ser
65                  70                  75                  80

Thr Tyr Tyr Asn Pro Ser Leu Lys Ser Arg Val Thr Ile Ser Arg Asp
                85                  90                  95

Thr Ser Lys Asn Gln Tyr Ser Leu Lys Leu Ser Ser Val Thr Ala Ala
            100                 105                 110

Asp Thr Ala Val Tyr Tyr Cys Ala Ser Pro Asn Tyr Pro Phe Tyr Ala
        115                 120                 125

Met Asp Tyr Trp Gly Gln Gly Thr Leu Val Thr Val Ser Ser
    130                 135                 140

<210> SEQ ID NO 27
<211> LENGTH: 426
<212> TYPE: DNA
<213> ORGANISM: artificial sequence
<220> FEATURE:
<223> OTHER INFORMATION: synthetic construct

<400> SEQUENCE: 27
```

```
atggacccca agggcagcct gagctggaga atcctgctgt tcctgagcct ggccttcgag      60
ctgagctacg gcgaagtgca gctgcaggaa tctggccctg gcctcgtgaa gccttccgag     120
accctgtccc tgacctgctc cgtgtccggc gactctatca cctccggcta ctggaactgg     180
atccggcagc ctcctggcaa gggcctggag tatatcggct acatctccta ctccggctcc     240
acctactaca accccagcct gaagtccaga gtgaccatct cccgggacac ctccaagaac     300
cagtactccc tgcggctgtc ctccgtgacc gctgctgata ccgccctgta ctactgcgcc     360
tcccccaact acccctccta cgccatggac tactggggcc agggcacaag agtgaccgtg     420
tcctct                                                                426
```

```
<210> SEQ ID NO 28
<211> LENGTH: 142
<212> TYPE: PRT
<213> ORGANISM: artificial sequence
<220> FEATURE:
<223> OTHER INFORMATION: synthetic construct

<400> SEQUENCE: 28
```

```
Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Gln Glu Ser Gly
            20                  25                  30

Pro Gly Leu Val Lys Pro Ser Glu Thr Leu Ser Leu Thr Cys Ser Val
        35                  40                  45

Ser Gly Asp Ser Ile Thr Ser Gly Tyr Trp Asn Trp Ile Arg Gln Pro
    50                  55                  60

Pro Gly Lys Gly Leu Glu Tyr Ile Gly Tyr Ile Ser Tyr Ser Gly Ser
65                  70                  75                  80

Thr Tyr Tyr Asn Pro Ser Leu Lys Ser Arg Val Thr Ile Ser Arg Asp
                85                  90                  95

Thr Ser Lys Asn Gln Tyr Ser Leu Arg Leu Ser Ser Val Thr Ala Ala
            100                 105                 110

Asp Thr Ala Leu Tyr Tyr Cys Ala Ser Pro Asn Tyr Pro Phe Tyr Ala
        115                 120                 125

Met Asp Tyr Trp Gly Gln Gly Thr Arg Val Thr Val Ser Ser
    130                 135                 140
```

```
<210> SEQ ID NO 29
<211> LENGTH: 387
<212> TYPE: DNA
<213> ORGANISM: artificial sequence
<220> FEATURE:
<223> OTHER INFORMATION: synthetic construct

<400> SEQUENCE: 29
atgtacagga tgcaactcct gtcttgcatt gcactaagtc ttgcacttgt cacgaattca      60
gatatccaga tgacacagac tacatcctcc ctgtctgcct ctctgggaga cagagtcacc     120
atcagttgca gtgcaagtca ggacattagc aattatttaa actggtatca gcagaaacca     180
gatggaactg ttaaactcct gatctattac acatcaagtt acactcagg agtcccatca      240 aggttcagtg gcagtgggtc tgggacagat tattctctca ccatcagcag cctggaacct     300
gaagatattg ccacttacta ttgtcatcag tttagtgagc ttccgtggac gttcggtgga     360
ggcaccaagc tggaaataaa acgtacg                                         387
```

```
<210> SEQ ID NO 30
```

<211> LENGTH: 129
<212> TYPE: PRT
<213> ORGANISM: artificial sequence
<220> FEATURE:
<223> OTHER INFORMATION: synthetic construct

<400> SEQUENCE: 30

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Thr Thr Ser Ser Leu Ser
            20                  25                  30

Ala Ser Leu Gly Asp Arg Val Thr Ile Ser Cys Ser Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Ser Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Ser Leu Glu Pro Glu Asp Ile Ala Thr Tyr Tyr Cys His Gln Phe Ser
            100                 105                 110

Glu Leu Pro Trp Thr Phe Gly Gly Gly Thr Lys Leu Glu Ile Lys Arg
        115                 120                 125

Thr
```

<210> SEQ ID NO 31
<211> LENGTH: 420
<212> TYPE: DNA
<213> ORGANISM: artificial sequence
<220> FEATURE:
<223> OTHER INFORMATION: synthetic construct

<400> SEQUENCE: 31

```
atgtacagga tgcaactcct gtcttgcatt gcactaagtc ttgcacttgt cacgaattcg    60
caggttactc tgaaagagtc tggccctggg atattgaagc cctcacagac cctcagtctg   120
acttgttctt tctctgggtt ttcactgagc acttctggta tgggtgtagg ctggattcgt   180
cagccttcag ggaagggtct ggagtggctg gcacacattt ggtgggatga tgataaatac   240
tataactcat ccctgaagag tcacctcaca atctccaagg ataccctccag aaaccaggta   300 ttcctcaaga tcaccagtgt ggacactgca gatactgcca cttactactg tgctcgaagc   360
tttggttacg tcttgactac tggggccaa ggcaccactc tcacagtctc ctcagctagc   420
```

<210> SEQ ID NO 32
<211> LENGTH: 140
<212> TYPE: PRT
<213> ORGANISM: artificial sequence
<220> FEATURE:
<223> OTHER INFORMATION: synthetic construct

<400> SEQUENCE: 32

```
Met Tyr Arg Met Gln Leu Leu Ser Cys Ile Ala Leu Ser Leu Ala Leu
1               5                   10                  15

Val Thr Asn Ser Gln Val Thr Leu Lys Glu Ser Gly Pro Gly Ile Leu
            20                  25                  30

Lys Pro Ser Gln Thr Leu Ser Leu Thr Cys Ser Phe Ser Gly Phe Ser
        35                  40                  45

Leu Ser Thr Ser Gly Met Gly Val Gly Trp Ile Arg Gln Pro Ser Gly
    50                  55                  60
```

```
Lys Gly Leu Glu Trp Leu Ala His Ile Trp Trp Asp Asp Lys Tyr
 65              70                  75                  80

Tyr Asn Ser Ser Leu Lys Ser His Leu Thr Ile Ser Lys Asp Thr Ser
             85                  90                  95

Arg Asn Gln Val Phe Leu Lys Ile Thr Ser Val Asp Thr Ala Asp Thr
            100                 105                 110

Ala Thr Tyr Tyr Cys Ala Arg Ser Phe Gly Tyr Gly Leu Asp Tyr Trp
            115                 120                 125

Gly Gln Gly Thr Thr Leu Thr Val Ser Ser Ala Ser
            130             135             140
```

BAFF-R ANTIBODIES AND USES THEREOF

CROSS-REFERENCE TO RELATED APPLICATION

This application is a continuation of U.S. application Ser. No. 16/307,434, filed Dec. 5, 2018, which is a National Phase application under 35 U.S.C. § 371 of International Application No. PCT/US2017/036181, filed Jun. 6, 2017, which claims priority to U.S. Provisional Application No. 62/346,324, filed Jun. 6, 2016, which are incorporated herein by reference in their entireties.

BACKGROUND

Antibody therapy is one of the most successful immunotherapies available in the clinic to treat hematological malignancies. An exemplary case is rituximab, which targets CD20 and elicits a cytotoxic effect against B cell lymphomas. However, a major concern regarding rituximab is the emergence of rituximab-resistance thought to be due to the down-regulation of CD20, thus hindering antibodies from binding the target cell.

BRIEF SUMMARY

Provided herein are B cell activating factor receptor (BAFF-R) antibodies including a light chain variable region and a heavy chain variable region. The light chain variable region includes a CDR L1 as set forth in SEQ ID NO:1, a CDR L2 as set forth in SEQ ID NO:2 and a CDR L3 as set forth in SEQ ID NO:3. And the heavy chain variable region includes a CDR H1 as set forth in SEQ ID NO:4, a CDR H2 as set forth in SEQ ID NO:5, and a CDR H3 as set forth in SEQ ID NO:6. In another aspect, the light chain variable region includes a CDR L1 as set forth in SEQ ID NO:7, a CDR L2 as set forth in SEQ ID NO:8 and a CDR L3 as set forth in SEQ ID NO:9. And the heavy chain variable region includes a CDR H1 as set forth in SEQ ID NO:10, a CDR H2 as set forth in SEQ ID NO:11, and a CDR H3 as set forth in SEQ ID NO:12. Optionally, the antibody is a humanized antibody. Also provided are functional fragments of the disclosed antibodies.

A humanized B cell activating factor receptor (BAFF-R) antibody capable of binding BAFF-R with a $K_D$ of less than about 4 nM or a functional fragment thereof is provided.

A humanized B cell activating factor receptor (BAFF-R) antibody bound to a BAFF-R at a $K_D$ of less than about 4 nM is also provided.

Also provided are chimeric antigen receptors (CAR) including an antibody provided herein or a functional fragment thereof.

Isolated nucleic acids encoding BAFF-R antibodies or functional fragments of the antibodies are provided herein.

Also provided are pharmaceutical compositions including a therapeutically effective amount of a BAFF-R antibody or functional fragment thereof as disclosed herein and a pharmaceutically acceptable excipient.

A mouse fibroblast cell expressing a human BAFF-R protein or functional fragment thereof is provided and the human BAFF-R protein or functional fragment thereof is expressed on the cell surface of the cell.

Methods of treating cancer in a subject in need thereof are provided. The methods include administering to a subject a therapeutically effective amount of a chimeric antigen receptor provided herein, thereby treating cancer in the subject.

Also provided are methods of treating cancer in a subject in need thereof including administering to a subject a therapeutically effective amount of an antibody or functional fragment thereof disclosed herein, thereby treating cancer in the subject.

Methods of treating an autoimmune disease in a subject in need thereof are provided. The methods include administering to the subject a therapeutically effective amount of an antibody or functional fragment thereof as disclosed herein, thereby treating an autoimmune disease in the subject.

Also provided are methods of inhibiting proliferation of a cell. The methods include contacting a cell with a BAFF-R antibody or functional fragment thereof as disclosed herein, thereby forming a contacted cell. The BAFF-R antibody or functional fragment thereof is allowed to bind a BAFF-R protein on the contacted cell, thereby inhibiting proliferation of the cell. Optionally, the cell is a lymphoid cell.

Methods of producing an anti-human BAFF-R antibody or functional fragment thereof are provided. The methods include administering a mouse fibroblast cell that expresses a BAFF-R protein or fragment thereof as provided herein to a mouse, thereby forming an immunized BAFF-R mouse. A splenic cell from the immunized BAFF-R mouse is fused with a human myeloma cell, thereby forming a BAFF-R hybridoma cell. The BAFF-R hybridoma cell is then allowed to express a BAFF-R antibody, thereby producing an anti-BAFF-R antibody.

BRIEF DESCRIPTION OF THE DRAWINGS

FIG. 1A is a FACS analysis of cell surface expression of hBAFF-R-GFP fusion protein in mouse fibroblast L cells. Gated on GFP-positive cells, engineered L cell clone (right plot) is compared to parental L cells (left plot). Clone D2C was selected for further studies. FIGS. 1B, 1C, 1D and 1E are FACS traces of fluorescent counts of anti-BAFF-R antibodies binding cell lines and patient samples. FIG. 1B shows affinity purified hybridoma mAb (C90, C67, C55, and C53) binding BAFF-R-positive, human MCL lines including Mino, JeKo-1, REC-1, JVM-13, and Z-138 at a concentration of 0.05 μg mAb/$10^6$ cells. BAFF-R-negative 293T embryonic kidney cell line was used as a control. FIG. 1C shows chimeric antibodies C55 and C90 at high and low concentration binding hBAFF-R-expressing L cells. Parental L cells and secondary anti-hIgG-APC antibodies only were used as controls. FIG. 1D shows alexa fluor 488-conjugated chimeric antibodies binding a panel of NHL cell lines. FIG. 1E shows chimeric antibodies binding three types of NHL primary patient samples. The data are representative of three independent experiments. For all of FIGS. 1B-1E, the traces from top to bottom as shown in the figures correlate with the variables (e.g., antibody type or cell type) used from top to bottom shown below or next to the figures.

FIG. 2B shows specific lysis of antibodies mixed with active complement-containing human serum (1:3 dilution) against CDC-sensitive (Raji) and -resistant (Raji-2P). FIG. 2C shows ADCC effects by BAFF-R chimeric antibodies with or without NK effector cells (E:T=20:1) on NHL lines JeKo-1, SU-DHL-6, Raji, and RL. Data are shown as the mean±s.d. of triplicate samples. *P<0.05 compared with NK cells by two-tailed Student's t-test.

FIG. 3A shows NHL patient samples (E:T=20:1 or 10:1); FIG. 3B shows primary MCL and CLL samples from rituximab-treated refractory patients (E:T=20:1). Data are shown as the mean±s.d. of triplicate samples. *P<0.05 compared with NK cells by two-tailed Student's t-test.

FIG. 5A is a scatterplot of FACS analysis showing CD20 binding on JeKo-1 cells following CRISPR/HDR knock-out of CD20 gene. CD20 expression on selected CD20−/−clone #25 compared to WT JeKo-1. ADCC effects measured by chromium-51 release after incubation with C55, C90, or rituximab and effectors NK cells (E:T=20:1). Percentage of cell specific lysis of target cells: rituximab-resistant JeKo-1-CD20-KO (FIG. 5B) and ibrutinib-resistant Z-138 and SP49-IR (FIG. 5C). All data are representative of two or more identical experiments. Data are shown as the mean±s.d. of triplicate samples. *P<0.05 compared with NK cells by two-tailed Student's t-test.

FIG. 6C shows 80-day tumor-free and overall survival curves of the mice shown in (A) and (B), respectively. Tumor free rate and survival differences between experimental and all control groups were analyzed by log-rank test (**P<0.001). Data are representative of three independent experiments.

FIGS. 7A and 7B show anti-human BAFF-R monoclonal antibody generation and clone selection. FIG. 7A is a schematic showing L cell clone D2C, which stably expressed human hBAFF-R with a C-terminal GFP tag on the intracellular domain, was used to immunize BALB/c mice according to the schedule shown. Splenic tissue was harvested on day 20 and B-cell hybridoma clones were established. FIG. 7B is a table showing ELISA results from five hybridoma supernatants using anti-mouse IgG-HRP. Clones 53, 55, 67, and 90 produced BAFF-R-specific mAbs, whereas Clone 37 did not (representative of other negative clones).

Figure 16A:
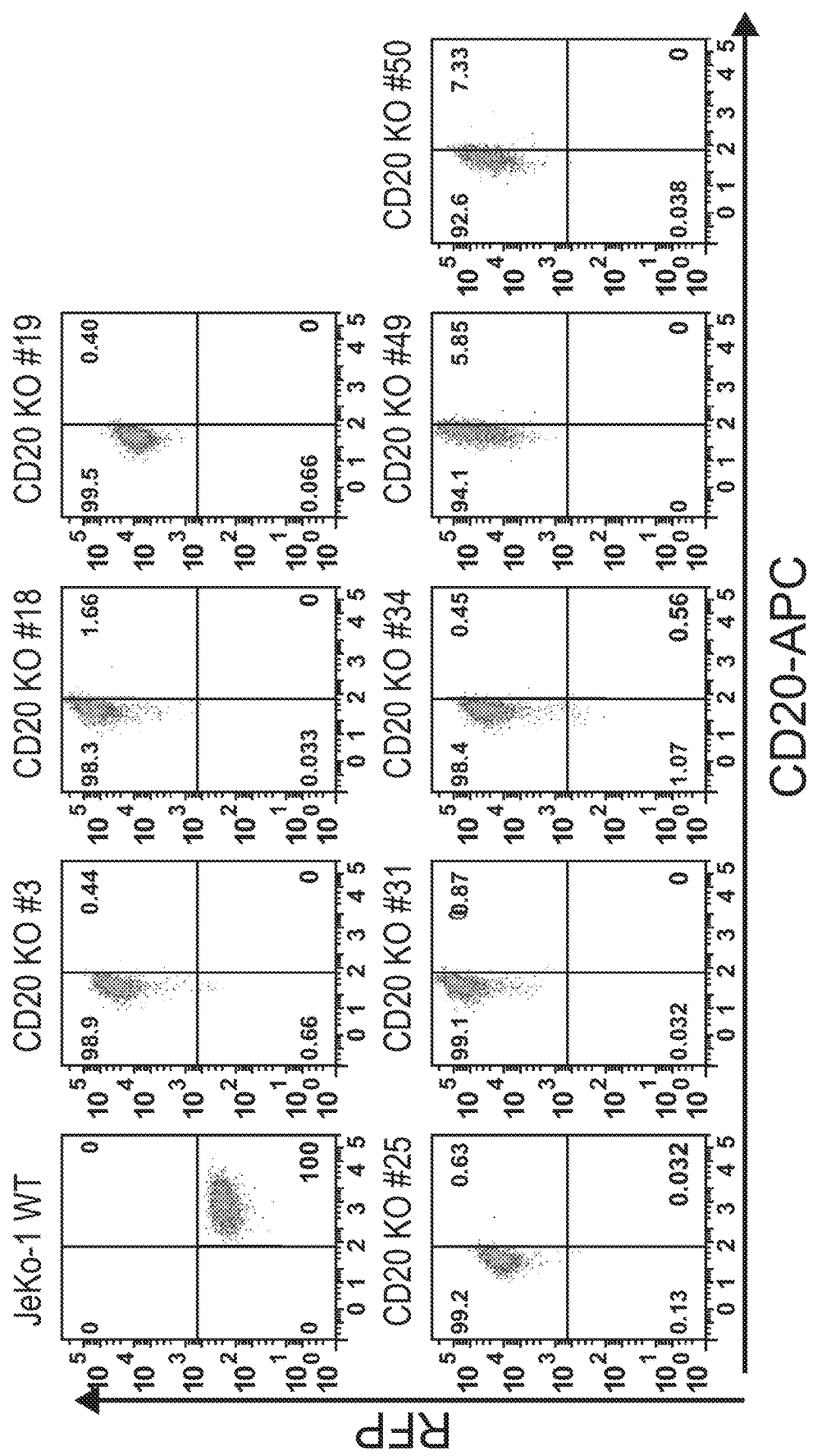
Figure 16B:
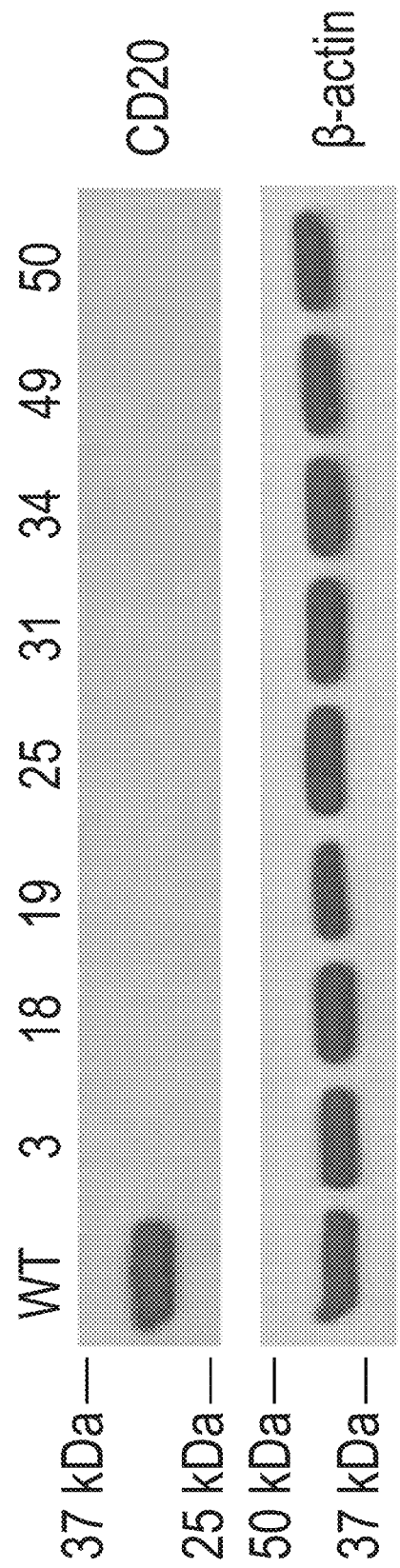
Figure 16C:
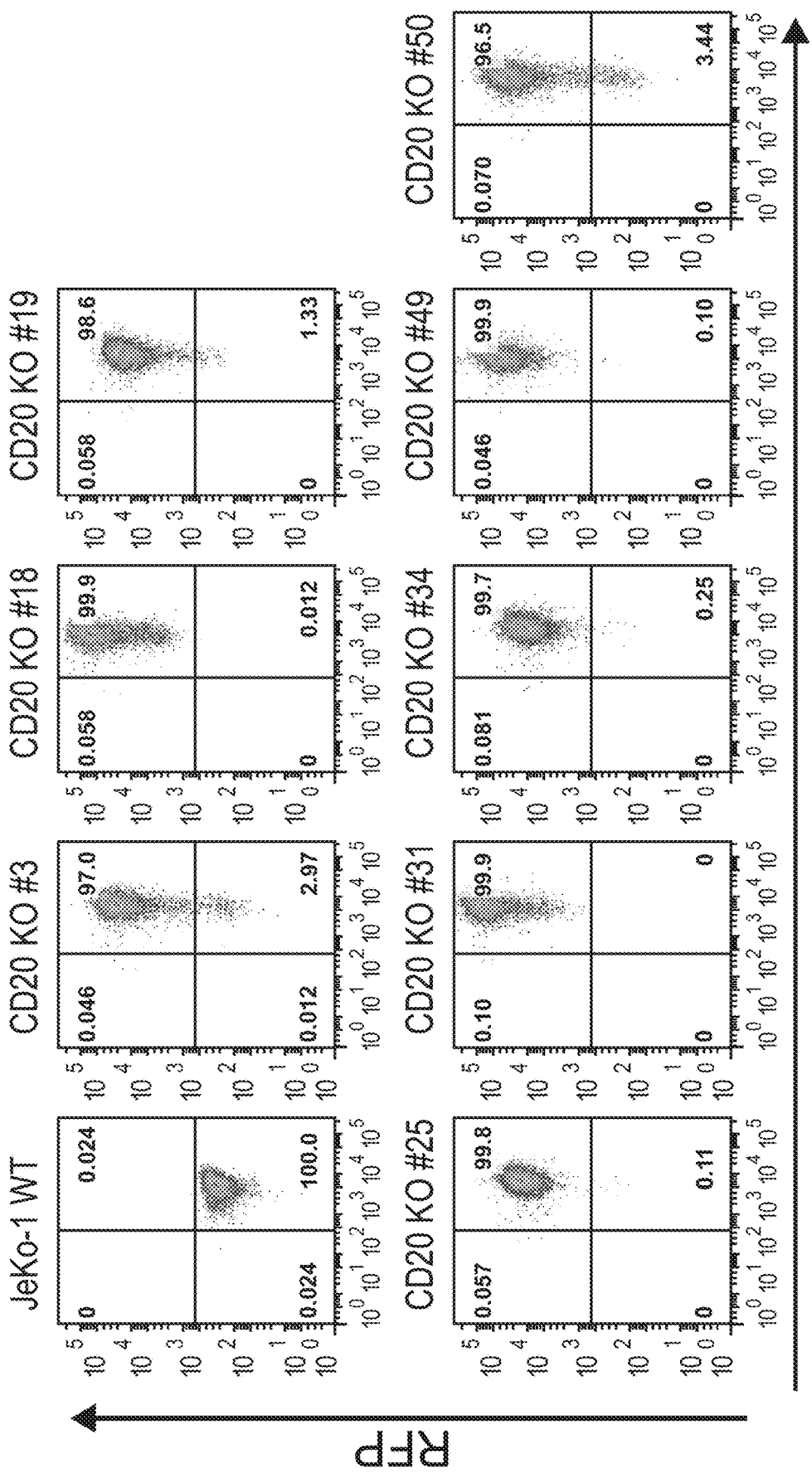

FIGS. 16A are FACS results and 16B is a gel image showing CD20 knock out clones generated with CRISPR. CD20 knock out clones of JeKo-1 were generated with a commercial CRISPR/HDR system substituting RFP at the CD20 locus. For FIG. 16A, clones were screened and sorted by flow cytometry for CD20−/RFP+ expression. For FIG. 16B, Western blotting with anti-CD20 antibodies was performed on total cell lysate from CD20−/RFP+ clones. (3-actin was blotted as a loading control. FIG. 16C shows FACS results for clones as in FIG. 16A screened for BAFF-R/RFP+ expression to confirm that BAFF-R expression had not been affected by the CRISPR/HDR manipulation of CD20.

Figure 17A:
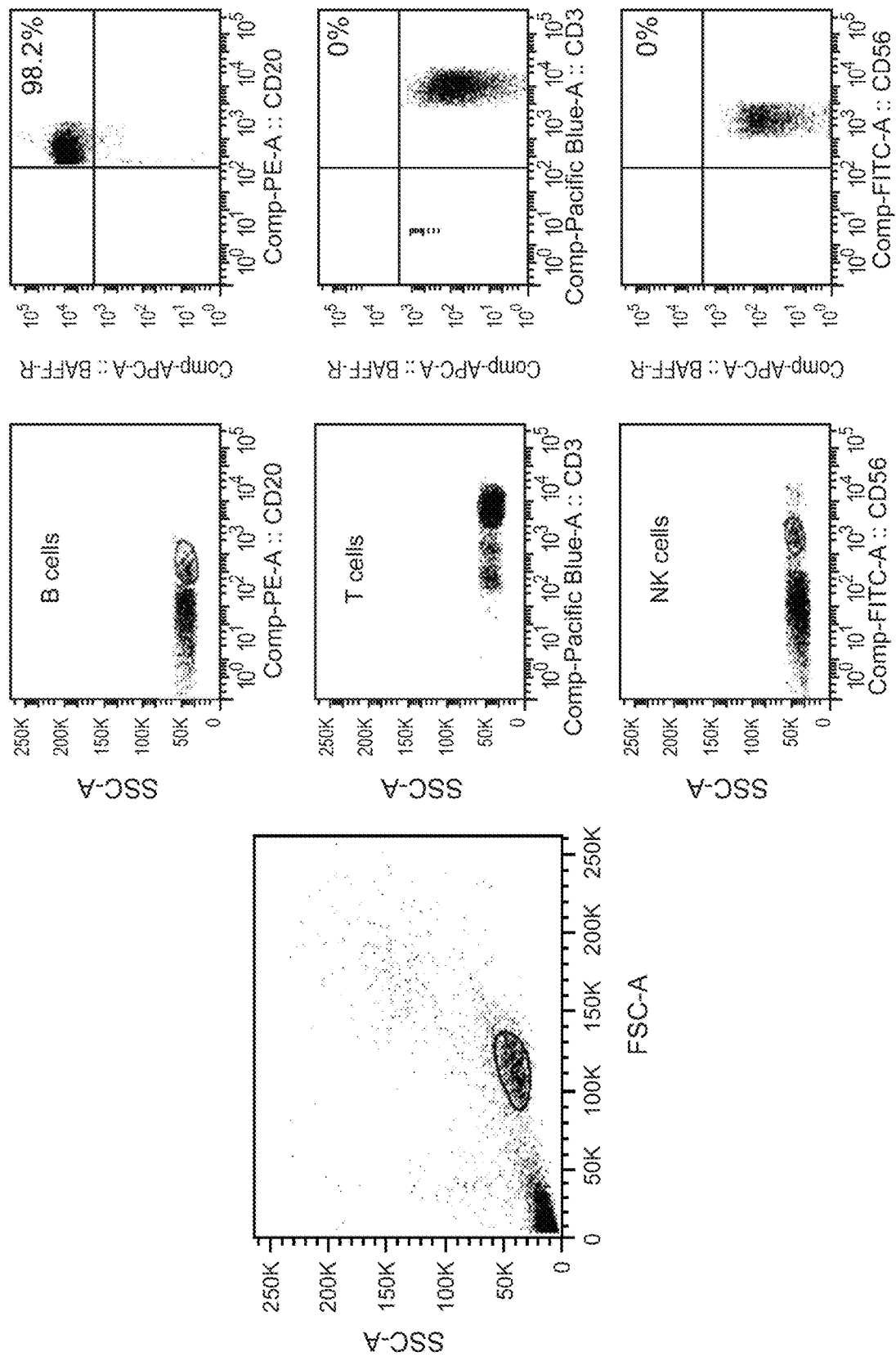
Figure 17B:
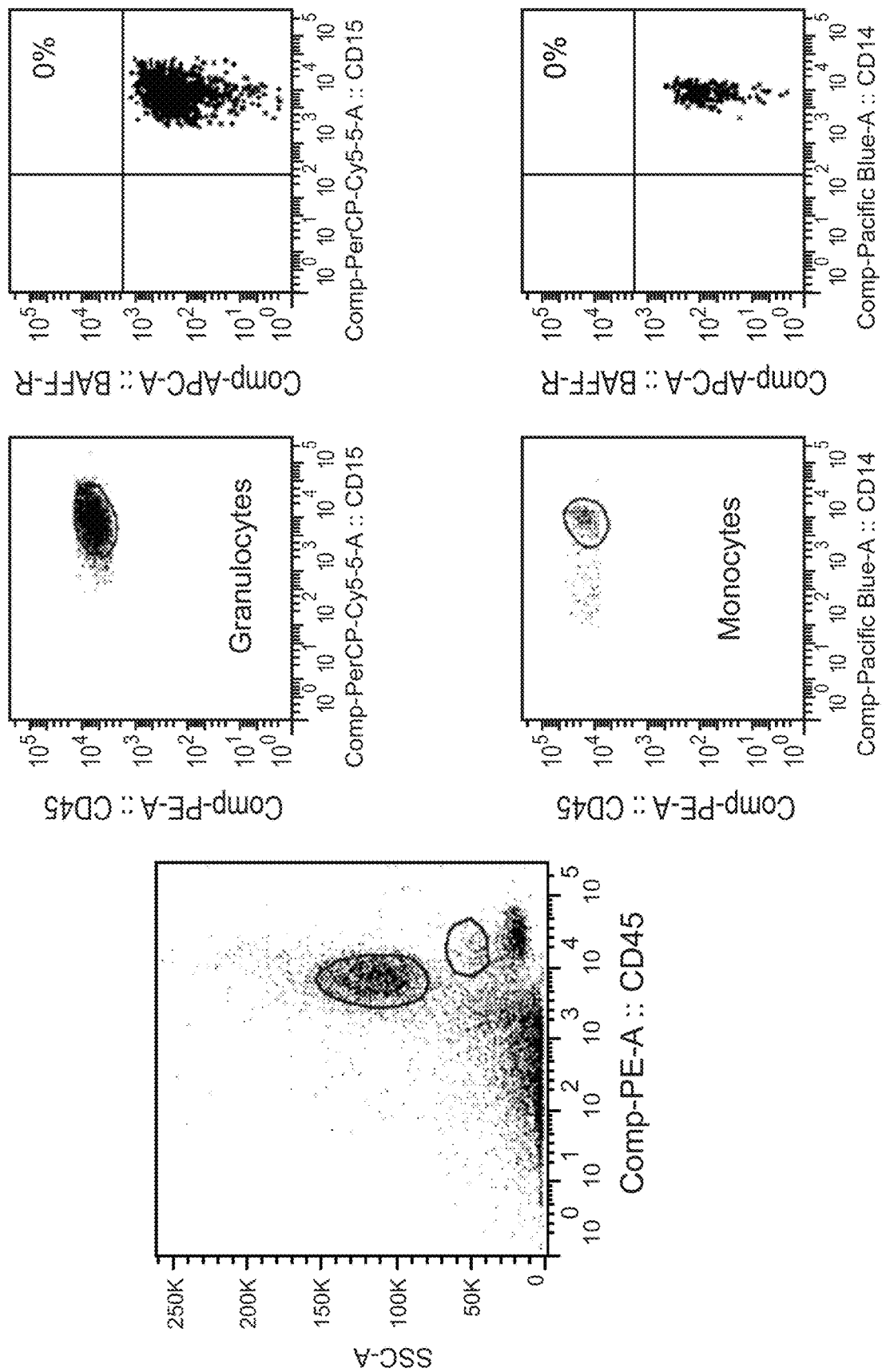

FIGS. 17A and 17B are FACS results showing characterization of BAFF-R binding against normal B cells. PBMC from healthy donors were co-stained with APC-conjugated C90 chimeric antibody and (A) a lymphocyte marker panel (anti-CD20-PE, anti-CD3-PacificBlue, and anti-CD56-FITC) or (B) a myeloid cell marker panel (anti-CD45-PE, anti-CD15-PerCP-Cy5.5, and anti-CD14-PacificBlue). Each specific immune cell sub-population was gated and analyzed for binding with BAFF-R antibodies.

Figure 18:
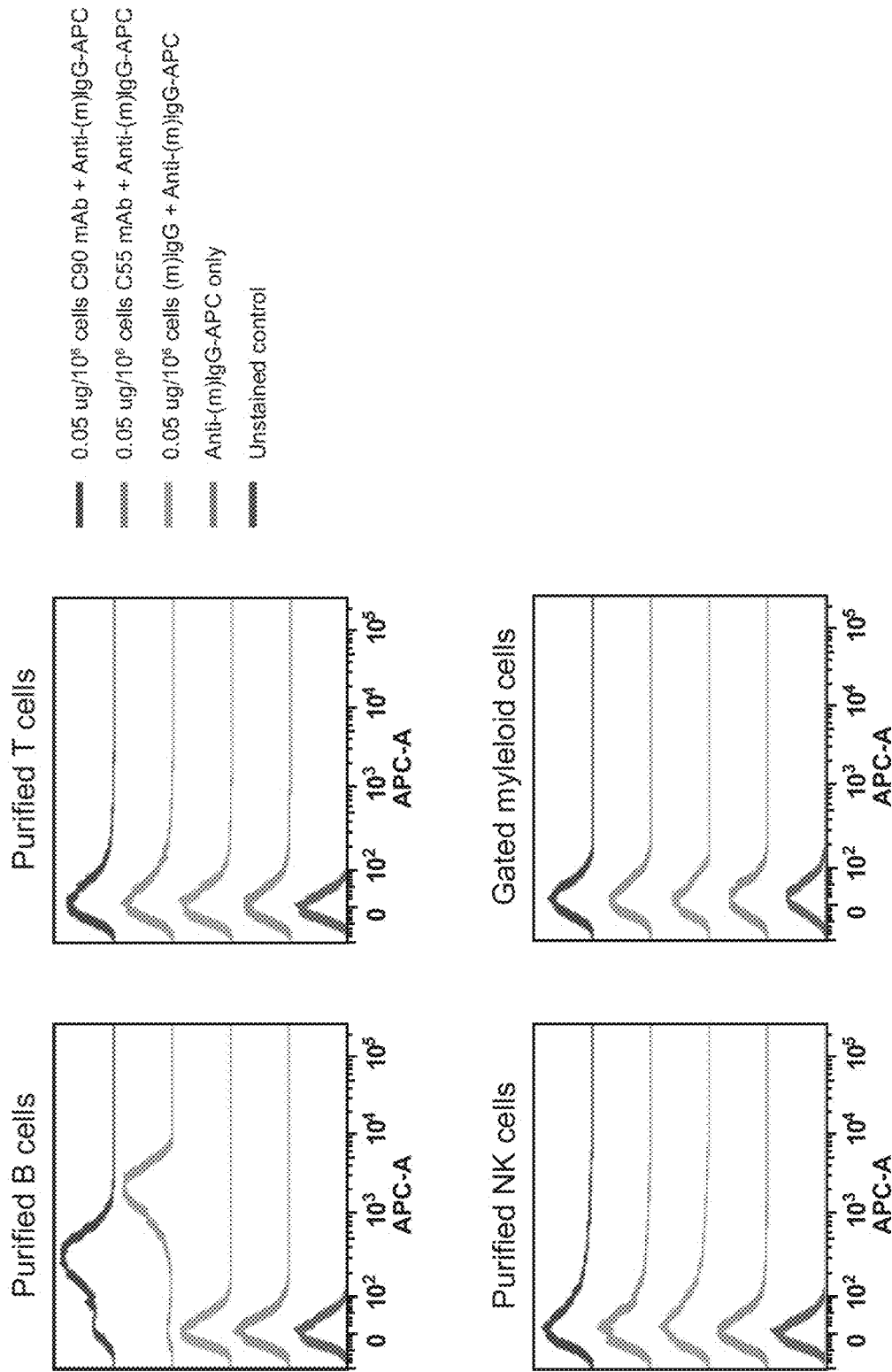

FIG. 18 provides FACS results showing characterization of hBAFF-R mAbs in normal immune cells from peripheral blood. Mouse mAb Clones 55 and 90 were tested for binding to isolated human immune cell sub-populations. B cells, T cells, and NK cells were isolated with commercial specific cell type isolation kits and stained with C55 and C90 (0.05 μg mAb/$10^6$ cells). Flow cytometry analysis was performed with anti-mouse IgG. Myeloid cells from PBMC were gated for CD66b+ and analyzed for mAb C55 and C90 staining. The traces from top to bottom as shown in the figures correlate with the variables (e.g., antibody type or cell type) used from top to bottom shown next to the figures.

Figure 19A:
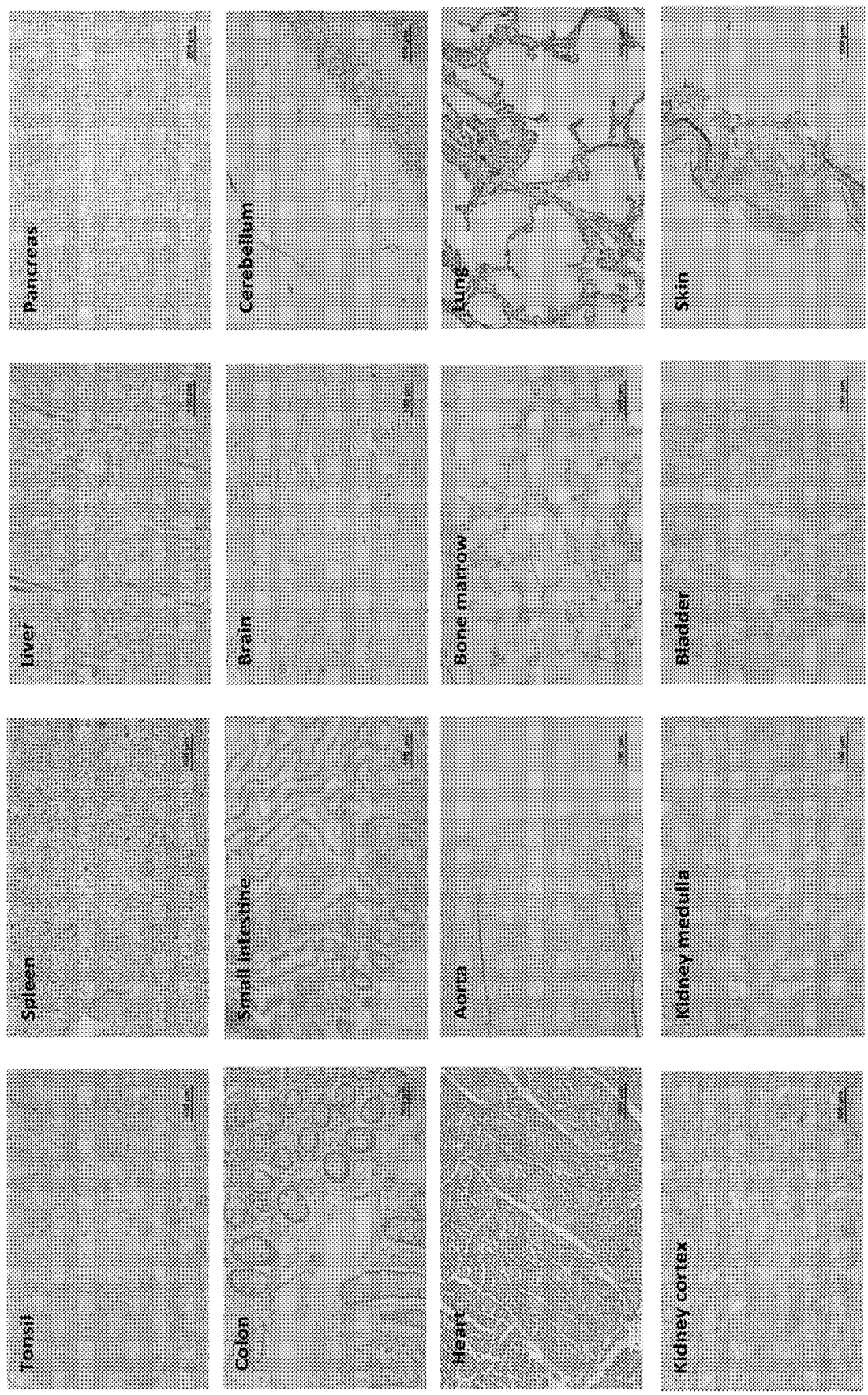
Figure 19B:
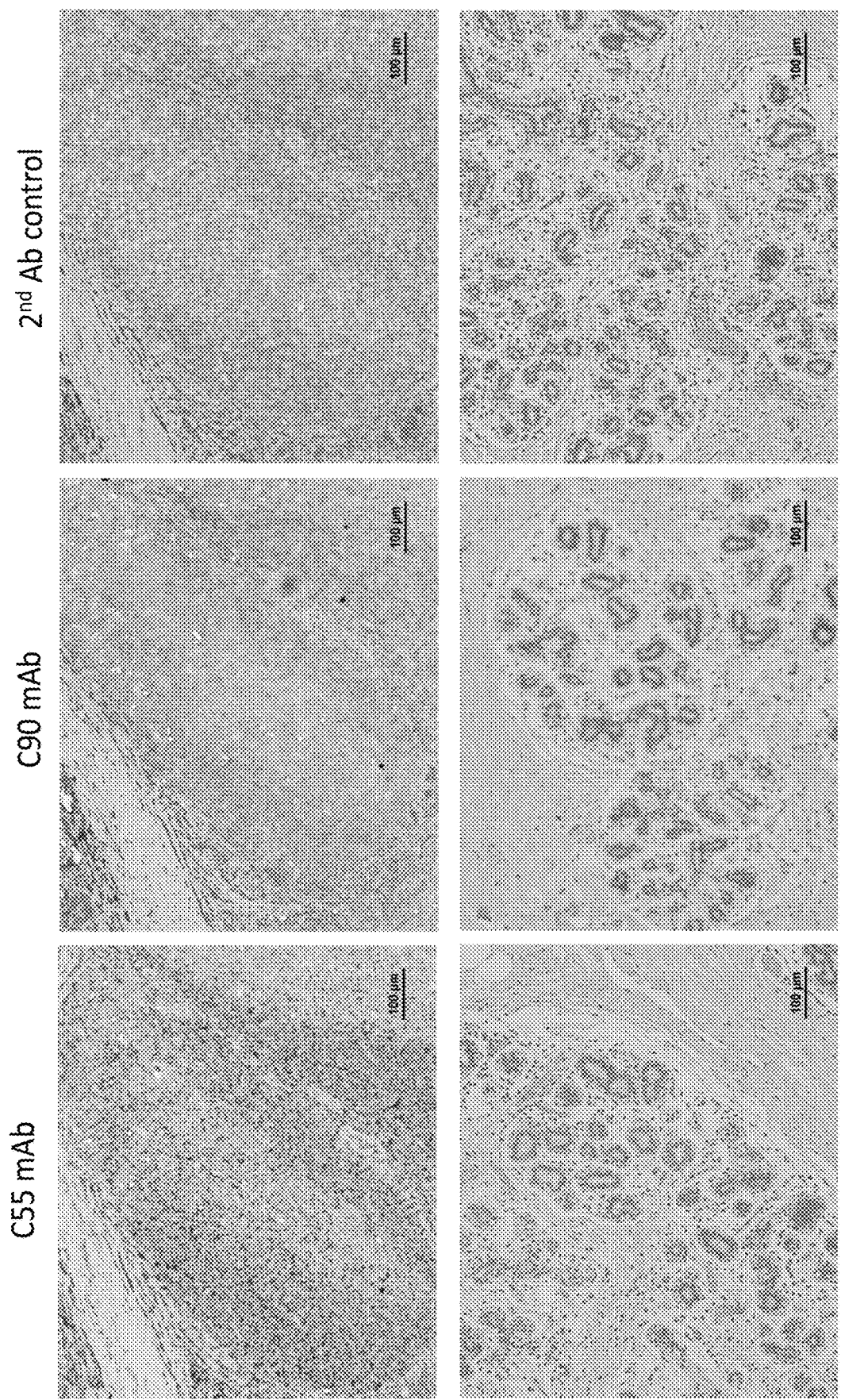

FIGS. 19A and 19B are immunohistochemistry images. For FIG. 19A, immunohistochemistry was performed to identify the tissue specificity of the anti-BAFF-R antibodies. 1:150 dilution of 1 mg/mL antibodies were used to stain tissue samples. Tissue specificity of C55 mAb against human BAFF-R (20× objective lens): 1:150 dilution of the stock at 1 mg/ml. For FIG. 19B, immunohistochemistry was performed on additional tonsil tissue and breast tissue to identify the tissue specificity of the anti-BAFF-R antibodies. 1:150 dilution of 1 mg/mL antibodies were used to stain tissue samples. Tissue specificity of mAb against human BAFF-R (upper panel: tonsil tissue; lower panel: breast tissue; 20× objective lens).

Figure 20A:
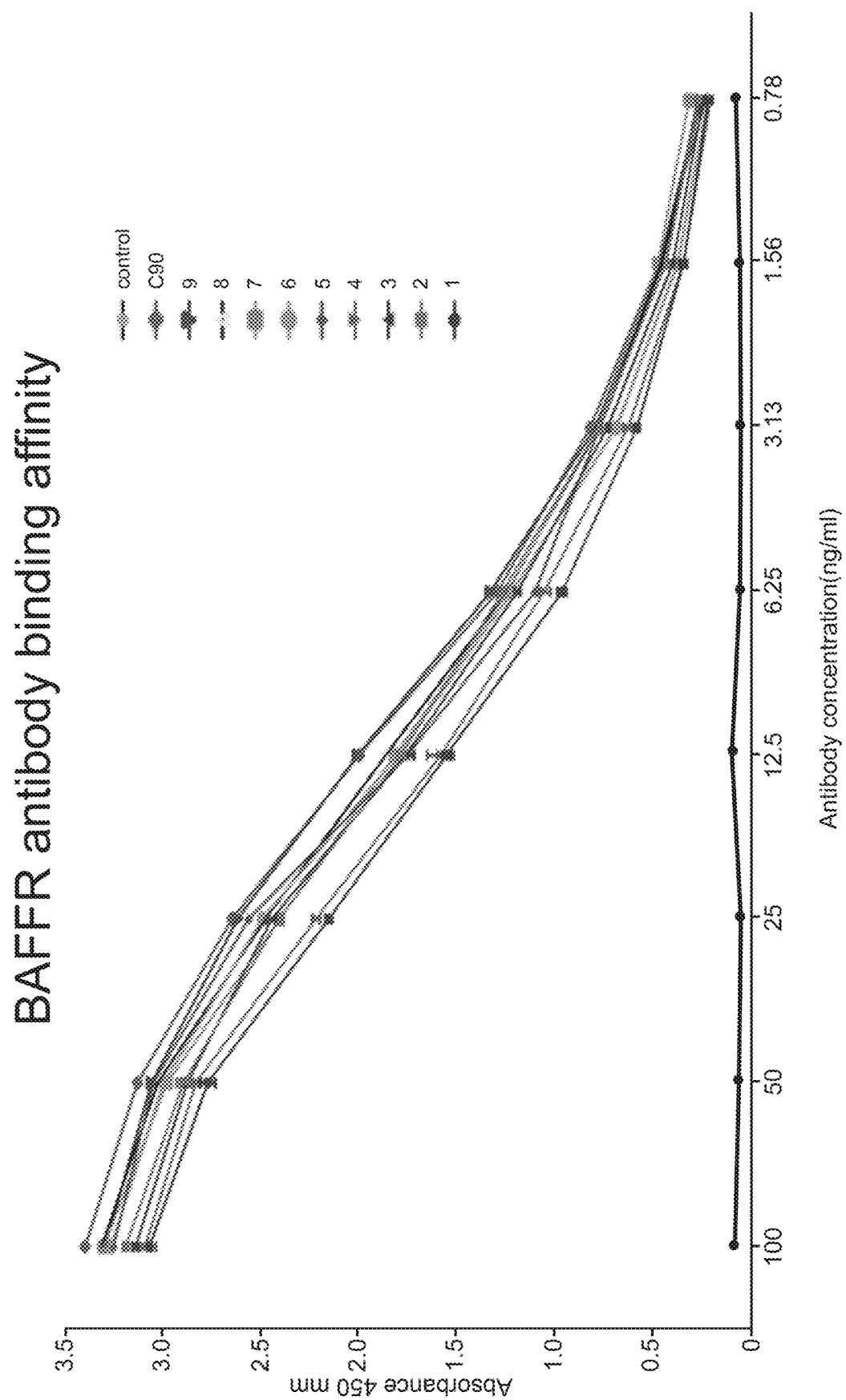
Figure 20B:
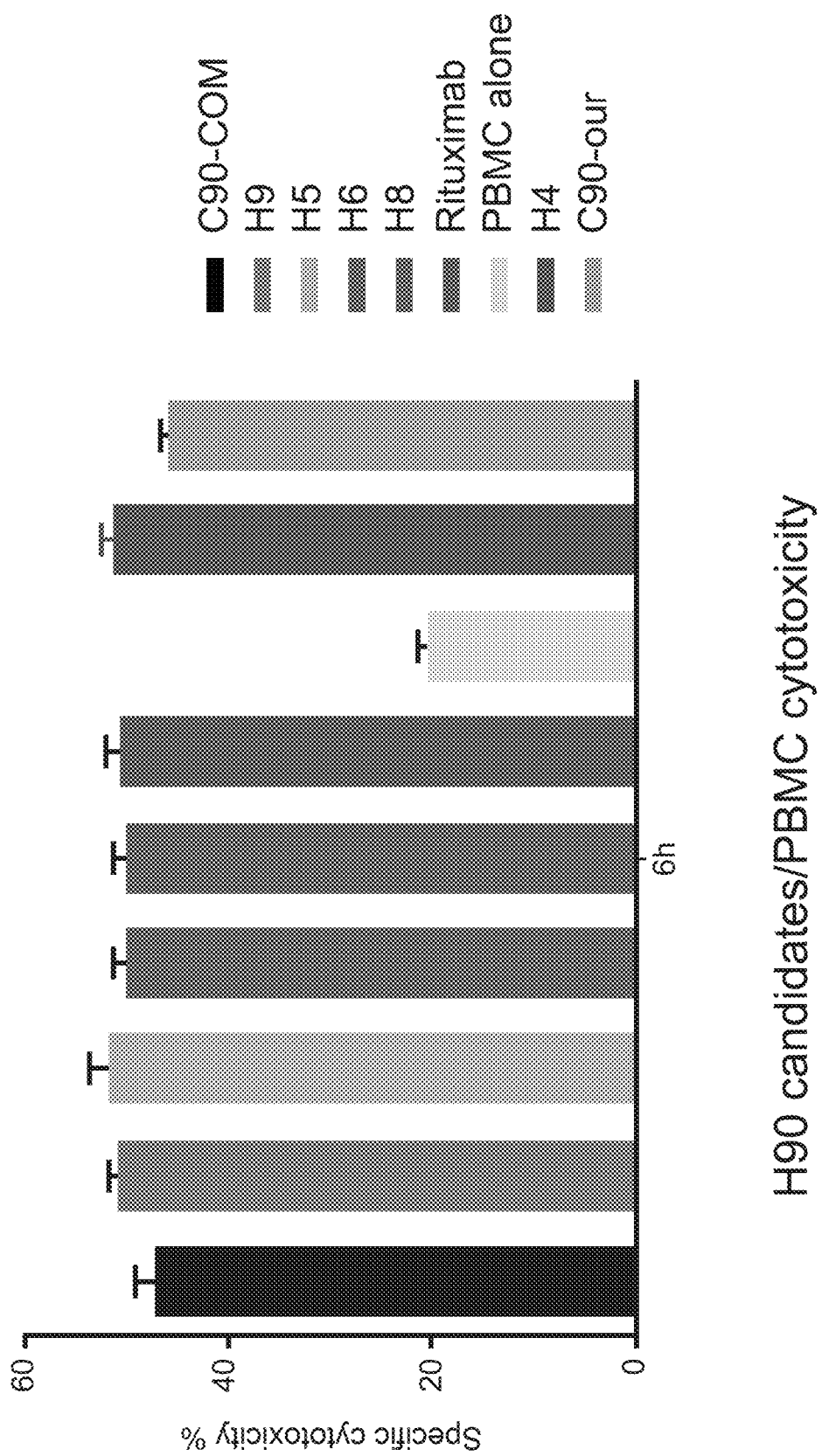

FIGS. 20A and 20B are graphs showing functional in vitro assays performed on the humanized variants. For FIG. 20A, an ELISA assay was performed on the nine humanized variants of C90. The recombinant extracellular domain of human BAFF-R was used as the antigen. The antibodies were administered at concentrations varying from 0.78 to 100 ng/mL and their absorbance taken at 450 nm. For FIG. 20B, the humanized variants were tested against JeKo-1 cells in a chromium release assay. The cells were allowed to uptake chromium followed by treatment with a humanized C90 variant and effector NK cells. The cells were incubated for 6 hours and their supernatants were sampled for their chromium content.

Figure 21A:
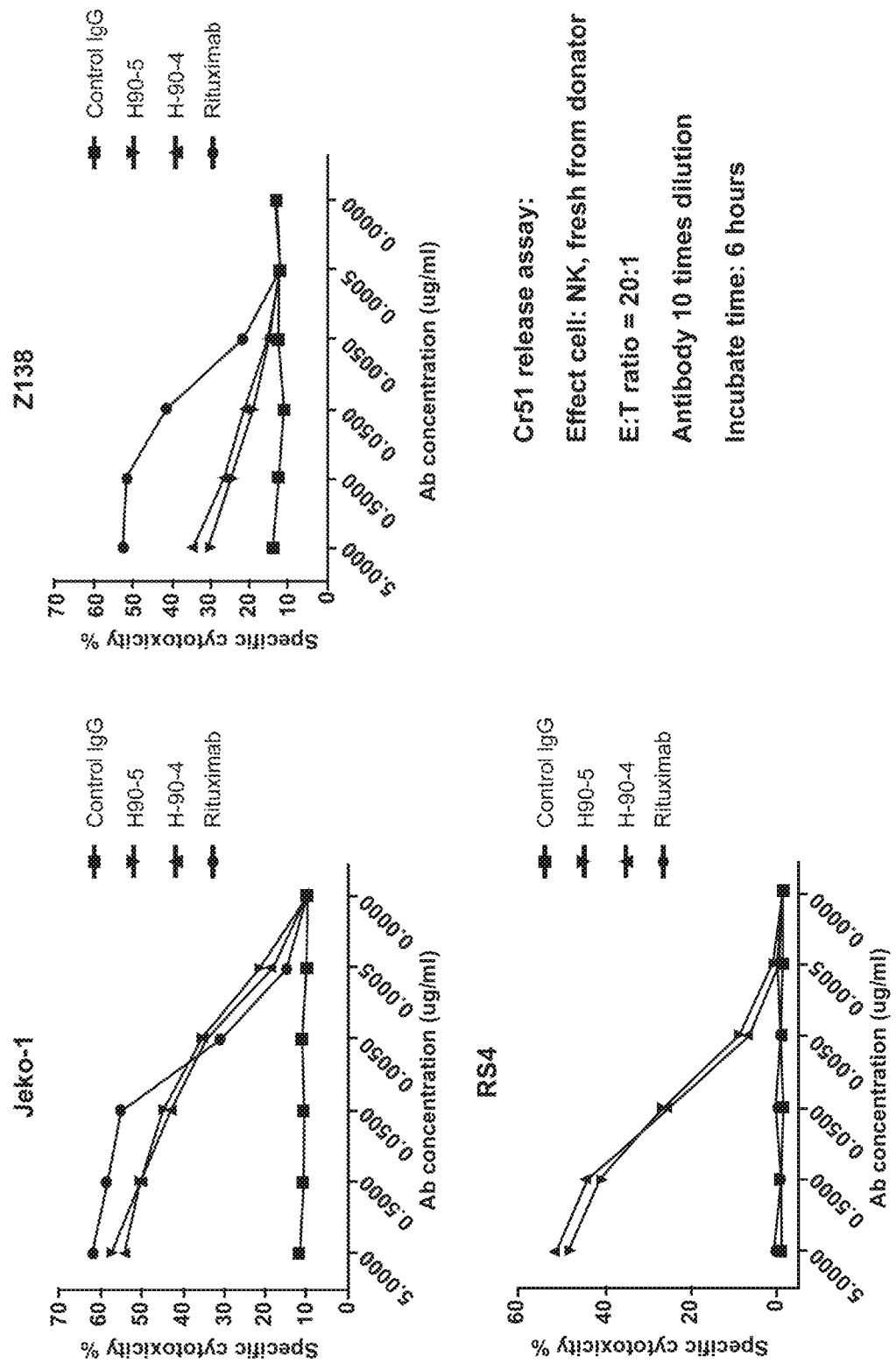
Figure 21B:
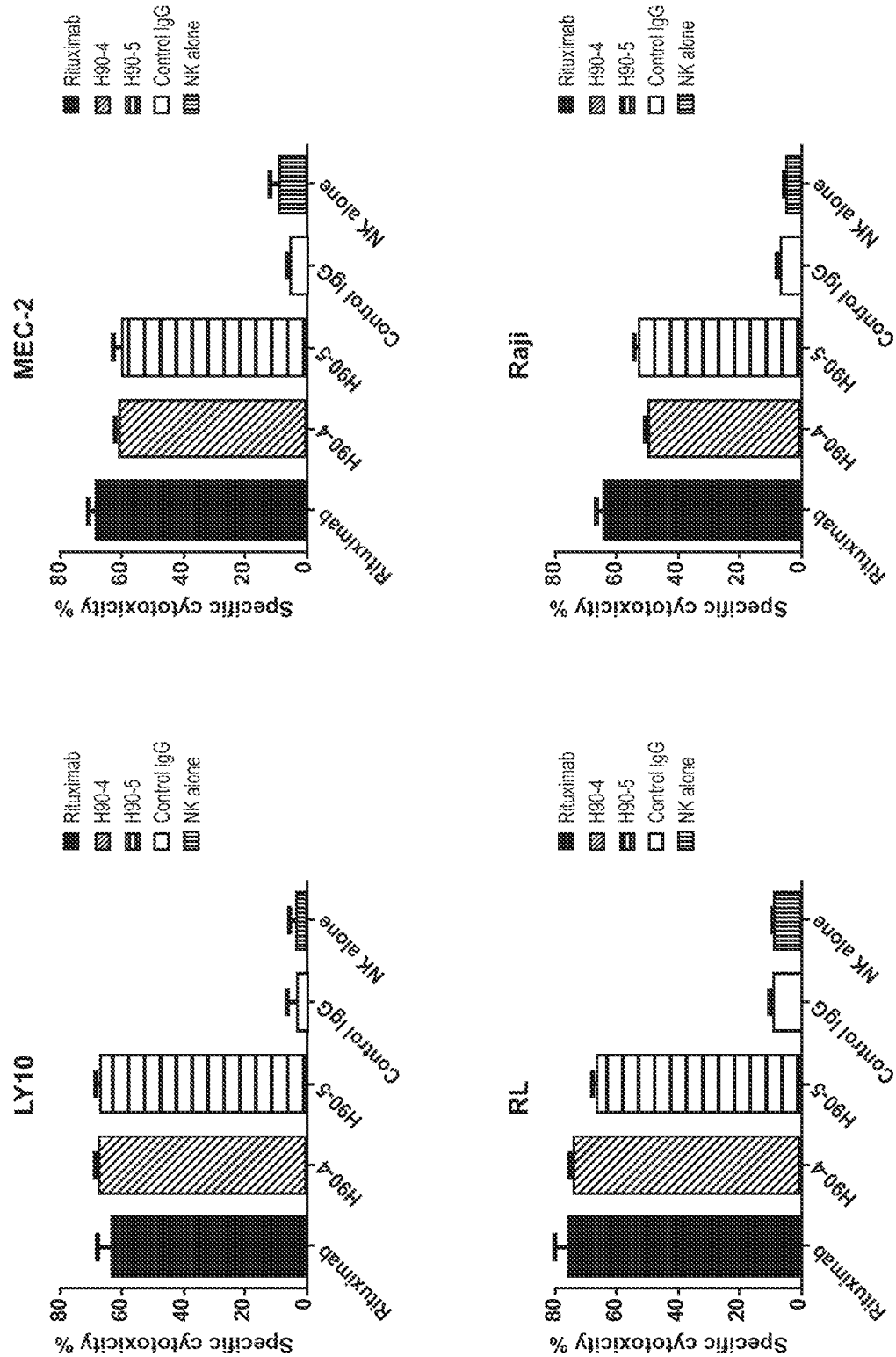

FIGS. 21A and 21B are graphs showing humanized antibodies C90-4 and C90-5 analyzed for their specific cytotoxicity of various lymphoma lines. For FIG. 21A, JeKo-1, Z138, and RS4 were subjected to a chromium release assay with humanized antibodies C90-4 and C90-5. Antibodies were administered to the cell lines at concentrations between 0 to 5 μg/mL and incubated for 6 hours with NK cells at an E:T ratio of 20:1. The cell supernatants were analyzed for their chromium content. For FIG. 21B, LY-10, MEC-2, RL, and Raji lymphoma lines were subjected to a chromium release assay with humanized antibodies C90-4 and C90-5. Antibodies were administered to the cell lines at 5 μg/mL and incubated for 6 hours with NK cells at an E:T ratio of 20:1. The cell supernatants were analyzed for their chromium content.

Figure 22A:
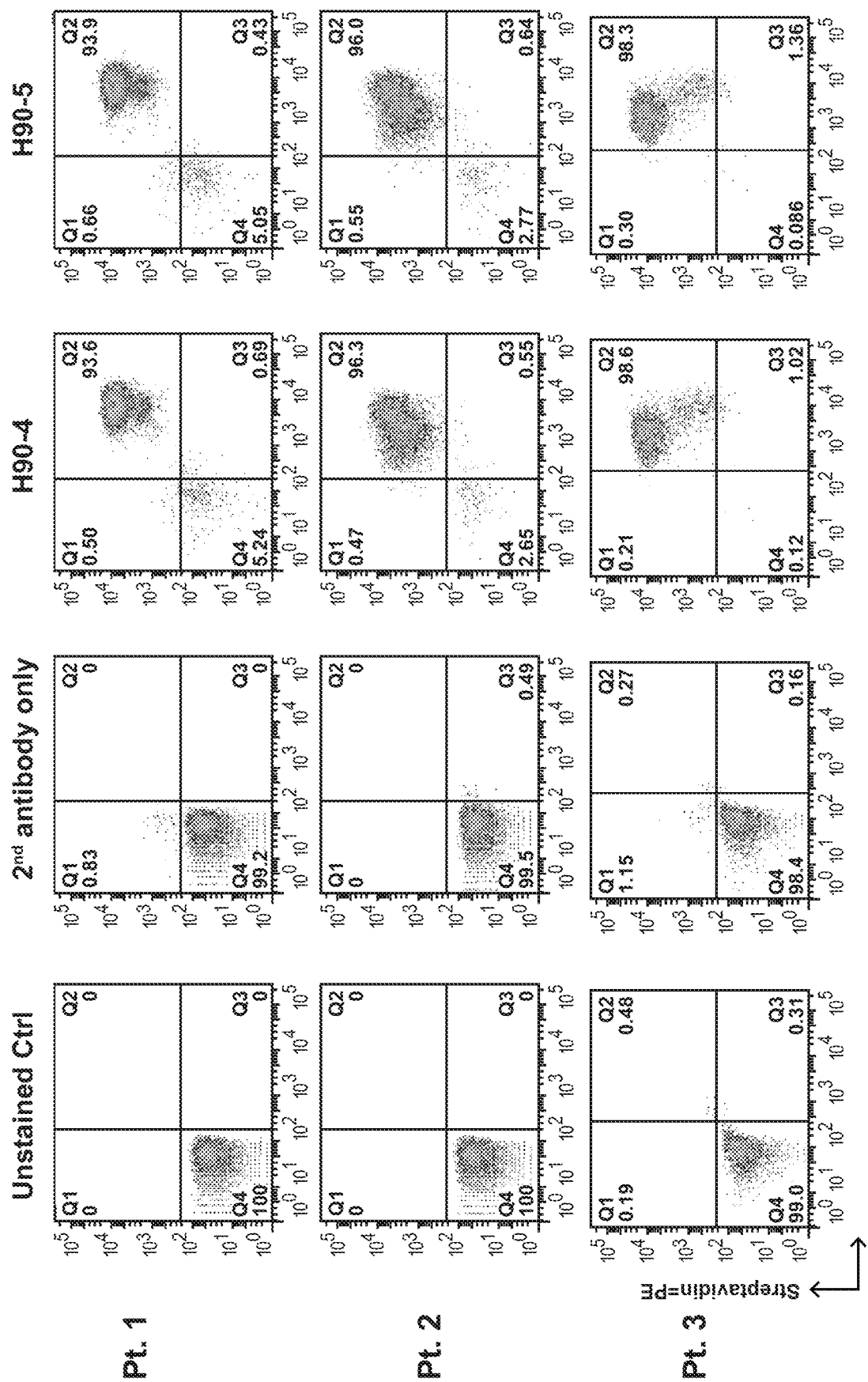
Figure 22B:
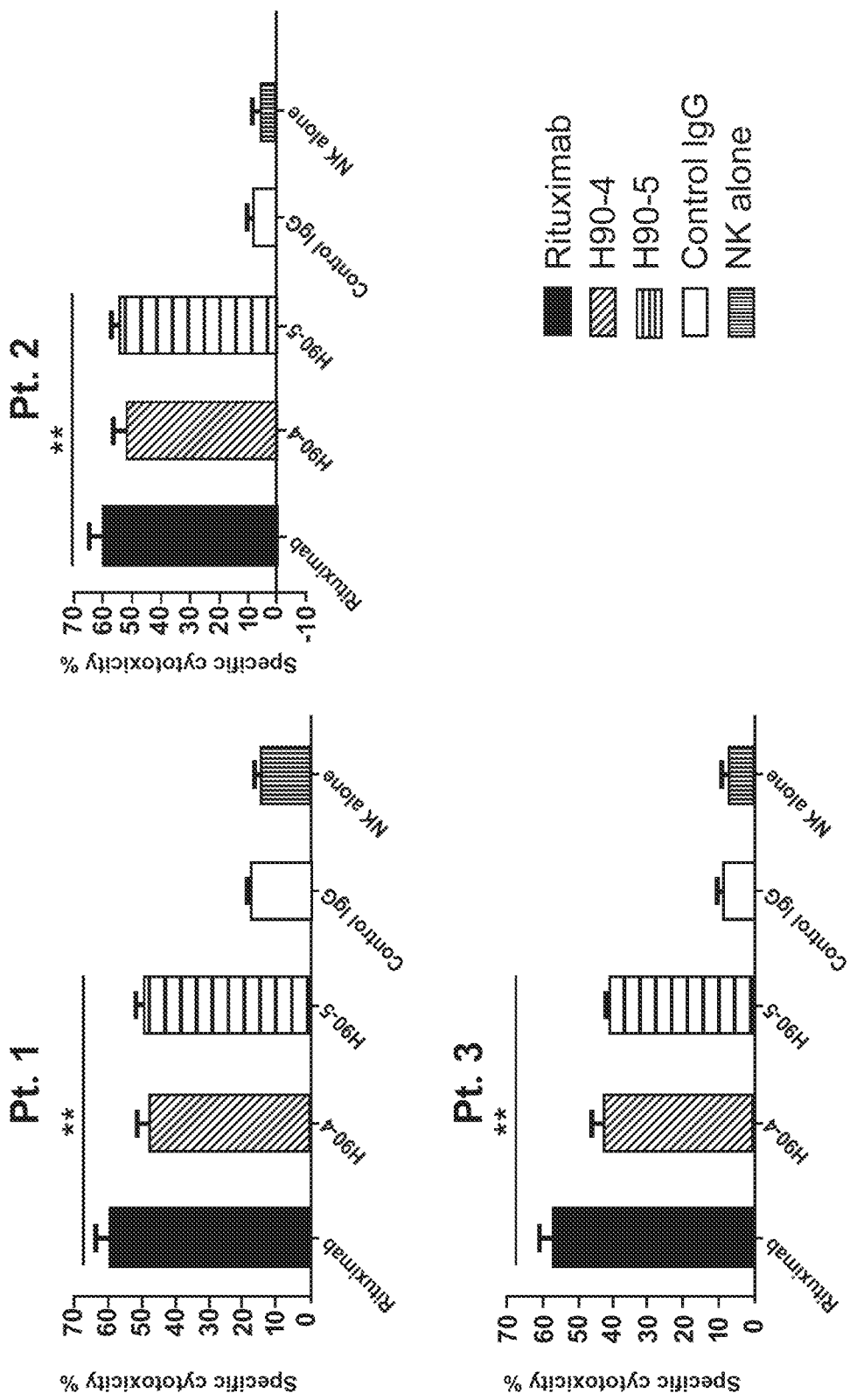

FIGS. 22A and 22B are FACS results and graphs showing humanized C90 antibody lead candidates tested for binding and cytotoxicity against primary MCL samples. For FIG. 22A, three primary MCL tumor samples were co-stained with CD20-APC and biotinylated humanize C90 followed by signal detection using PE-conjugated streptavidin. For FIG. 22B, cytotoxicity of humanized C90 against primary tumor samples were evaluated with a chromium release assay. Cells were incubated with chromium-51 followed by treatment with antibodies and effector NK cells. Following overnight incubation, supernatants were sampled and the chromium contents were determined.

Figure 23:
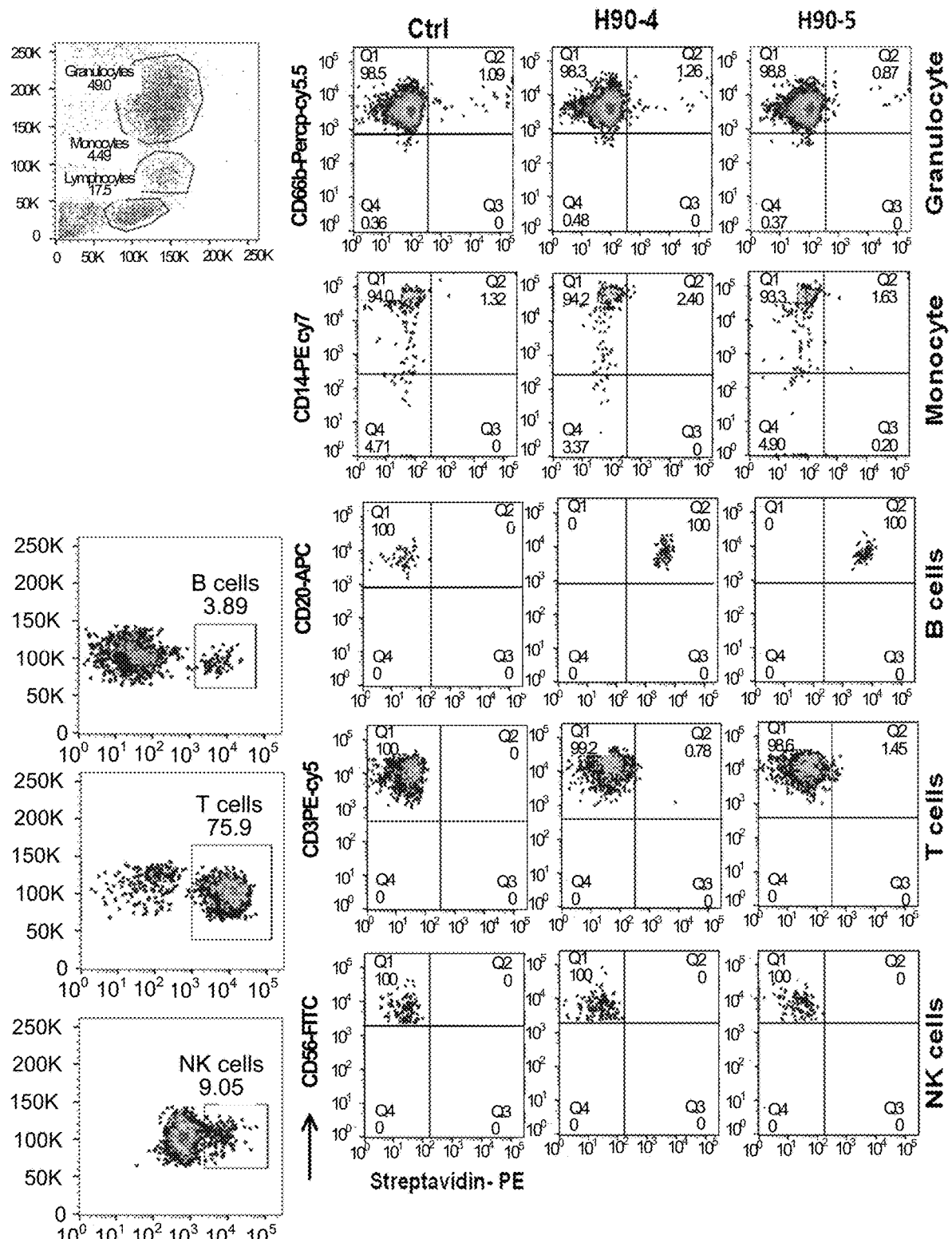

FIG. 23 are FACS results showing flow cytometry analysis of biotinylated humanized C90-4 and C90-5. The antibodies were used to stain PBMCs followed by detection with fluorescent PE streptavidin probe. The PBMCs were also labeled with granulocyte marker CD66b-PerCP-Cy5.5, monocyte marker CD14-PE-Cy7, B cell marker CD20-APC, T cell marker CD3-PE-Cy5, and NK cell marker CD56-FITC. The PBMCs were analyzed by flow cytometry.

Figure 24:
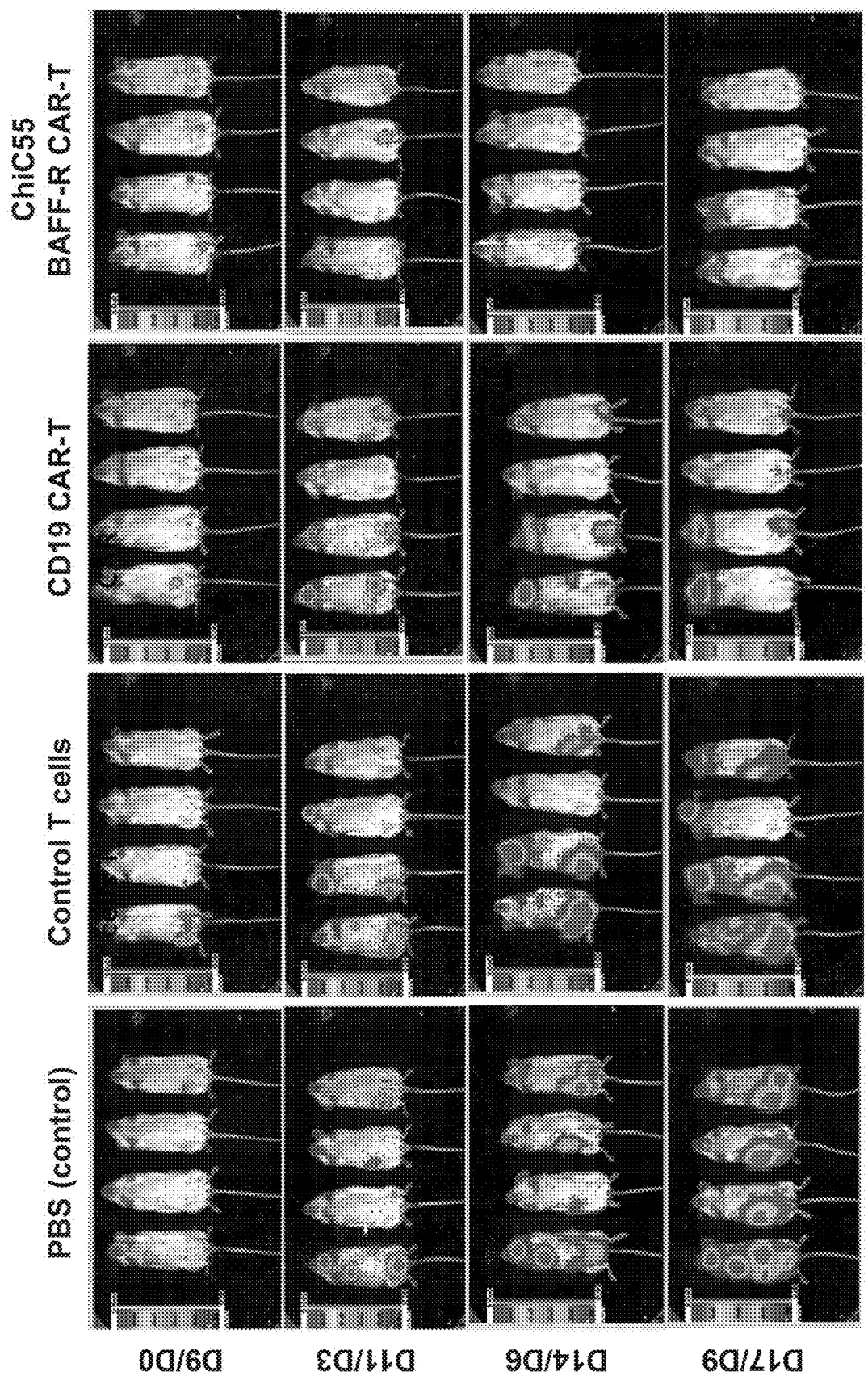

FIG. 24 are images showing BAFF-R chimeric antigen receptor (CAR) T cell in vivo tumor treatments. Donor T cells were engineered to express chimeric C55 anti-BAFF-R single chain (sFv) onto a T cell receptor signaling domain with a 4-1BB motif. NSG mice were challenged with the minimum lethal dose of NHL JeKo-1-Luci cells ($1 \times 10^6$ cells). The tumor cells were allowed to engraft until a tumor was detectable by bioluminescent imaging (Day 9). Mice were administered either a T cell therapy ($5 \times 10^6$ CAR-T cells) or controls on days 9 and 15 post tumor challenge. The mice were monitored closely and imaged every three days to track the tumor development.

DETAILED DESCRIPTION

Provided herein are, inter alia, BAFF-R antibodies including a light chain variable region and a heavy chain variable region. Functional fragments of the antibodies are also provided. The BAFF-R antibodies and functional fragments thereof provided herein are capable of binding to human BAFF-R protein and induce antibody-dependent cellular cytotoxicity (ADCC) on BAFF-R-expressing cells (e.g., B cells). Optionally, the light chain variable region and the heavy chain variable region of the antibodies provided herein form part of a chimeric antigen receptor (CAR). Thus, the compositions and methods provided herein may, inter alia, be used for the treatment of cancer (e.g., B cell malignancies) or autoimmune diseases.

A BAFF-R, BAFF receptor or BAFF-R protein as referred to herein includes any of the recombinant or naturally-occurring forms of the B-cell activating factor receptor (BAFF-R) also known as tumor necrosis factor receptor superfamily member 13C (TNFRSF13C) or variants or homologs thereof that maintain BAFF-R activity (e.g. within at least 50%, 80%, 90%, 95%, 96%, 97%, 98%, 99% or 100% activity compared to BAFF-R). Optionally, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BAFF-R. Optionally, the BAFF-R is substantially identical to the protein identified by the UniProt reference number Q96RJ3 or a variant or homolog having substantial identity thereto. Optionally, the BAFF-R is substantially identical to the protein identified by the UniProt reference number Q9D8D0 or a variant or homolog having substantial identity thereto. Optionally, the BAFF-R is substantially identical to the protein identified by the NCBI reference number GI:16445027 or a variant or homolog having substantial identity thereto. Optionally, the BAFF-R is substantially identical to the protein identified by the NCBI reference number GI:16306481 or a variant or homolog having substantial identity thereto.

A B cell activating factor receptor (BAFF-R) antibody including a light chain variable region and a heavy chain variable region is provided. The light chain variable region includes a CDR L1 as set forth in SEQ ID NO:1, a CDR L2 as set forth in SEQ ID NO:2 and a CDR L3 as set forth in SEQ ID NO:3. And the heavy chain variable region includes a CDR H1 as set forth in SEQ ID NO:4, a CDR H2 as set forth in SEQ ID NO:5, and a CDR H3 as set forth in SEQ ID NO:6. Optionally, the light chain variable region includes a CDR L1 as set forth in SEQ ID NO:7, a CDR L2 as set forth in SEQ ID NO:8 and a CDR L3 as set forth in SEQ ID NO:9. And the heavy chain variable region includes a CDR H1 as set forth in SEQ ID NO:10, a CDR H2 as set forth in SEQ ID NO:11, and a CDR H3 as set forth in SEQ ID NO:12. Optionally, the antibody is a humanized antibody. Also provided are functional fragments of the disclosed antibodies.

The humanized antibodies as provided herein are capable of binding a BAFF-R protein and include at least one mouse CDR or a functional fragment or variant thereof of the BAFF-R antibody provided herein (e.g., CDR L1 of SEQ ID NO:1 or 7, CDR L2 of SEQ ID NO:2 or 8, CDR L3 of SEQ ID NO:3 or 9, CDR H1 of SEQ ID NO:4 or 10, CDR H2 of SEQ ID NO:5 or 11, CDR H3 of SEQ ID NO:7 or 13). A functional fragment of a CDR is a portion of a complete CDR amino acid sequence yet the antibody or fragment thereof containing the functional fragment is still capable of binding to an antigen (e.g., BAFF-R). A functional variant of a CDR is a CDR with one or more changes to the CDR sequence yet the antibody or functional fragment thereof containing the functional variant is still capable of binding to an antigen (e.g., BAFF-R). For example, a functional variant of a nucleic acid sequence encoding a CDR can include one or more changes yet still encode the same amino acid sequence of the CDR. Further, a functional variant of a polypeptide sequence of a CDR can include one or more amino acid changes as long as the antibody or functional fragment thereof bind to the antigen. Thus, a functional fragment or variant of a CDR typically includes the amino acid residues required for antibody binding to the antigen (e.g., BAFF-R). Where a humanized antibody includes at least one CDR, the at least one CDR or a functional fragment thereof is derived from a donor antibody. Optionally, the donor antibody is a mouse antibody. A person of skill in the art will immediately recognize that a humanized antibody including at least one mouse CDR is a humanized antibody with at least one mouse CDR derived from a donor antibody and the additional CDRs are derived from the acceptor antibody (e.g. where the light chain includes a total of three CDRs and the heavy chain includes a total of three CDRs).

Where the BAFF-R antibody provided herein is a humanized antibody, the antibody may include a humanized heavy chain variable region and/or a humanized light chain variable region. Optionally, the humanized light chain variable region and the humanized heavy chain variable region include combined one mouse CDR or functional fragment or variant of a mouse CDR. Thus, the humanized light chain variable region and the humanized heavy chain variable region can include combined six CDRs wherein at least one of the six CDRs is a mouse CDR. Where the humanized light chain variable region and the humanized heavy chain variable region include combined one mouse CDR, the humanized light chain variable region or the humanized heavy chain variable region include one mouse CDR. For example, a humanized antibody may include CDR L3 derived from the donor antibody (e.g. mouse, also referred to herein as a mouse CDR L3) and CDR L1, CDR L2, CDR H1, CDR H2, and CDR H3 derived from the acceptor antibody (i.e. human).

Optionally, the humanized light chain variable region and the humanized heavy chain variable region include combined two mouse CDRs. Where the humanized light chain variable region and the humanized heavy chain variable region include combined two mouse CDRs, the humanized light chain variable region and the humanized heavy chain variable region each include one mouse CDR (i), the humanized light chain variable region includes two mouse CDRs (ii), or the humanized heavy chain variable region includes two mouse CDRs (iii). For example, a humanized antibody may include CDR L3 and CDR H3 derived from the donor antibody (also referred to herein as a mouse CDR L3 and a mouse CDR H3, respectively), and CDR L1, CDR L2, CDR H1, and CDR H2 derived from the acceptor antibody (i.e., human).

Optionally, the humanized light chain variable region and the humanized heavy chain variable region include combined three mouse CDRs. Where the humanized light chain variable region and the humanized heavy chain variable region include combined three mouse CDRs, the humanized light chain variable region may include one mouse CDR and the humanized heavy chain variable region may include two mouse CDRs (i), the humanized light chain variable region includes two mouse CDRs and the humanized heavy chain variable region includes one mouse CDR (ii), the humanized light chain variable region includes three mouse CDRs (iii), or the humanized heavy chain variable region includes three mouse CDRs (iv). For example, a humanized antibody may include CDR L3, CDR H3 and CDR L2 derived from the donor antibody (e.g. mouse, also referred to herein as a CDR L3, mouse CDR H3, and mouse CDR L2 respectively) and CDR L1, CDR H1, and CDR H2 derived from the acceptor antibody (i.e., human).

The humanized light chain variable region and the humanized heavy chain variable region can include combined four mouse CDRs. Where the humanized light chain variable region and the humanized heavy chain variable region include combined four mouse CDRs, the humanized light chain variable region includes one mouse CDR and the humanized heavy chain variable region includes three mouse CDRs (i), the humanized light chain variable region includes three mouse CDRs and the humanized heavy chain variable region includes one mouse CDR (ii), or the humanized light chain variable region includes two mouse CDRs and the humanized heavy chain variable region includes two mouse CDRs (iii). For example, a humanized antibody may include CDR L3, CDR H3, CDR L2 and CDR L1 derived from the donor antibody (e.g. mouse, also referred to herein as a mouse CDR L3, mouse CDR H3, mouse CDR L2 and mouse CDR L1 respectively) and CDR H1 and CDR H2 derived from the acceptor antibody (i.e. human).

The humanized light chain variable region and the humanized heavy chain variable region each can include at least one mouse CDR. Where the humanized light chain variable region and the humanized heavy chain variable region each include at least one mouse CDR, the humanized light chain variable region includes at least one mouse CDR and the humanized heavy chain variable region includes at least one mouse CDR. Thus, the humanized light chain variable region can include mouse CDR L1 and the humanized heavy chain includes mouse CDR H1. Optionally, mouse CDR L1 includes the amino acid sequence of SEQ ID NO:1 and mouse CDR H1 includes the amino acid sequence of SEQ ID NO:4. Optionally, mouse CDR L1 is the amino acid sequence of SEQ ID NO:1 and mouse CDR H1 is the amino acid sequence of SEQ ID NO:4. Optionally, the humanized light chain variable region includes mouse CDR L2 and the humanized heavy chain variable region includes mouse CDR H2. Optionally, mouse CDR L2 includes the amino acid sequence of SEQ ID NO:2 and mouse CDR H2 includes the amino acid sequence of SEQ ID NO:5. Optionally, mouse CDR L2 is the amino acid sequence of SEQ ID NO:2 and mouse CDR H2 is the amino acid sequence of SEQ ID NO:5. Optionally, the humanized light chain variable region includes mouse CDR L3 and the humanized heavy chain variable region includes mouse CDR H3. Optionally, mouse CDR L3 includes the amino acid sequence of SEQ ID NO:3 and mouse CDR H3 includes the amino acid sequence of SEQ ID NO:6. Optionally, CDR L3 is the amino acid sequence of SEQ ID NO:3 and mouse CDR H3 is the amino acid sequence of SEQ ID NO:6.

Optionally, mouse CDR L1 includes the amino acid sequence of SEQ ID NO:7 and mouse CDR H1 includes the amino acid sequence of SEQ ID NO:10. Optionally, mouse CDR L1 is the amino acid sequence of SEQ ID NO:7 and mouse CDR H1 is the amino acid sequence of SEQ ID NO:10. Optionally, the humanized light chain variable region includes mouse CDR L2 and the humanized heavy chain variable region includes mouse CDR H2. Optionally, mouse CDR L2 includes the amino acid sequence of SEQ ID NO:8 and mouse CDR H2 includes the amino acid sequence of SEQ ID NO:11. Optionally, mouse CDR L2 is the amino acid sequence of SEQ ID NO:8 and mouse CDR H2 is the amino acid sequence of SEQ ID NO:11. Optionally, the humanized light chain variable region includes mouse CDR L3 and the humanized heavy chain variable region includes mouse CDR H3. Optionally, mouse CDR L3 includes the amino acid sequence of SEQ ID NO:9 and mouse CDR H3 includes the amino acid sequence of SEQ ID NO:12. Optionally, CDR L3 is the amino acid sequence of SEQ ID NO:9 and mouse CDR H3 is the amino acid sequence of SEQ ID NO:12.

The presence of mouse CDR L3 and mouse CDR H3 may be sufficient for binding of a humanized antibody to BAFF-R. Thus, the humanized antibody may not include mouse CDR L1, mouse CDR L2, CDR H1 or mouse CDR H2. Where the humanized antibody does not include mouse CDR L1, mouse CDR L2, mouse CDR H1 or mouse CDR H2, the humanized antibody includes CDR L1, CDR L2, CDR H1 or CDR H2 derived from the acceptor antibody (i.e. human). Thus, a humanized antibody that does not include mouse CDR L1, mouse CDR L2, mouse CDR H1 or mouse CDR H2, does not include CDR L1, CDR L2, CDR H1 or CDR H2 from a donor antibody (e.g. mouse, rat, rabbit), but includes CDR L1, CDR L2, CDR H1 or CDR H2 from the acceptor antibody (i.e. human). Thus, the humanized light chain variable region may not include mouse CDR L1 or mouse CDR L2 and the humanized heavy chain variable region does not include mouse CDR H1 or mouse CDR H2. Optionally, the humanized light chain variable region does not include mouse CDR L1 and mouse CDR L2 and the humanized heavy chain variable region does not include mouse CDR H1 and mouse CDR H2.

Optionally, the humanized light chain variable region includes mouse CDR L2 and mouse CDR L3 and the humanized heavy chain variable region includes mouse CDR H2 and mouse CDR H3. Optionally, the humanized light chain variable region includes mouse CDR L1, mouse CDR L2 and mouse CDR L3 and the humanized heavy chain variable region includes mouse CDR H1, mouse CDR H2 and mouse CDR H3. Optionally, the humanized light chain variable region includes mouse CDR L1 as set forth in SEQ ID NO:1, mouse CDR L2 as set forth in SEQ ID NO:2 and mouse CDR L3 as set forth in SEQ ID NO:3, and the humanized heavy chain variable region includes mouse CDR H1 as set forth in SEQ ID NO:4, mouse CDR H2 as set forth in SEQ ID NO:5, and mouse CDR H3 as set forth in SEQ ID NO:6. Optionally, the humanized light chain variable region includes mouse CDR L1 as set forth in SEQ ID NO:7, mouse CDR L2 as set forth in SEQ ID NO:8 and mouse CDR L3 as set forth in SEQ ID NO:9, and the humanized heavy chain variable region includes mouse CDR H1 as set forth in SEQ ID NO:10, mouse CDR H2 as set forth in SEQ ID NO:11, and mouse CDR H3 as set forth in SEQ ID NO:12.

The position of CDRs and FRs may be defined by the Kabat numbering system (Kabat et al., Sequences of Proteins of Immunological Interest, Fifth Edition, U.S. Department of Health and Human Services, U.S. Government Printing Office (1991)). Likewise, the positions occupied by individual residues within the light or the heavy chain of an antibody may be defined by the Kabat numbering system. Therefore, the location of residues required for binding within a humanized light chain and a humanized heavy chain of a humanized antibody may be defined by the position of the residue according to the Kabat numbering system as is well known in the art. As described above, a humanized antibody may be an antibody having CDRs from a donor antibody (e.g. mouse) and variable region framework (FR) from a human antibody. The framework regions (FRs) are said to hold the CDRs in place in a humanized antibody. Proceeding from the amino-terminus, these regions are designated FR L1, FR L2, FR L3, and FR L4 for the light chain and FR H1, FR H2, FR H3, and FR H4, for the heavy chain, respectively. Provided herein are humanized antibodies that include one or more residues within the framework regions. Optionally, these residues are important for epitope binding of the humanized antibody. A framework region residue involved in (or important for) epitope binding (e.g. BAFF-R binding) is referred to herein as a binding framework region residue. The binding framework region residues may reside in the framework region of a humanized light chain variable region (i.e. FR L1, FR L2, FR L3, FR L4) or they may reside in the framework of a humanized heavy chain variable region (i.e. FR H1, FR H2, FR H3, FR H4). A binding framework residue residing in the FR L3 region of a humanized light chain is referred to herein as a FR L3 binding framework region residue. Thus, a binding framework region residue residing in the FR H3 region of a humanized heavy chain is referred to herein as a FR H3 binding framework region residue.

Optionally, the humanized antibody includes at least one binding framework region residue. Optionally, the humanized light chain variable region includes at least one binding framework region residue. Optionally, the humanized light chain variable region includes one or more FR L1, FR L2, FR L3 or FR L4 binding framework region residues. Optionally, the humanized light chain variable region includes one or more FR L1 binding framework region residues. Optionally, the humanized light chain variable region includes one or more FR L2 binding framework region residues. Optionally, the humanized light chain variable region includes one or more FR L3 binding framework region residues. Optionally, the humanized light chain variable region includes one or more FR L4 binding framework region residues. Optionally, the humanized heavy chain variable region includes one or more FR H1, FR H2, FR H3 or FR H4 binding framework region residues. Optionally, the humanized heavy chain variable region includes one or more FR H1 binding framework region residues. Optionally, the humanized heavy chain variable region includes one or more FR H2 binding framework region residues. Optionally, the humanized heavy chain variable region includes one or more FR H3 binding framework region residues. Optionally, the humanized heavy chain variable region includes one or more FR H4 binding framework region residues.

The humanized light chain variable region can include at least one binding framework region residue (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49, 50 or more residues) and the humanized heavy chain variable region includes at least one binding framework region residue (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49, 50 or more residues). The position of a binding framework region residue within a humanized antibody may be defined by the Kabat numbering system similar to the positions of CDR residues.

Optionally, the light chain variable region includes a serine at a position corresponding to Kabat position 7. Optionally, the light chain variable region includes a proline at a position corresponding to Kabat position 8. Optionally, the light chain variable region includes a valine at a position corresponding to Kabat position 15. Optionally, the light chain variable region includes a threonine at a position corresponding to Kabat position 22. Optionally, the light chain variable region includes a glutamine at a position corresponding to Kabat position 24. Optionally, the light chain variable region includes a glycine at a position corresponding to Kabat position 41. Optionally, the light chain variable region includes a lysine at a position corresponding to Kabat position 42. Optionally, the light chain variable region includes an alanine at a position corresponding to Kabat position 43. Optionally, the light chain variable region includes a proline at a position corresponding to Kabat position 44. Optionally, the light chain variable region includes a threonine at a position corresponding to Kabat position 56. Optionally, the light chain variable region includes a threonine at a position corresponding to Kabat position 72. Optionally, the light chain variable region includes a phenylalanine at a position corresponding to Kabat position 73. Optionally, the light chain variable region includes a glutamine at a position corresponding to Kabat position 79. Optionally, the light chain variable region includes a valine at a position corresponding to Kabat position 104.

Optionally, the light chain variable region includes a serine at a position corresponding to Kabat position 7, a proline at a position corresponding to Kabat position 8, a valine at a position corresponding to Kabat position 15, a threonine at a position corresponding to Kabat position 22, a glutamine or a serine at a position corresponding to Kabat position 24, a glycine at a position corresponding to Kabat position 41, a lysine at a position corresponding to Kabat position 42, an alanine or a threonine at a position corresponding to Kabat position 43, a proline at a position corresponding to Kabat position 44, a threonine at a position corresponding to Kabat position 56, a threonine at a position corresponding to Kabat position 72, a phenylalanine or a lysine at a position corresponding to Kabat position 73, a glutamine at a position corresponding to Kabat position 79 or a valine at a position corresponding to Kabat position 104.

Optionally, the light chain variable region includes a serine at a position corresponding to Kabat position 7, a proline at a position corresponding to Kabat position 8, a valine at a position corresponding to Kabat position 15, a threonine at a position corresponding to Kabat position 22, a glutamine or a serine at a position corresponding to Kabat position 24, a glycine at a position corresponding to Kabat position 41, a lysine at a position corresponding to Kabat position 42, an alanine or a threonine at a position corresponding to Kabat position 43, a proline at a position corresponding to Kabat position 44, a threonine at a position corresponding to Kabat position 56, a threonine at a position corresponding to Kabat position 72, a phenylalanine or a lysine at a position corresponding to Kabat position 73, a glutamine at a position corresponding to Kabat position 79 and a valine at a position corresponding to Kabat position 104.

Optionally, the light chain variable region includes a binding framework region residue that is a serine at a position corresponding to Kabat position 7, a proline at a position corresponding to Kabat position 8, a valine at a position corresponding to Kabat position 15, a threonine at a position corresponding to Kabat position 22, a glutamine or a serine at a position corresponding to Kabat position 24, a glycine at a position corresponding to Kabat position 41, a lysine at a position corresponding to Kabat position 42, an alanine or a threonine at a position corresponding to Kabat position 43, a proline at a position corresponding to Kabat position 44, a threonine at a position corresponding to Kabat position 56, a threonine at a position corresponding to Kabat position 72, a phenylalanine or a lysine at a position corresponding to Kabat position 73, a glutamine at a position corresponding to Kabat position 79 or a valine at a position corresponding to Kabat position 104.

Optionally, the heavy chain variable region includes a threonine or an alanine at a position corresponding to Kabat position 10. Optionally, the heavy chain variable region includes a lysine at a position corresponding to Kabat position 11. Optionally, the heavy chain variable region includes a valine at a position corresponding to Kabat position 12. Optionally, the heavy chain variable region includes a threonine at a position corresponding to Kabat position 15. Optionally, the heavy chain variable region includes a threonine at a position corresponding to Kabat position 19. Optionally, the heavy chain variable region includes a threonine at a position corresponding to Kabat position 23. Optionally, the heavy chain variable region includes a proline at a position corresponding to Kabat position 41. Optionally, the heavy chain variable region includes an alanine at a position corresponding to Kabat position 44. Optionally, the heavy chain variable region includes a proline or a threonine at a position corresponding to Kabat position 61. Optionally, the heavy chain variable region includes an arginine at a position corresponding to Kabat position 66. Optionally, the heavy chain variable region includes a threonine at a position corresponding to Kabat position 70. Optionally, the heavy chain variable region includes a lysine at a position corresponding to Kabat position 75. Optionally, the heavy chain variable region includes a valine at a position corresponding to Kabat position 79. Optionally, the heavy chain variable region includes a threonine at a position corresponding to Kabat position 81. Optionally, the heavy chain variable region includes a methionine at a position corresponding to Kabat position 82. Optionally, the heavy chain variable region includes an asparagine at a position corresponding to Kabat position 82B. Optionally, the heavy chain variable region includes a methionine at a position corresponding to Kabat position 82C. Optionally, the heavy chain variable region includes a proline at a position corresponding to Kabat position 84. Optionally, the heavy chain variable region includes a valine at a position corresponding to Kabat position 85. Optionally, the heavy chain variable region includes a lysine at a position corresponding to Kabat position 108. Optionally, the heavy chain variable region includes a valine at a position corresponding to Kabat position 109.

Optionally, the heavy chain variable region includes a threonine or an alanine at a position corresponding to Kabat position 10, a lysine at a position corresponding to Kabat position 11, a valine at a position corresponding to Kabat position 12, a threonine at a position corresponding to Kabat position 15, a threonine at a position corresponding to Kabat position 19, a threonine at a position corresponding to Kabat position 23, a proline at a position corresponding to Kabat position 41, an alanine at a position corresponding to Kabat position 44, a proline, a serine or a threonine at a position corresponding to Kabat position 61, an arginine at a position corresponding to Kabat position 66, a threonine at a position corresponding to Kabat position 70, a lysine at a position corresponding to Kabat position 75, a valine at a position corresponding to Kabat position 79, a threonine or a lysine at a position corresponding to Kabat position 81, a methionine at a position corresponding to Kabat position 82, an asparagine at a position corresponding to Kabat position 82B, a methionine at a position corresponding to Kabat position 82C, a proline at a position corresponding to Kabat position 84, a valine at a position corresponding to Kabat position 85, a lysine at a position corresponding to Kabat position 108 or a valine at a position corresponding to Kabat position 109.

Optionally, the heavy chain variable region includes a threonine or an alanine at a position corresponding to Kabat position 10, a lysine at a position corresponding to Kabat position 11, a valine at a position corresponding to Kabat position 12, a threonine at a position corresponding to Kabat position 15, a threonine at a position corresponding to Kabat position 19, a threonine at a position corresponding to Kabat position 23, a proline at a position corresponding to Kabat position 41, an alanine at a position corresponding to Kabat position 44, a proline, a serine or a threonine at a position corresponding to Kabat position 61, an arginine at a position corresponding to Kabat position 66, a threonine at a position corresponding to Kabat position 70, a lysine at a position corresponding to Kabat position 75, a valine at a position corresponding to Kabat position 79, a threonine or a lysine at a position corresponding to Kabat position 81, a methionine at a position corresponding to Kabat position 82, an asparagine at a position corresponding to Kabat position 82B, a methionine at a position corresponding to Kabat position 82C, a proline at a position corresponding to Kabat position 84, a valine at a position corresponding to Kabat position 85, a lysine at a position corresponding to Kabat position 108 and a valine at a position corresponding to Kabat position 109.

Optionally, the heavy chain variable region includes a binding framework region residue that is a threonine or an alanine at a position corresponding to Kabat position 10, a lysine at a position corresponding to Kabat position 11, a valine at a position corresponding to Kabat position 12, a threonine at a position corresponding to Kabat position 15, a threonine at a position corresponding to Kabat position 19, a threonine at a position corresponding to Kabat position 23, a proline at a position corresponding to Kabat position 41, an alanine at a position corresponding to Kabat position 44, a proline, a serine or a threonine at a position corresponding to Kabat position 61, an arginine at a position corresponding to Kabat position 66, a threonine at a position corresponding to Kabat position 70, a lysine at a position corresponding to Kabat position 75, a valine at a position corresponding to Kabat position 79, a threonine or a lysine at a position corresponding to Kabat position 81, a methionine at a position corresponding to Kabat position 82, an asparagine at a position corresponding to Kabat position 82B, a methionine at a position corresponding to Kabat position 82C, a proline at a position corresponding to Kabat position 84, a valine at a position corresponding to Kabat position 85, a lysine at a position corresponding to Kabat position 108 or a valine at a position corresponding to Kabat position 109.

Provided is a humanized BAFF-R antibody including a humanized light chain variable region including a mouse CDR L1, mouse CDR L2, or mouse CDR L3 and a humanized heavy chain variable region including a mouse CDR H1, mouse CDR H2, or mouse CDR H3. The humanized light chain variable region may include a mouse CDR L1 as set forth in SEQ ID NO:1, a mouse CDR L2 as set forth in SEQ ID NO:2, or a mouse CDR L3 as set forth in SEQ ID NO:3. The humanized light chain variable region may include a mouse CDR L1 as set forth in SEQ ID NO:1, a mouse CDR L2 as set forth in SEQ ID NO:2, and a mouse CDR L3 as set forth in SEQ ID NO:3. The humanized heavy chain variable region may include a mouse CDR H1 as set forth in SEQ ID NO:4, a mouse CDR H2 as set forth in SEQ ID NO:5, or a mouse CDR H3 as set forth in SEQ ID NO:6. The humanized heavy chain variable region may include a mouse CDR H1 as set forth in SEQ ID NO:4, a mouse CDR H2 as set forth in SEQ ID NO:5, and a mouse CDR H3 as set forth in SEQ ID NO:6. Optionally, the humanized light chain variable region includes a mouse CDR L1 as set forth in SEQ ID NO:1. Optionally, the humanized light chain variable region includes a mouse CDR L2 as set forth in SEQ ID NO:2. Optionally, the humanized light chain variable region includes a mouse CDR L3 as set forth in SEQ ID NO:3. Optionally, the humanized heavy chain variable region includes a mouse CDR H1 as set forth in SEQ ID NO:4. Optionally, the humanized heavy chain variable region includes a mouse CDR H2 as set forth in SEQ ID NO:5. Optionally, the humanized light chain variable region includes a mouse CDR H3 as set forth in SEQ ID NO:6. In further embodiments, the humanized light chain variable region includes at least one binding framework region residue. In other further embodiments, the humanized heavy chain variable region includes at least one binding framework region residue.

Provided is a humanized BAFF-R antibody including a humanized light chain variable region including a mouse CDR L1, mouse CDR L2, or mouse CDR L3 and a humanized heavy chain variable region including a mouse CDR H1, mouse CDR H2, or mouse CDR H3. The humanized light chain variable region may include a mouse CDR L1 as set forth in SEQ ID NO:7, a mouse CDR L2 as set forth in SEQ ID NO:8, or a mouse CDR L3 as set forth in SEQ ID NO:9. The humanized light chain variable region may include a mouse CDR L1 as set forth in SEQ ID NO:7, a mouse CDR L2 as set forth in SEQ ID NO:8, and a mouse CDR L3 as set forth in SEQ ID NO:9. The humanized heavy chain variable region may include a mouse CDR H1 as set forth in SEQ ID NO:10, a mouse CDR H2 as set forth in SEQ ID NO:11, or a mouse CDR H3 as set forth in SEQ ID NO:12. The humanized heavy chain variable region may include a mouse CDR H1 as set forth in SEQ ID NO:10, a mouse CDR H2 as set forth in SEQ ID NO:11, and a mouse CDR H3 as set forth in SEQ ID NO:12. Optionally, the humanized light chain variable region includes a mouse CDR L1 as set forth in SEQ ID NO:7. Optionally, the humanized light chain variable region includes a mouse CDR L2 as set forth in SEQ ID NO:8. Optionally, the humanized light chain variable region includes a mouse CDR L3 as set forth in SEQ ID NO:9. Optionally, the humanized heavy chain variable region includes a mouse CDR H1 as set forth in SEQ ID NO:10. Optionally, the humanized heavy chain variable region includes a mouse CDR H2 as set forth in SEQ ID NO:11. Optionally, the humanized light chain variable region includes a mouse CDR H3 as set forth in SEQ ID NO:12. In further embodiments, the humanized light chain variable region includes at least one binding framework region residue. In other further embodiments, the humanized heavy chain variable region includes at least one binding framework region residue.

Optionally, the light chain variable region includes the sequence of SEQ ID NO:18, SEQ ID NO:20 or SEQ ID NO:22. Optionally, the light chain variable region includes the sequence of SEQ ID NO:18. Optionally, the light chain variable region includes the sequence of SEQ ID NO:20. Optionally, the light chain variable region includes the sequence of SEQ ID NO:22. Optionally, the light chain variable region is the sequence of SEQ ID NO:18. Optionally, the light chain variable region is the sequence of SEQ ID NO:20. Optionally, the light chain variable region is the sequence of SEQ ID NO:22. Optionally, the heavy chain variable region includes the sequence of SEQ ID NO:24, SEQ ID NO:26 or SEQ ID NO:28. Optionally, the heavy chain variable region includes the sequence of SEQ ID NO:24. Optionally, the heavy chain variable region includes the sequence of SEQ ID NO:26. Optionally, the heavy chain variable region includes the sequence of SEQ ID NO:28. Optionally, the heavy chain variable region is the sequence of SEQ ID NO:24. Optionally, the heavy chain variable region is the sequence of SEQ ID NO:26. Optionally, the heavy chain variable region is the sequence of SEQ ID NO:28. Thus, in another aspect, provided is a humanized BAFF-R antibody including a humanized light chain variable region and a humanized heavy chain variable region, wherein the humanized light chain variable region includes the sequence of SEQ ID NO:18 and the heavy chain variable region includes the sequence of SEQ ID NO:24. In another aspect, provided is a humanized BAFF-R antibody including a humanized light chain variable region and a humanized heavy chain variable region, wherein the humanized light chain variable region includes the sequence of SEQ ID NO:20 and the heavy chain variable region includes the sequence of SEQ ID NO:26. In another aspect, provided is a humanized BAFF-R antibody including a humanized light chain variable region and a humanized heavy chain variable region, wherein the humanized light chain variable region includes the sequence of SEQ ID NO:22 and the heavy chain variable region includes the sequence of SEQ ID NO:28.

Optionally, the antibody is a chimeric antibody. Optionally, the light chain variable region includes the sequence of SEQ ID NO:14. Optionally, the heavy chain variable region includes the sequence of SEQ ID NO:16. Optionally, the light chain variable region is the sequence of SEQ ID NO:14. Optionally, the heavy chain variable region is the sequence of SEQ ID NO:16. Thus, in another aspect, provided is a chimeric BAFF-R antibody including a light chain variable region and a heavy chain variable region, wherein the light chain variable region includes the sequence of SEQ ID NO:14 and the heavy chain variable region includes the sequence of SEQ ID NO:16.

Optionally, the light chain variable region includes the sequence of SEQ ID NO:30. Optionally, the heavy chain variable region includes the sequence of SEQ ID NO:32. Optionally, the light chain variable region is the sequence of SEQ ID NO:30. Optionally, the heavy chain variable region is the sequence of SEQ ID NO:32. Thus, in another aspect, provided is a chimeric BAFF-R antibody including a light chain variable region and a heavy chain variable region, wherein the light chain variable region includes the sequence of SEQ ID NO:30 and the heavy chain variable region includes the sequence of SEQ ID NO:32.

In each case where an antibody is recited herein a functional fragment can be used. Thus, for example, provided are Fab' fragments can include a heavy chain (e.g. including a constant and a variable region) and a light chain (e.g. including a constant and a variable region). Optionally, the Fab' fragment includes a humanized heavy chain (e.g. including a constant and a variable region) and a humanized light chain (e.g. including a constant and a variable region).

Optionally, the BAFF-R antibody or fragment thereof includes a human constant region. Optionally, the BAFF-R antibody or fragment thereof is an IgG. Optionally, the BAFF-R antibody or fragment thereof is an IgG1. Optionally, the BAFF-R antibody or fragment thereof is an IgG2. Optionally, the BAFF-R antibody or fragment thereof is an IgG3. Optionally, the BAFF-R antibody or fragment thereof is an IgG4. Optionally, the BAFF-R antibody or fragment thereof is an IgA. Optionally, the BAFF-R antibody or fragment thereof is an IgM.

Optionally, the BAFF-R antibody or fragment thereof is a single chain antibody. A single chain antibody includes a variable light chain and a variable heavy chain. A person of skill in the art will immediately recognize that a single chain antibody includes a single light chain and a single heavy chain, in contrast to an immunoglobulin antibody, which includes two identical pairs of polypeptide chains, each pair having one light chain and one heavy chain. Each light chain and heavy chain in turn consists of two regions: a variable ("V") region (i.e. variable light chain and variable heavy chain) involved in binding the target antigen, and a constant ("C") region that interacts with other components of the immune system. The variable light chain and the variable heavy chain in a single chain antibody may be linked through a linker peptide. Examples for linker peptides of single chain antibodies are described in Bird, R. E., et al., Science. 242(4877):423-6 (1988). Methods of making scFv antibodies have been described. See, Huse et al., *Science* 246:1275-1281 (1989); Ward et al., *Nature* 341:544-546 (1989); and Vaughan et al., *Nature Biotech.* 14:309-314 (1996). Briefly, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell.

The ability of an antibody or functional fragment thereof to bind a specific epitope (e.g., BAFF-R) can be described by the equilibrium dissociation constant ($K_D$). The equilibrium dissociation constant ($K_D$) as defined herein is the ratio of the dissociation rate (K-off) and the association rate (K-on) of a BAFF-R antibody to a BAFF-R protein. It is described by the following formula: $K_D$=K-off/K-on. Optionally, the BAFF-R antibody is capable of binding a BAFF-R protein with an equilibrium dissociation constant ($K_D$) of less than about 5 nM. Optionally, the BAFF-R antibody is capable of binding a BAFF-R protein with an equilibrium dissociation constant ($K_D$) of less than about 4.5 nM. Optionally, the BAFF-R antibody is capable of binding a BAFF-R protein with an equilibrium dissociation constant ($K_D$) of less than about 4 nM. Optionally, the BAFF-R antibody is capable of binding a BAFF-R protein with an equilibrium dissociation constant ($K_D$) of less than about 3.5 nM. Optionally, the BAFF-R antibody is capable of binding a BAFF-R protein with an equilibrium dissociation constant ($K_D$) of less than about 3 nM. Optionally, the BAFF-R antibody is capable of binding a BAFF-R protein with an equilibrium dissociation constant ($K_D$) of less than about 2.5 nM. Optionally, the BAFF-R antibody is capable of binding a BAFF-R protein with an equilibrium dissociation constant ($K_D$) of less than about 2 nM. Optionally, the BAFF-R antibody is capable of binding a BAFF-R protein with an equilibrium dissociation constant ($K_D$) of less than about 1.5 nM. Optionally, the BAFF-R antibody is capable of binding a BAFF-R protein with an equilibrium dissociation constant ($K_D$) of less than about 1 nM. Optionally, the BAFF-R antibody is capable of binding a BAFF-R protein with an equilibrium dissociation constant ($K_D$) of less than about 0.5 nM.

Optionally, the BAFF-R antibody or functional fragment thereof is capable of binding a BAFF-R protein with an equilibrium dissociation constant ($K_D$) of about 0.5 nM. Optionally, the BAFF-R antibody or functional fragment thereof is capable of binding a BAFF-R protein with an equilibrium dissociation constant ($K_D$) of about 1 nM. Optionally, the BAFF-R antibody or functional fragment thereof is capable of binding a BAFF-R protein with an equilibrium dissociation constant ($K_D$) of about 1.5 nM. Optionally, the BAFF-R antibody or functional fragment thereof is capable of binding a BAFF-R protein with an equilibrium dissociation constant ($K_D$) of about 2 nM. Optionally, the BAFF-R antibody or functional fragment thereof is capable of binding a BAFF-R protein with an equilibrium dissociation constant ($K_D$) of about 2.5 nM. Optionally, the BAFF-R antibody or functional fragment thereof is capable of binding a BAFF-R protein with an equilibrium dissociation constant ($K_D$) of about 3 nM. Optionally, the BAFF-R antibody or functional fragment thereof is capable of binding a BAFF-R protein with an equilibrium dissociation constant ($K_D$) of about 3.5 nM. Optionally, the BAFF-R antibody or functional fragment thereof is capable of binding a BAFF-R protein with an equilibrium dissociation constant ($K_D$) of about 4 nM. Optionally, the BAFF-R antibody or functional fragment thereof is capable of binding a BAFF-R protein with an equilibrium dissociation constant ($K_D$) of about 4.5 nM. Optionally, the BAFF-R antibody or functional fragment thereof is capable of binding a BAFF-R protein with an equilibrium dissociation constant ($K_D$) of about 5 nM. Optionally, the BAFF-R antibody or functional fragment thereof is capable of binding a BAFF-R protein with an equilibrium dissociation constant ($K_D$) of about 0.5, 1, 1.5, 2, 2.5, 3, 3.5, 4, 4.5, or 5 nM.

Optionally, the provided humanized B cell activating factor receptor (BAFF-R) antibody is capable of binding BAFF-R with a $K_D$ of less than about 4 nM is provided. Optionally, the humanized B cell activating factor receptor (BAFF-R) antibody bound to a BAFF-R at a $K_D$ of less than about 4 nM is provided. Optionally, the antibody does not induce BAFF-R activity.

Optionally, the BAFF-R antibody is bound to a BAFF-R protein. Optionally, the BAFF-R protein is a human BAFF-R protein. Optionally, the BAFF-R protein is encoded by a nucleic acid sequence identified by NCBI Gene ID number 115650. Optionally, the BAFF-R protein forms part of a cell. Optionally, the BAFF-R protein is expressed on the surface of said cell. Optionally, the cell is a lymphoid cell. Optionally, the cell is a B cell. Optionally, the cell is a cancer cell. Optionally, the cancer cell is a lymphoma cell.

A large variety of diagnostic and therapeutic moieties and combinations thereof may be conjugated to the BAFF-R antibody or functional fragment thereof provided herein including embodiments thereof, thereby, providing for highly stable and/or versatile drug delivery and/or diagnostic compositions. Optionally, the BAFF-R antibody or functional fragment thereof includes a therapeutic moiety or a diagnostic moiety. Optionally, the therapeutic moiety or the diagnostic moiety is bound to the BAFF-R antibody or functional fragment thereof through a chemical linker. Optionally, the chemical linker is a covalent linker or a non-covalent linker. Techniques for conjugating therapeutic moieties to antibodies are well known (see, e.g., Arnon et al., Monoclonal Antibodies For Immunotargeting Of Drugs In Cancer Therapy, in Monoclonal Antibodies And Cancer Therapy, Reisfeld et al. (eds.), pp. 243-56 (Alan R. Liss, Inc. 1985); Hellstrom et al., Antibodies For Drug Delivery in Controlled Drug Delivery ($2^{nd}$ Ed.), Robinson et al. (eds.), pp. 623-53 (Marcel Dekker, Inc. 1987); Thorpe, Antibody Carriers Of Cytotoxic Agents In Cancer Therapy: A Review in Monoclonal Antibodies '84: Biological And Clinical Applications, Pinchera et al. (eds.), pp. 475-506 (1985); and Thorpe et al., The Preparation And Cytotoxic Properties Of Antibody-Toxin Conjugates, Immunol. Rev., 62:119-58 (1982)). As used herein, the term antibody-drug conjugate or ADC refers to a therapeutic moiety conjugated or otherwise covalently bound to an antibody or functional fragment thereof.

The term therapeutic moiety as provided herein is used in accordance with its plain ordinary meaning and refers to a monovalent compound having a therapeutic benefit (e.g., prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphtheria toxin, Pseudomonas exotoxin (PE) A, PE40, abrin, and glucocorticoid. Optionally, the therapeutic moiety is an anti-cancer agent or chemotherapeutic agent as described herein. Optionally, the therapeutic moiety is a nucleic acid moiety, a peptide moiety or a small molecule drug moiety. Optionally, the therapeutic moiety is a nucleic acid moiety. Optionally, the therapeutic moiety is an antibody moiety. Optionally, the therapeutic moiety is a peptide moiety. Optionally, the therapeutic moiety is a small molecule drug moiety. Optionally, the therapeutic moiety is a nuclease. Optionally, the therapeutic moiety is an immunostimulator. Optionally, the therapeutic moiety is a toxin. Optionally, the therapeutic moiety is a nuclease.

Also provided herein are chimeric antigen receptors (CAR) including an antibody provided herein or a functional fragment thereof.

An isolated nucleic acid encoding a BAFF-R antibody or functional fragment thereof provided herein including embodiments thereof is provided. The BAFF-R antibody or functional fragment thereof encoded by the isolated nucleic acid is described in detail throughout this application (including the description above and in the examples section). For example, the nucleic acid may encode at least one CDR, specific residues involved in binding the epitope, or binding framework residues. For instance, the nucleic acid may encode a light chain including a sequence of SEQ ID NO:1.

Optionally, the isolated nucleic acid includes the sequence of SEQ ID NO:13, SEQ ID NO:15, SEQ ID NO:29 or SEQ ID NO:31. Optionally, the isolated nucleic acid includes the sequence of SEQ ID NO:13 and the sequence of SEQ ID NO:15. Optionally, the isolated nucleic acid includes the sequence of SEQ ID NO:29 and the sequence of SEQ ID NO:31.

Optionally, the isolated nucleic acid includes the sequence of SEQ ID NO:17, SEQ ID NO:19, SEQ ID NO:21, SEQ ID NO:23, SEQ ID NO:25, or SEQ ID NO:27. Optionally, the isolated nucleic acid includes the sequence of SEQ ID NO:17 and the sequence of SEQ ID NO:23. Optionally, the isolated nucleic acid includes the sequence of SEQ ID NO:19 and the sequence of SEQ ID NO:25. Optionally, the isolated nucleic acid includes the sequence of SEQ ID NO:21 and the sequence of SEQ ID NO:27.

A pharmaceutical composition including a therapeutically effective amount of a BAFF-R antibody or functional fragment thereof provided herein and a pharmaceutically acceptable excipient is provided.

A therapeutically effective amount as provided herein refers to an amount effective to achieve its intended purpose. The actual amount effective for a particular application will depend, inter alia, on the condition being treated. When administered in methods to treat a disease, the pharmaceutical compositions described herein will contain an amount of active humanized antibody effective to achieve the desired result, e.g., modulating the activity of a target molecule (e.g., BAFF-R), and/or reducing, eliminating, or slowing the progression of disease symptoms (e.g., cancer, autoimmune disease). Determination of a therapeutically effective amount of a BAFF-R antibody provided herein is well within the capabilities of those skilled in the art, especially in light of the detailed disclosure herein.

Acceptable carriers, excipients or stabilizers are nontoxic to recipients at the dosages and concentrations employed, and include buffers such as phosphate, citrate, or acetate at a pH typically of 5.0 to 8.0, optionally 6.0 to 7.0; salts such as sodium chloride, potassium chloride, and the like to make isotonic; antioxidants; preservatives; low molecular weight polypeptides; proteins; hydrophilic polymers such as polysorbate 80; amino acids such as glycine; carbohydrates; chelating agents; sugars; and other standard ingredients known to those skilled in the art (*Remington: The Science and Practice of Pharmacy, 22nd Edition*, Loyd V. Allen et al., editors, Pharmaceutical Press (2012)). The mAb can be present at a concentration of 0.1-100 mg/ml, e.g., 1-10 mg/ml or 10-50 mg/ml, for example 5, 10, 20, 30, 40, 50 or 60 mg/ml.

A pharmaceutical composition including an antibody, e.g., a humanized antibody, or a functional fragment thereof as described herein can be administered by a variety of methods known in the art. The route and/or mode of administration vary depending upon the desired results. Optionally, administration is intravenous, intramuscular, intraperitoneal, or subcutaneous, or administered proximal to the site of the target. Pharmaceutically acceptable excipients can be suitable for intravenous, intramuscular, subcutaneous, parenteral, spinal or epidermal administration (e.g., by injection or infusion).

Pharmaceutical compositions of the antibody or functional fragment thereof can be prepared in accordance with methods well known and routinely practiced in the art. See, e.g., *Remington: The Science and Practice of Pharmacy, 22nd Edition*, Loyd V. Allen et al., editors, Pharmaceutical Press (2012); and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the humanized antibody is employed in the pharmaceutical compositions. The humanized antibodies provided can be formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It may be advantageous to formulate the humanized antibodies in combination with other therapies or agents. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of humanized antibody calculated to produce the desired therapeutic effect in association with the required pharmaceutical excipient.

Actual dosage levels of the active ingredients in the pharmaceutical compositions can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies or functional fragments thereof employed in the pharmaceutical composition at levels lower than that required to achieve the desired therapeutic effect and gradually increase the dosage until the desired effect is achieved. In general, effective doses of the compositions may vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two or three weeks or once a month or once every 3 to 6 months.

The BAFF-R antibody or functional fragment thereof provided herein can be administered on multiple occasions. Intervals between single dosages can be weekly, monthly or yearly. Intervals can also be irregular as indicated by measuring blood levels of the humanized antibody in the patient. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, humanized antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Mouse fibroblast cells expressing a human BAFF-R protein or fragment thereof are provided and the human BAFF-R protein or fragment thereof is expressed on the cell surface of the cell. Optionally, the human BAFF-R protein or fragment thereof includes a detectable moiety. Optionally, the detectable moiety is a fluorescent moiety. Optionally, the detectable moiety is an enhanced green fluorescent protein (eGFP).

Methods of treating cancer in a subject in need thereof are provided. The method includes administering to a subject a therapeutically effective amount of a chimeric antigen receptor provided herein, thereby treating cancer in the subject.

In another aspect, a method of treating cancer in a subject in need thereof is provided including administering to a subject a therapeutically effective amount of an antibody or funcationl fragment thereof provided herein, thereby treating cancer in the subject. Optionally, the cancer is lymphoma, leukemia or myeloma. Optionally, the cancer is lymphoma. Optionally, the lymphoma is mantle cell lymphoma, follicular lymphoma, diffuse large B-cell lymphoma, marginal zone lymphoma or Burkitt's lymphoma. Optionally, the lymphoma is mantle cell lymphoma. Optionally, the lymphoma is follicular lymphoma. Optionally, the lymphoma is diffuse large B-cell lymphoma. Optionally, the lymphoma is marginal zone lymphoma. Optionally, the lymphoma is Burkitt's lymphoma.

Optionally, the cancer is leukemia. Optionally, the leukemia is lymphoblastic leukemia, chronic lymphocytic leukemia or hairy cell leukemia. Optionally, the leukemia is lymphoblastic leukemia. Optionally, the leukemia is chronic lymphocytic leukemia. Optionally, the leukemia is hairy cell leukemia.

Optionally, the cancer is myeloma. Optionally, the myeloma is multiple myeloma.

Optionally, the method further includes administering to the subject a second therapeutic agent. Optionally, the therapeutic agent is a chimeric monoclonal antibody capable of binding a CD 20 antigen. Optionally, the therapeutic agent is rituximab. The term "rituximab" refers in a customary sense to the monoclonal antibody against the protein CD20 identified by the ATC code L01XC02.

Also provided are methods of treating an autoimmune disease in a subject in need thereof. The method includes administering to the subject a therapeutically effective amount of an antibody or functional fragment thereof as provided herein, thereby treating an autoimmune disease in the subject. Optionally, the autoimmune disease is rheumatoid arthritis, systemic Lupus erythematosus, multiple sclerosis, glomerulonephritis, Sjögren's Syndrome or autoimmune hemolytic anemia. Optionally, the autoimmune disease is rheumatoid arthritis. Optionally, the autoimmune disease is systemic Lupus erythematosus. Optionally, the autoimmune disease is multiple sclerosis. Optionally, the autoimmune disease is glomerulonephritis. Optionally, the autoimmune disease is Sjögren's Syndrome. Optionally, the autoimmune disease is autoimmune hemolytic anemia. Optionally, the method further includes administering to the subject a second therapeutic agent.

In another aspect, a method of inhibiting proliferation of a cell is provided. The method includes contacting a cell with a BAFF-R antibody or functional fragment thereof as provided herein including embodiments thereof, thereby forming a contacted cell. The BAFF-R antibody or functional fragment thereof is allowed to bind a BAFF-R protein on the contacted cell, thereby inhibiting proliferation of the cell. Optionally, the cell is a lymphoid cell. Optionally, the cell is a B cell. Optionally, the cell is a cancer cell. Optionally, the cell is a lymphoma cell.

In another aspect, a method of producing an anti-human BAFF-R antibody is provided. The method includes administering a mouse fibroblast cell as provided herein to a mouse, thereby forming an immunized BAFF-R mouse. A splenic cell from the immunized BAFF-R mouse is fused with a human myeloma cell, thereby forming a BAFF-R hybridoma cell. The BAFF-R hybridoma cell is then allowed to express a BAFF-R antibody, thereby producing an anti-BAFF-R antibody. Optionally, the anti-BAFF-R antibody is an antibody as provided herein.

While various embodiments and aspects are shown and described herein, it will be obvious to those skilled in the art that such embodiments and aspects are provided by way of example only. Numerous variations, changes, and substitutions will now occur to those skilled in the art. It should be understood that various alternatives to the embodiments described herein may be employed.

Antibodies are large, complex molecules (molecular weight of ~150,000 Da or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site (paratope), which docks onto the target antigen (epitope). The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The term antibody is used according to its commonly known meaning in the art. Antibodies exist, e.g., as intact immunoglobulins. However, a functional antibody fragment or fragments can be used whenever the terms antibody or antibodies are recited herein. For example, a number of well-characterized functional antibody fragments can be produced by digestion with various peptidases. Thus, for example, pepsin digests an antibody below the disulfide linkages in the hinge region to produce F(ab)'2, a dimer of Fab which itself is a light chain joined to $V_H$-$C_{H1}$ by a disulfide bond. The F(ab)'2 may be reduced under mild conditions to break the disulfide linkage in the hinge region, thereby converting the F(ab)'$_2$ dimer into a Fab' monomer. The Fab' monomer is essentially a Fab with part of the hinge region (see Fundamental Immunology (Paul ed., 3d ed. (1993)). While various antibody fragments are defined in terms of the digestion of an intact antibody, one of skill will appreciate that such fragments may be synthesized de novo either chemically or by using recombinant DNA methodology. Thus, the term antibody, as used herein, is exemplary and antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)) can be used as described for antibodies.

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). Monoclonal antibodies (mAb) refer to antibodies derived from a single clone. Techniques for the production of single chain antibodies (U.S. Pat. No. 4,946,778) can be adapted to produce antibodies to polypeptides described herein. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A ligand refers to an agent, e.g., a polypeptide or other molecule, capable of binding to a receptor molecule (e.g., an antibody).

A label or a detectable moiety is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

Contacting is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term contacting may include allowing two species to react, interact, or physically touch, wherein the two species may be, for example, an antibody as described herein and a BAFF-R protein. Contacting includes, for example, allowing a humanized antibody as described herein to interact with BAFF-R.

As used herein, treating or treatment of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. Treating can also mean prolonging survival of a subject beyond that expected in the absence of treatment. Treating can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms polypeptide, peptide, and protein are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A fusion protein refers to a chimeric protein encoding two or more separate protein sequences that are recombinantly expressed as a single moiety. The term peptidyl and peptidyl moiety means a monovalent peptide.

The term amino acid refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms non-naturally occurring amino acid and unnatural amino acid refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Conservatively modified variants applies to both amino acid and nucleic acid sequences. With respect to particular nucleic acid sequences, conservatively modified variants refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Percentage of sequence identity is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms identical or percent identity in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences or individual domains of the polypeptides), when compared and aligned for maximum correspondence over a comparison window, or designated region as measured using one of the following sequence comparison algorithms or by manual alignment and visual inspection. Such sequences are then said to be substantially identical. This definition also refers to the complement of a test sequence. Optionally, the identity exists over a region that is at least about 50 nucleotides in length, or more preferably over a region that is 100 to 500 or 1000 or more nucleotides in length. The present description includes polypeptides that are substantially identical to any of SEQ ID NOs:30-51.

For sequence comparison, typically one sequence acts as a reference sequence, to which test sequences are compared.

When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A comparison window, as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid residue in an antibody corresponds to a given residue when it occupies the same essential structural position within the antibody as the given residue. For example, a selected residue in a comparison antibody corresponds to position 48 (according to the Kabat numbering system as described herein) in an antibody provided herein when the selected residue occupies the same essential spatial or structural relationship to Kabat position 48 as assessed using applicable methods in the art. For example, a comparison antibody may be aligned for maximum sequence homology with the antibody provided herein and the position in the aligned comparison antibody that aligns with Kabat position 48 may be determined to correspond to it. Alternatively, instead of (or in addition to) a primary sequence alignment as described above, a three dimensional structural alignment can also be used, e.g., where the structure of the comparison antibody is aligned for maximum correspondence with an antibody provided herein and the overall structures compared. In this case, an amino acid that occupies the same essential position as Kabat position 48 in the structural model may be said to correspond.

The term isolated, when applied to a protein, denotes that the protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term purified denotes that a protein gives rise to essentially one band in an electrophoretic gel. Particularly, it means that the protein is at least 85% pure, more preferably at least 95% pure, and most preferably at least 99% pure.

The phrase specifically (or selectively) binds to an antibody or specifically (or selectively) immunoreactive with, when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

A cell, as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

As defined herein, the term inhibition, inhibit, inhibiting and the like in reference to a protein-inhibitor (e.g., BAFF-R antibody provided herein) interaction means negatively affecting (e.g., decreasing) the activity or function of the protein (e.g., decreasing the activity of BAFF-R) relative to the activity or function of the protein in the absence of the inhibitor (e.g., BAFF-R antibody). Inhibition includes reduction of a disease or symptoms of disease (e.g., cancer or an autoimmune disease). Thus, inhibition includes, at least in part, partially or totally blocking stimulation, decreasing, preventing, delaying activation, inactivating, desensitizing, or down-regulating signal transduction or enzymatic activity or the amount of a protein. Similarly an inhibitor is a compound or protein that inhibits BAFF-R activity, e.g., by binding, partially or totally blocking, decreasing, preventing, delaying, inactivating, desensitizing, or down-regulating activity (e.g., BAFF-R signaling activity).

Agents provided herein, e.g., antibodies, are often administered as pharmaceutical compositions comprising an active therapeutic agent and a variety of other pharmaceutically acceptable components. See, *Remington: The Science and Practice of Pharmacy, 22nd Edition*, Loyd V. Allen et al., editors, Pharmaceutical Press (2012). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The compositions can be administered for therapeutic or prophylactic treatments. In therapeutic applications, compositions are administered to a patient suffering from a disease (e.g., cancer) in a therapeutically effective dose. Amounts effective for this use will depend upon the severity of the disease and the general state of the patient's health. Single or multiple administrations of the compositions may be administered depending on the dosage and frequency as required and tolerated by the patient. A patient or subject includes both humans and other animals, particularly mammals. Thus, the methods are applicable to both human therapy and veterinary applications. Optionally, the patient is a mammal, a primate, or human.

Formulations suitable for oral administration can consist of (a) liquid solutions, such as an effective amount of the antibodies provided herein suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation can be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administrations contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

The terms disease or condition refer to a state of being or health status of a patient or subject capable of being treated with a compound, pharmaceutical composition, or method provided herein. Optionally, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term cancer refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term leukemia refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the terms metastasis, and metastatic cancer can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term associated or associated with in the context of a substance or substance activity or function associated with a disease (e.g., cancer (e.g. leukemia, lymphoma, B cell lymphoma, or multiple myeloma)) means that the disease (e.g. cancer, (e.g. leukemia, lymphoma, B cell lymphoma, or multiple myeloma)) is caused by (in whole or in part), or a symptom of the disease is caused by (in whole or in part) the substance or substance activity or function.

As used herein, an autoimmune disease refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjögren's syndrome,vasculitis, glomerulonephritis, auto-immune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma.

As used herein, an inflammatory disease refers to a disease or disorder associated with abnormal or altered inflammation. Inflammation is a biological response initiated by the immune system as part of the healing process in response to a pathogen, damaged cells or tissues or irratants. Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

A humanized antibody is a genetically engineered antibody in which at least one CDR (or functional fragment or variant thereof) from a mouse antibody ("donor antibody," which can also be rat, hamster or other non-human species) are grafted onto a human antibody framework ("acceptor antibody"). Optionally, more than one mouse CDR is grafted (e.g. all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, a humanized antibody may be an antibody having one or more CDRs from a donor antibody and a variable region framework (FR). The FR may form part of a constant region and/or a variable region within a human antibody. In addition, in order to retain high binding affinity, amino acids in the human acceptor sequence may be replaced by the corresponding amino acids from the donor sequence, for example, where (1) the amino acid is in a CDR or (2) the amino acid is in the human framework region (e.g., the amino acid is immediately adjacent to one of the CDRs). See, U.S. Pat. Nos. 5,530,101 and 5,585,089, incorporated herein by reference, which provide detailed instructions for construction of humanized antibodies. Although humanized antibodies often incorporate all six CDRs (e.g., as defined by Kabat, but often also including hypervariable loop H1 as defined by Chothia) from a mouse antibody, they can also be made with fewer mouse CDRs and/or less than the complete mouse CDR sequence (e.g., a functional fragment of a CDR) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Typically a humanized antibody as provided herein may include (i) a light chain variable region comprising at least one CDR (often three CDRs) from a mouse antibody (also referred to herein as a mouse CDR) and a human variable region framework; and (ii) a heavy chain variable region comprising at least one CDR (often three CDRs) from the mouse antibody and a human variable region framework (FR). The light and heavy chain variable region frameworks (FRs) may each be a mature human antibody variable region framework sequence (or fragment thereof), a germline variable region framework sequence (combined with a J region sequence) (or fragment thereof), or a consensus sequence of a human antibody variable region framework sequence (or fragment thereof). Optionally, the humanized antibody includes a light chain variable region as described in (i), a heavy chain variable region as described in (ii) together with a light chain human constant region and a heavy chain human constant region.

A chimeric antibody is an antibody in which the variable region of a mouse (or other rodent) antibody is combined with the constant region of a human antibody; the construction of a chimeric antibody by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

Other approaches to design humanized antibodies may also be used to achieve the same result as the methods in U.S. Pat. Nos. 5,530,101 and 5,585,089. For example, superhumanization as described in Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include reshaping, hyperchimerization and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

The examples below are intended to further illustrate certain aspects of the methods and compositions described herein, and are not intended to limit the scope of the claims.

EXAMPLES

Example 1

Novel BAFF-Receptor Antibody to Natively Folded Recombinant Protein Eliminates Drug Resistant Human B-Cell Malignancies In Vivo Conventional recombinant immunogen proteins produced in bacteria for developing mAbs lack post-translational modifications and are simplistically folded because compared with eukaryotes, prokaryotes lack chaperone proteins and oxidizing environments. As a result, such proteins may differ in conformational structure from the corresponding plasma membrane-anchored native proteins. Furthermore, antibodies may be raised against off-target domains such as transmembrane or intracellular domains of the target protein. As described herein, a strategy of generating mAbs against a natively folded, glycosylated immunogen expressed on eukaryotic cells was applied. Specifically, human BAFF-R as a native protein on mouse fibroblast cells, and used the engineered cell clone as an immunogen in mice. Described herein is the generation of novel mAbs that specifically bound and lysed human malignant B cell lines and primary lymphomas in vitro, and inhibited growth of drug-resistant lymphoma cell lines in xenogenic tumor models in vivo.

Materials and Methods

Animals, cell lines, and primary human tumor samples. BALB/c mice for antibody development and NOD scid gamma (NSG) breeding pairs were purchased from The Jackson Laboratory (Bar Harbor, ME). The NSG breeding colony was maintained by the Animal Resource Center at City of Hope. Mice were housed in a pathogen-free animal facility according to institutional guidelines. All animal studies were approved by the Institutional Animal Care and Use Committee (IACUC: 15020). JeKo-1, SU-DHL-6, Raji, U266 and RL were purchased from ATCC (Manassas, VA). Z-138 line was provided by Dr. Michael Wang (MD Anderson Cancer Center). Ibrutinib-resistant SP49-IR line was developed and provided by Dr. Jianguo Tao (University of South Florida). Ibrutinib-resistant SP49 cell lines (SP49-IR) were established by treating cells with escalating doses of ibrutinib. IC50 was 5 nM for parental SP49 compared to >100 nM for SP49-IR. At 100 nM ibrutinib ~5% of SP49 cells were viable compared with >90% of SP49-IR cells. Human NK-92 176V cells were obtained from Conkwest Inc. (San Diego, CA). For human blood and tumor samples, non-cultured, primary human lymphomas were obtained as cryopreserved, viable single cell suspensions in 10% DMSO from the Lymphoma Satellite Tissue Bank at MD Anderson Cancer Center under an Institutional Review Board approved protocol (IRB: 2005-0656). Primary patient samples included leukapheresis or blood from patients with mantle cell lymphoma (MCL) or chronic lymphocytic leukemia (CLL), and excised lymph nodes from patients with diffuse large B-cell lymphoma (DLBCL) or follicular lymphoma (FL). Tumor cells in each sample ranged from 80% to 98% for leukapheresis or blood, and from 50% to 60% for lymph node biopsies. Peripheral blood mononuclear cells (PBMC) was provided by the Michael Amini Transfusion Medicine Center at City of Hope (IRB: 15283).

Generation of human-BAFF-R expressing mouse fibroblast cells. Human BAFF-R (hBAFF-R) cDNA was from human B cells and cloned in-frame with GFP gene on pEGFP-N1 vector (Takara/Clotech, Mountain View, CA). hBAFF-R cDNA sequence was confirmed against the NCBI gene sequence database (Gene ID: 115650). The cDNA encoding hBAFF-R-GFP fusion was subsequently cloned into a lentivirus gene delivery system (pLenti6/V5-DEST Gateway Vector kit, Life Technologies, Grand Island, NY) to produce hBAFF-R-GFP fusion proteins when transduced into mouse fibroblast (L) cells. Single cell clones were established from sorted GFP-positive L cells, and (h) BAFF-R-GFP-expressing L cell clone D2C was used in further studies.

Antibody-producing hybridomas. Two 6-week-old BALB/c mice were immunized with D2C cells by five subcutaneously injections at the foot pad once every three days. Blood samples were obtained from both mice to measure serum antibodies against D2C by ELISA. Splenic tissue was harvested on day 20. Harvested splenocytes were fused with Sp2/0 myeloma to establish hybridomas and ELISA screened for antibodies using D2C or parental L cell-coated plates. Immunization and hybridoma procedures were conducted at the Antibody Core Facility at MD Anderson Cancer Center.

Chimeric antibody production. cDNA from selected hybridomas encoding the variable regions of antibody light and heavy chains were engineered onto expression vectors containing respective human IgG1 constant regions. Vectors were co-transfected into the FreeStyle 293 Expression System (Life Technologies, Carlsbad, CA) according to manufacturer's directions. Antibodies in culture supernatant were purified by HiTrap Protein A affinity chromatography columns (GE Healthcare, Marlborough, MA) according to the manufacturer's directions.

Cytotoxicity assays. Target cells (L cells, human tumor lines, primary patient samples) were labeled with chromium-51 (51Cr, Perkin Elmer, Waltham, MA) for a 51Cr release assay. Briefly, antibodies and effectors (NK cells or complement serum standard [Sigma Aldrich, St. Louis, MO]), were added to labeled target cells and incubated up to 18 hours. NK cells were enriched from PBMC (NK cell enrichment kit, Stemcell Technologies, Vancouver, Canada). 51Cr released into supernatant was detected with a Wizard Automatic Gamma Counter (Perkin Elmer).

Generation of JeKo-1-CD20-KO. FACS-sorted, stable JeKo-1-CD20-KO were generated using CD20-CRISPR/Cas9 and HDR Plasmid Systems (Santa Cruz Biotechnology, Santa Cruz, CA) according to manufacturer's directions. CD20 knock-out was verified by flow cytometry and Western blots.

In vivo studies. For tumor models, stable, luciferase-expressing tumors lines were established for bioluminescent imaging in mouse models. Briefly, a luciferase gene was introduced into tumor lines by a lentivirus gene delivery system (pLenti7.3/V5-DEST Gateway Vector Kit, Life Technologies, Carlsbad, CA). The minimum lethal dose per mouse was determined for each tumor cell line by dose titration. Tumor cells were injected intravenously (IV) and mice were monitored by in vivo bioluminescence imaging for minimum tumor dose to ensure engraftment. Minimum lethal tumor doses were: $1 \times 10^6$ JeKo-1, $5 \times 10^5$ RS4; 11, $5 \times 10^5$ JeKo-1-CD20-KO, or $2.5 \times 10^4$ Z-138 cells.

Bioluminescent Imaging: Mice were anesthetized with isoflurane and administered 150 mg/kg D-luciferin (Life Technologies, Carlsbad, CA) via intraperitoneal (IP) injection 10 minutes prior to imaging. Imaging was performed on an AmiX imaging system (Spectral Instruments Imaging, Tucson, AZ).

Antibody Studies: Mice (n=5 per group) were IV tumor challenged three days prior to four treatments once every five days. Treatments were 300 ρL IV injection: 200 μg treatment antibody, $10 \times 10^6$ effector human NK-92-176V cells, and $5 \times 10^4$ IU IL-2 (Prometheus Laboratories, San Diego, CA). Control groups received the same volume injections with a control antibody or without the antibody and/or NK cells. Bioluminescent imaging was performed weekly up to 80 days. Survival was tracked up to 100 days post tumor challenge.

Results

Figure 1A:
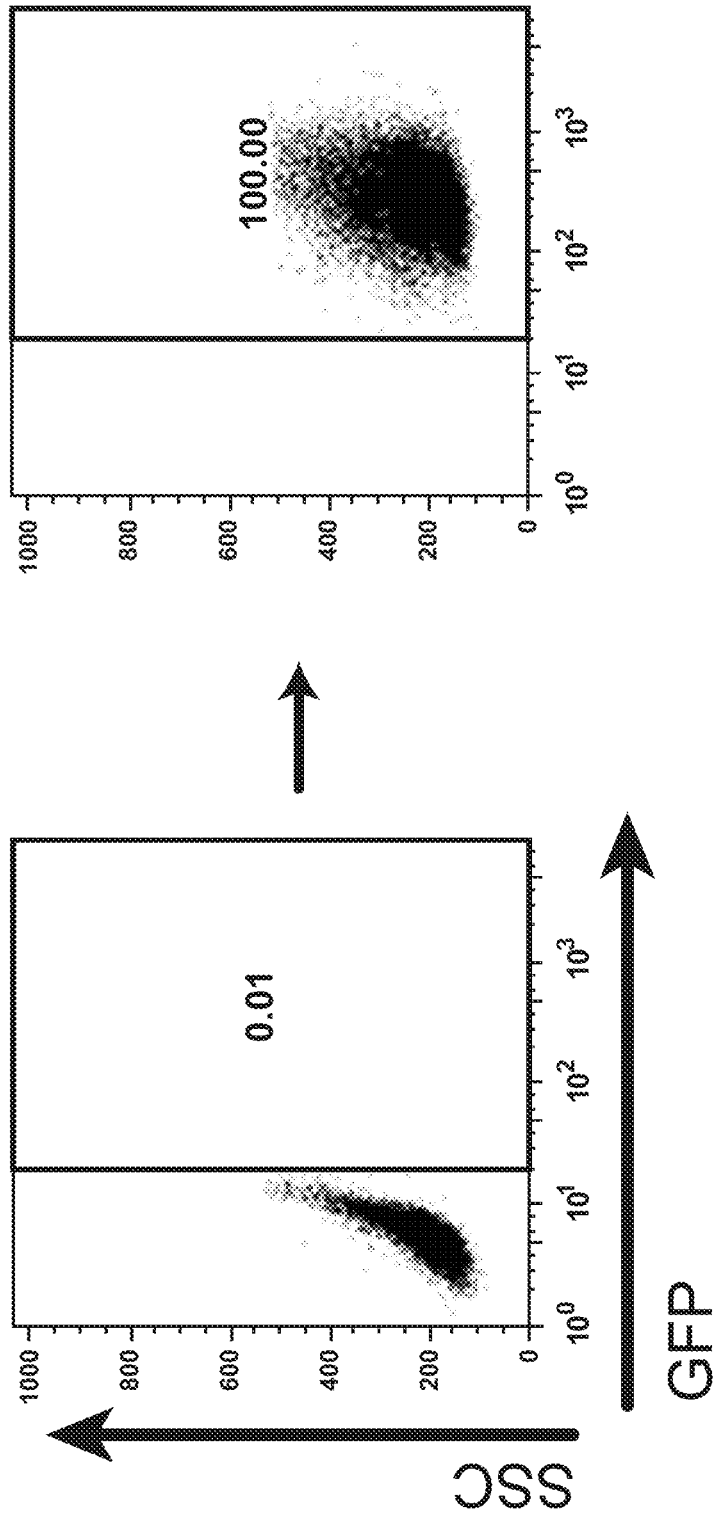
FIGS. 1A, 1B, 1C, 1D and 1E are FACS images showing generation and specificity of novel monoclonal antibodies against human BAFF-R.
Figure 7A:
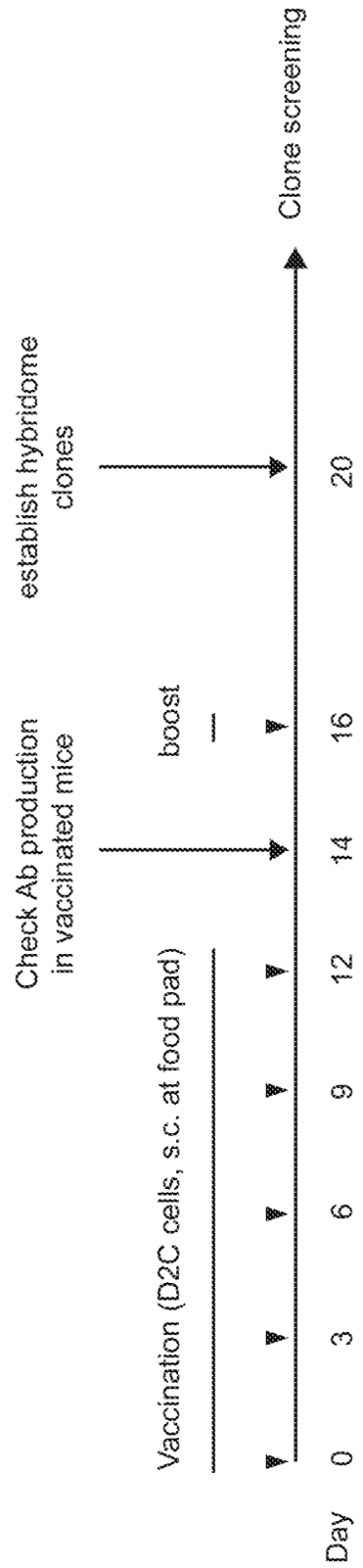

Generation of monoclonal antibodies against human BAFF-R. In order to generate a therapeutic antibody to a biologically relevant epitope of BAFF-R, a eukaryotic cell-surface expression system was used in which endogenous cell-surface proteins are presented in their native conformation with appropriate post-translational modifications. A mouse fibroblast (L) cell clone was engineered expressing cell-surface GFP-tagged, human BAFF-R. BAFF-R-expressing L cell clones were generated and characterized for GFP expression (FIG. 1A). Clone D2C was expanded and successfully used to immunize BALB/c mice according to Methods and immunization schedule in FIG. 7A.

Figure 8:
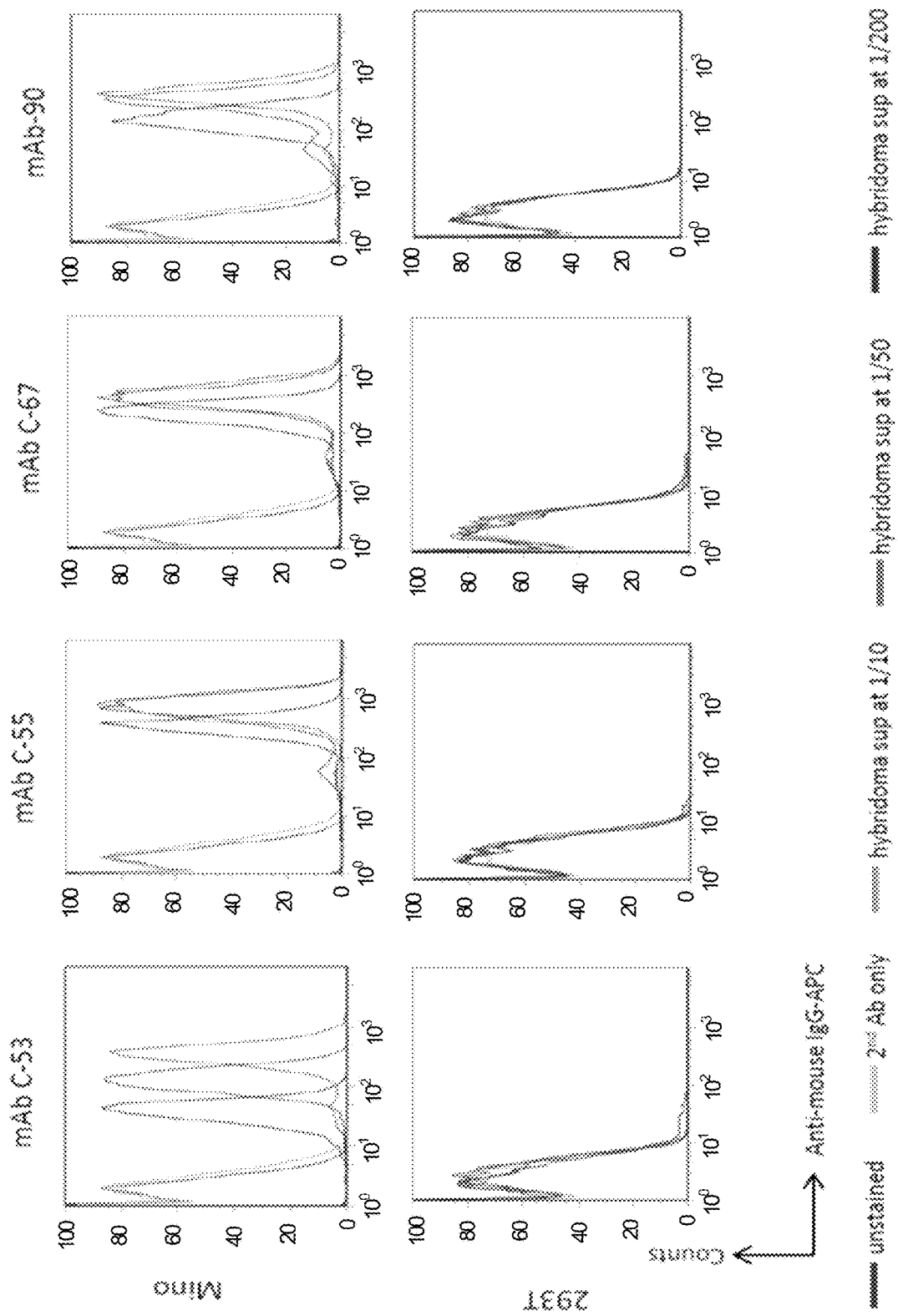
FIG. 8 are flow cytometry results showing verification that selected hybridoma clones bind MCL cells. Binding of hybridoma Clone 53, 55, 67, and 90 supernatants (1/10, 1/50, and 1/200 dilutions) to Mino (mantle cell lymphoma) and 293T (negative control) cell lines assessed by flow cytometry performed with anti-mouse IgG-APC.

After generating and screening hybridoma clones, four clones (53, 55, 67, and 90) were identified as producing antibodies that specifically bound BAFF-R-expressing, but not parental, L cells (FIG. 7B). Supernatants of all four clones contained antibodies that bound BAFF-R-expressing Mino cell line (MCL) in a dose-dependent manner. No antibody binding was detected in BAFF-R-negative control cell line, 293T (FIG. 8).

Figure 1B:
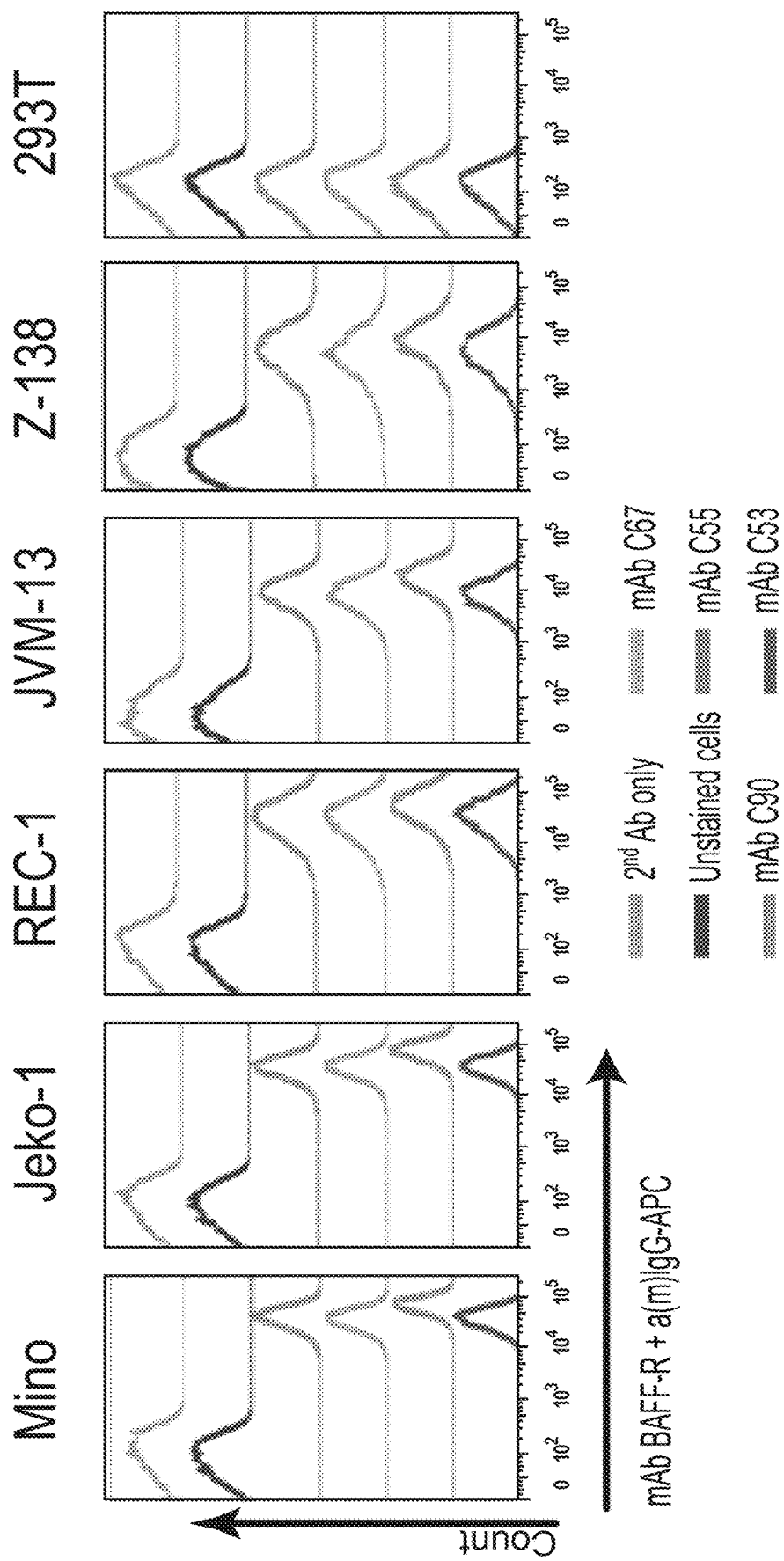
Figure 9:
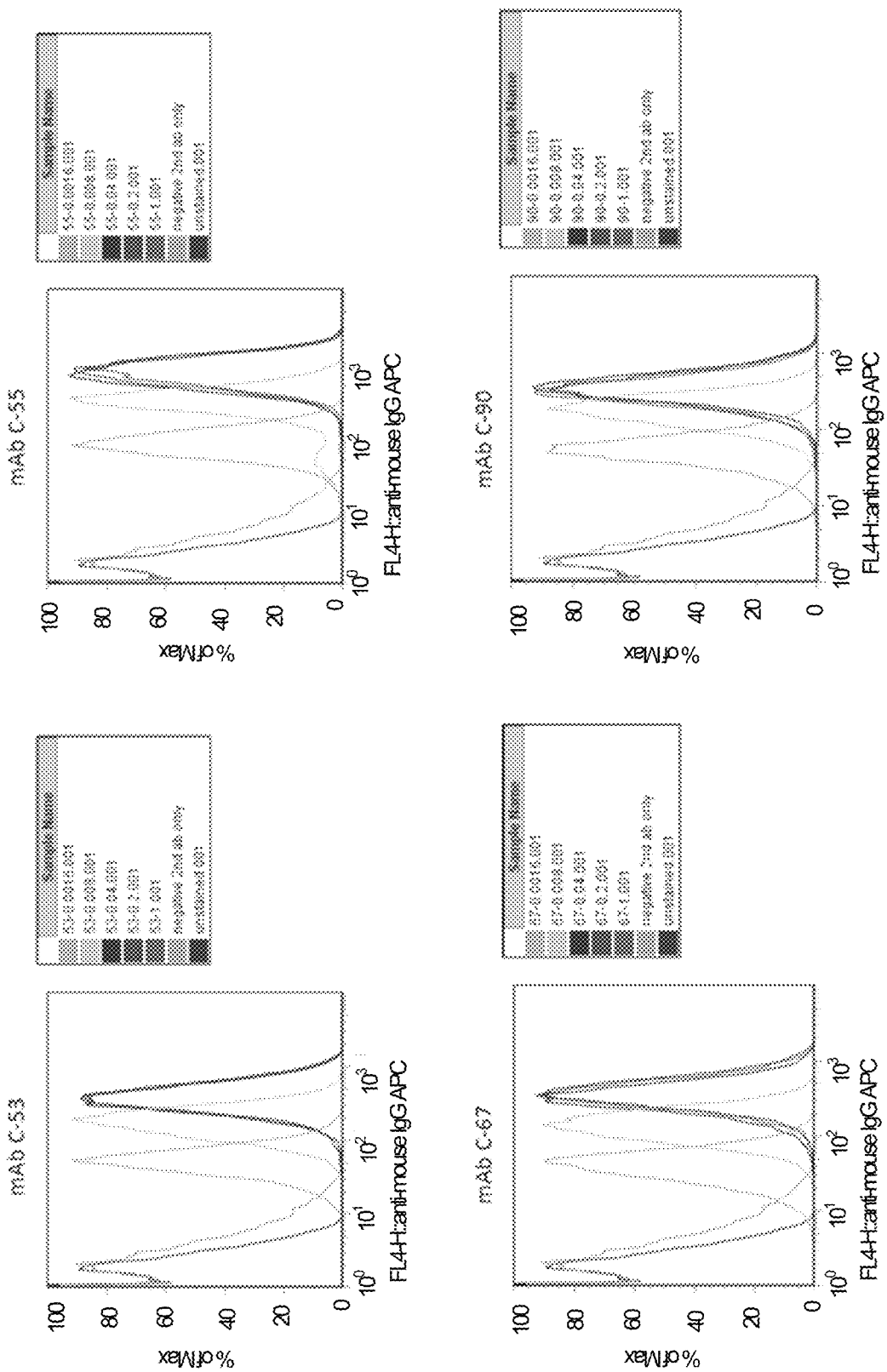
FIG. 9 are graphs showing dose-dependent binding of purified mAbs to human BAFF-R. Mouse mAb from hybridoma Clones 53, 55, 67, 90 were purified by protein A affinity chromatography. Binding of serially diluted (1 µg/10$^6$ cells-1.6 ng/10$^6$ cells) purified mouse mAb to Mino cells was assessed by flow cytometry with anti-mouse IgG-APC secondary antibody.

Antibodies from the four hybridoma supernatants were purified by protein A affinity chromatography. Purified antibodies bound Mino cells in a dose-dependent manner (FIG. 9), as well as other human MCL lines, including JeKo-1, REC-1, and ibrutinib-resistant JVM-13 and Z-138 (FIG. 1B).

Figure 10:
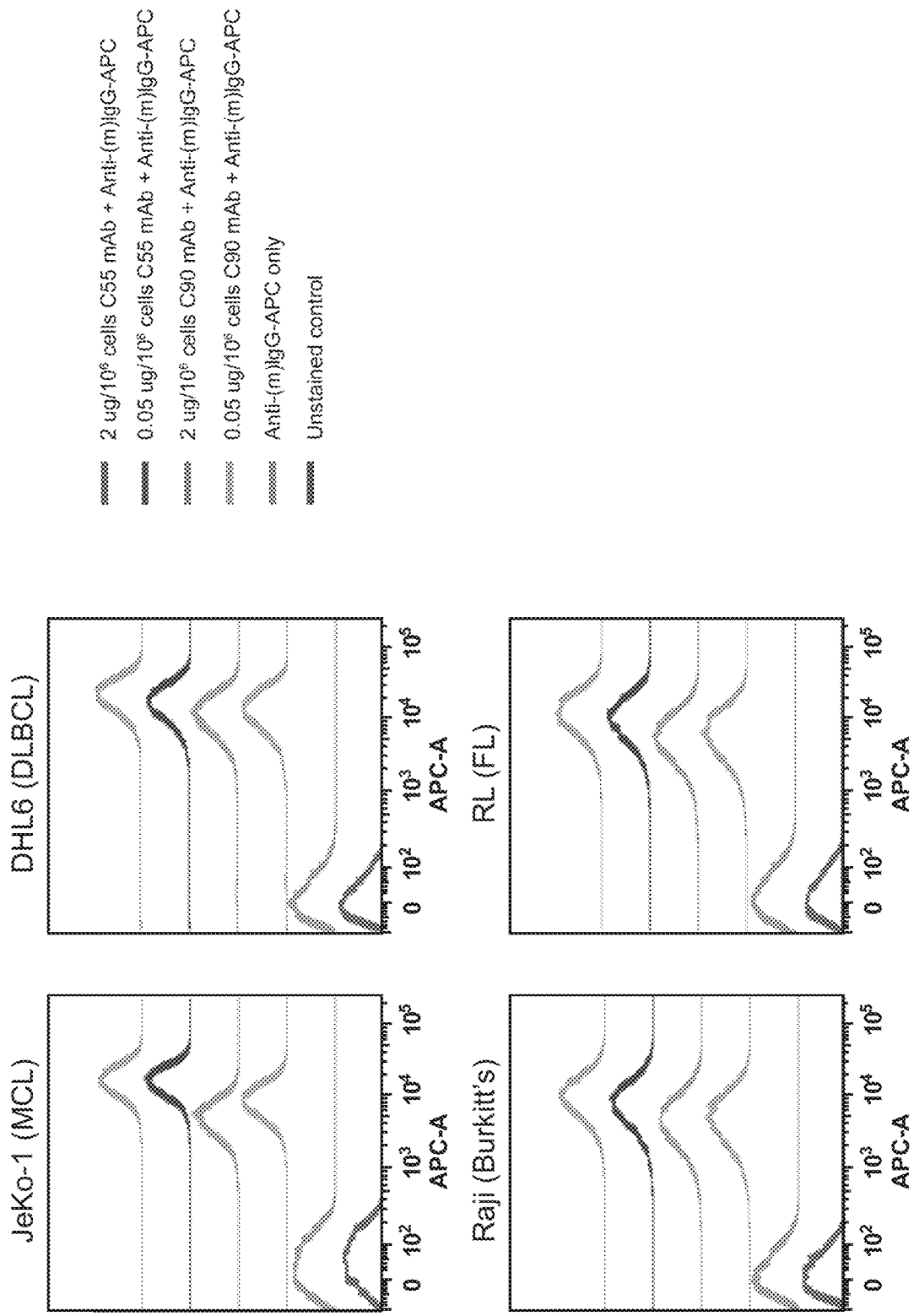
FIG. 10 are results of FACS analyses showing hBAFF-R mAbs recognized non-Hodgkin lymphoma cell lines in vitro. Mouse mAb Clones 55 and 90 bound additional cell lines at high (2 µg mAb/10$^6$ cells) and low (0.05 µg mAb/10$^6$ cells) doses: JeKo-1 (mantle cell lymphoma), SU-DHL-6 (diffuse large B cell lymphoma), Raji (Burkitt lymphoma) and RL (follicular lymphoma). Flow cytometry analysis was performed with anti-mouse IgG-APC. The traces from top to bottom as shown in the figures correlate with the variables (e.g., antibody type or cell type) used from top to bottom shown next to the figures.

An analysis of the complementarity determining regions (CDRs) on the four antibodies revealed that clones 53, 55, and 67 had nearly identical sequences, whereas clone 90 was unique. Therefore, clones 55 and 90 were selected for further investigation. Both clones 55 and 90 effectively bound JeKo-1 (MCL), SU-DHL-6 (DLBCL), Raji (Burkitt lymphoma), and RL (FL) at both high (2 μg/$10^6$ cells) and low (0.05 μg/$10^6$ cells) concentrations (FIG. 10).

Figure 1C:
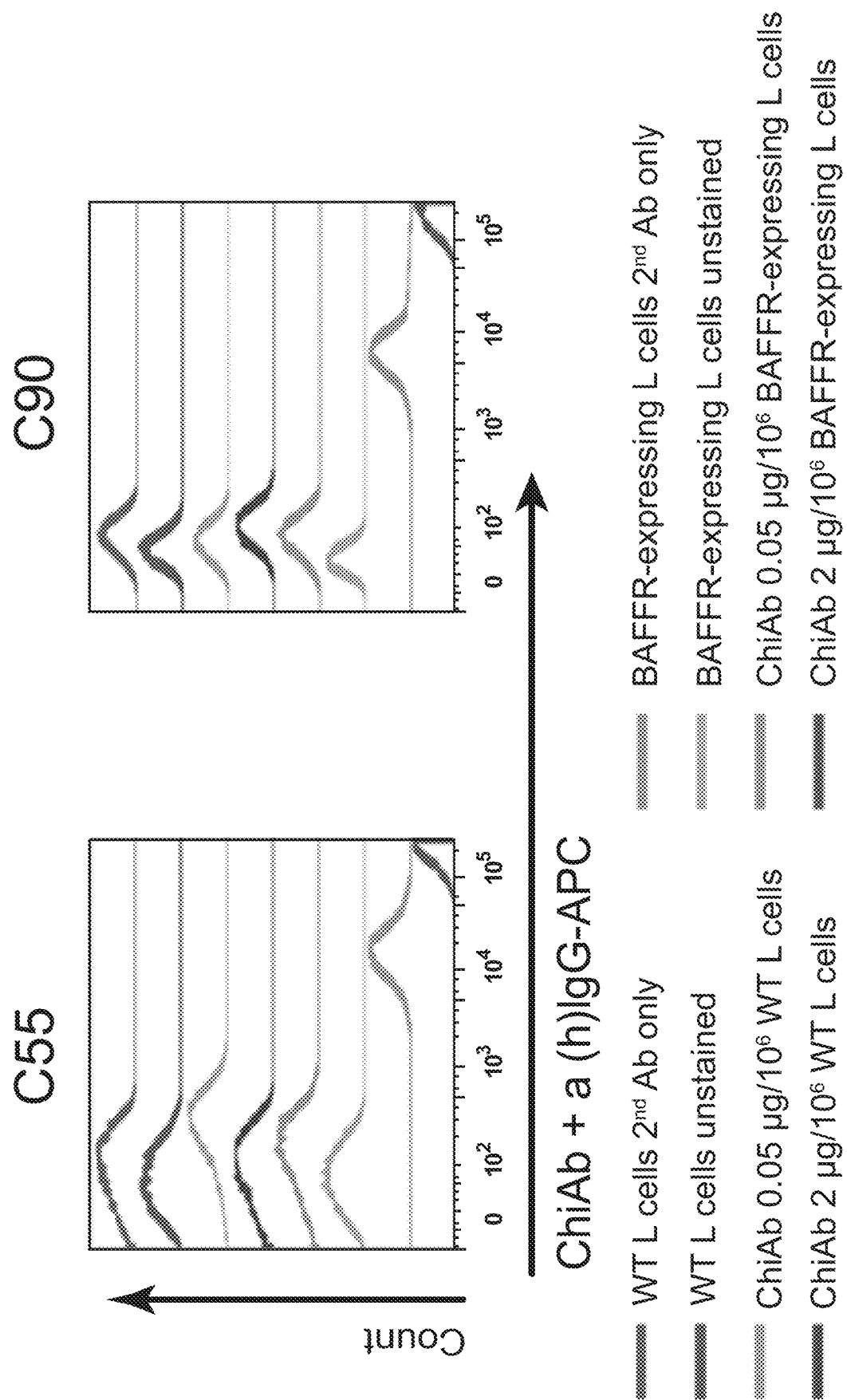
Figure 1D:
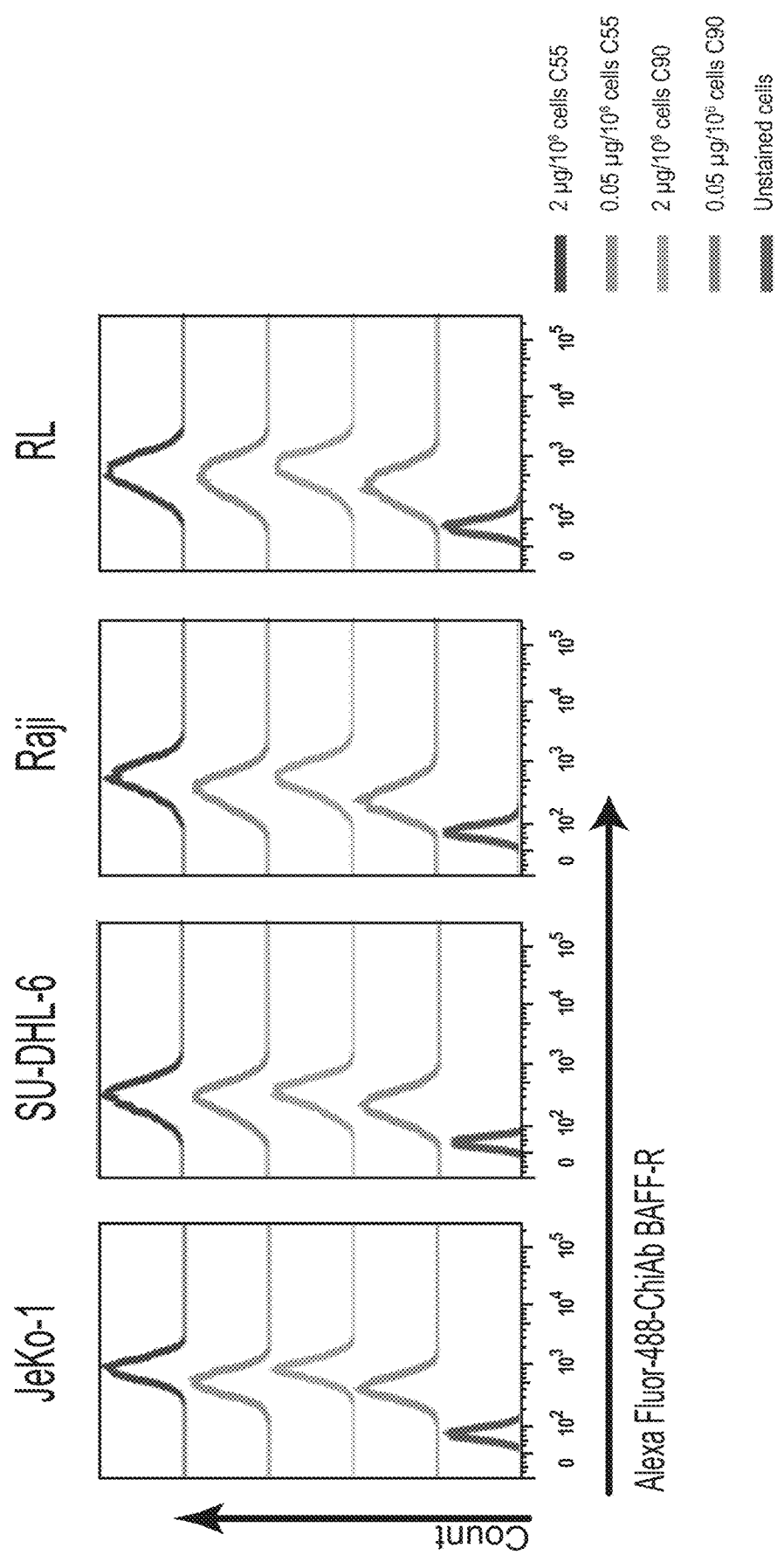
Figure 1E:
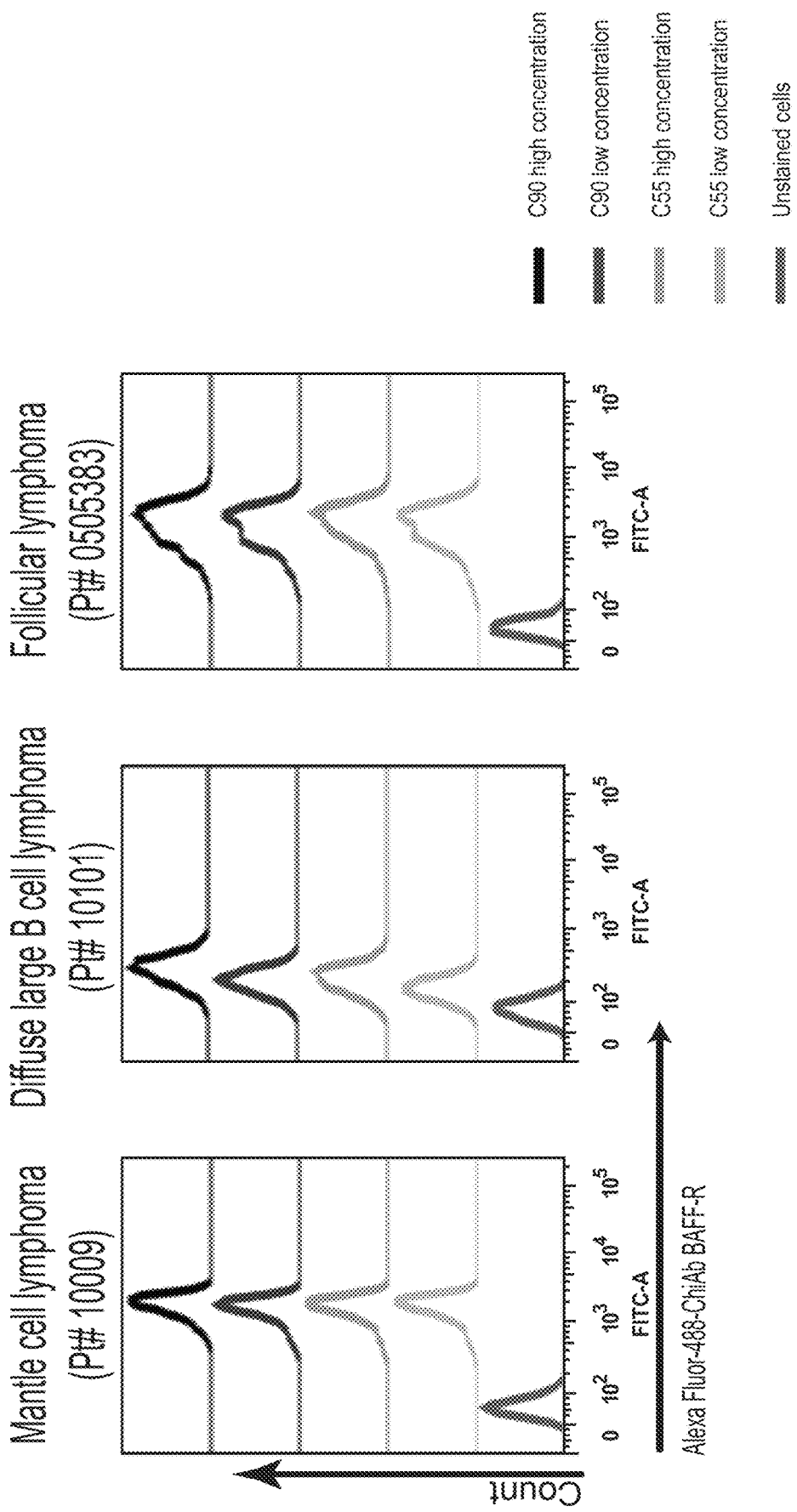
Figure 11:
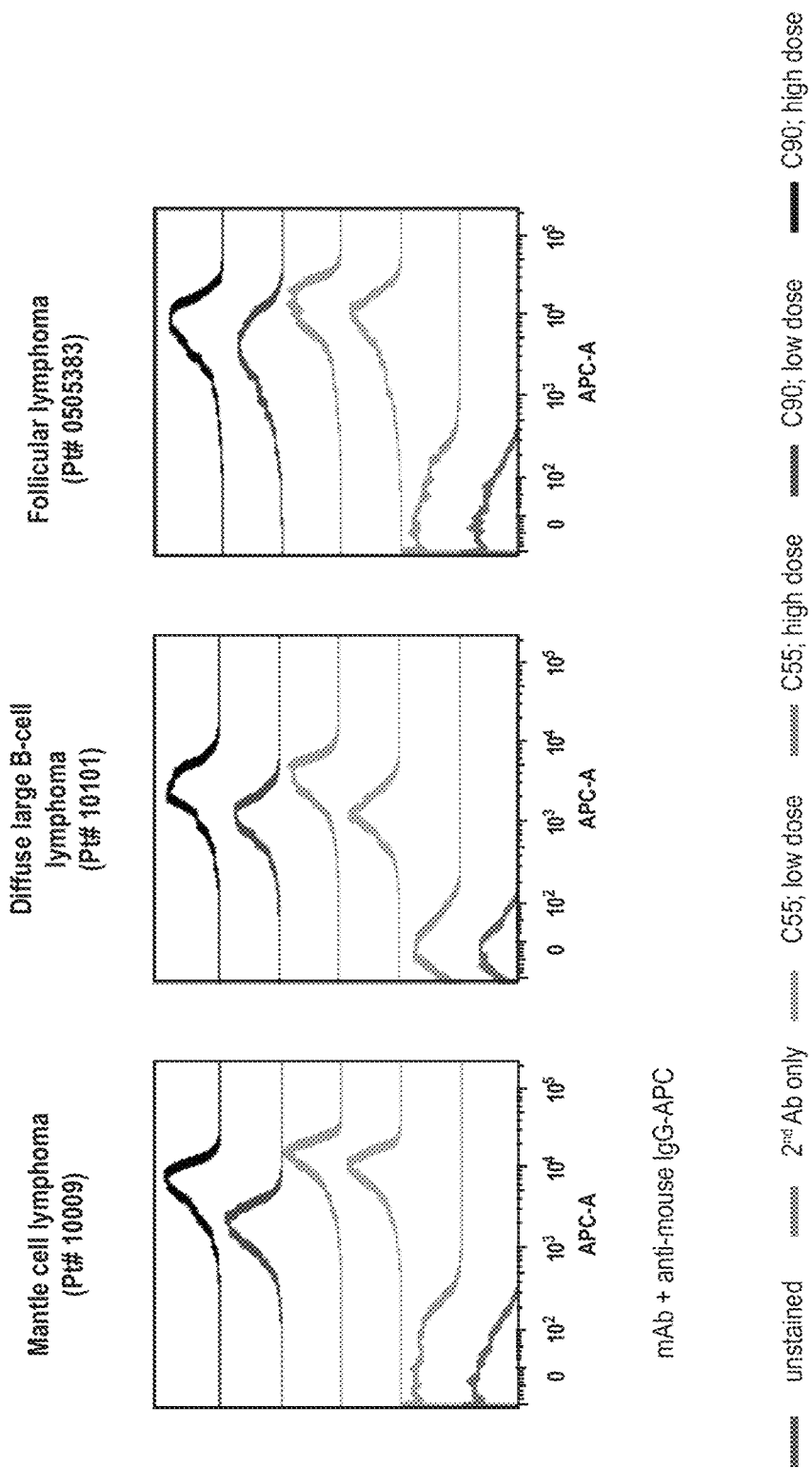
FIG. 11 are graphs showing hBAFF-R mAbs recognized lymphoma patient samples. Mantle cell lymphoma, diffuse large B cell lymphoma, and follicular lymphoma patient samples were stained with mouse mAbs C55 and C90 at high (2 µg/10$^6$ cells) and low (0.05 µg/10$^6$ cells) doses. Flow cytometry analysis was performed with anti-mouse IgG-APC. The traces from top to bottom as shown in the figures correlate with the variables (e.g., antibody type or cell type) used from left to right shown below the figures.

Chimeric mAb against human BAFF-R induced antitumor effects both in vitro and in vivo. Clones 55 and 90 were further developed into their respective chimeric mAbs containing human IgG1 constant regions (termed C55 and C90). The chimeric antibodies retained specific dose-dependent binding to BAFF-R-expressing L cells (FIG. 1C). C55 and C90 were conjugated to Alexa Fluor 488 and exhibited direct binding to non-Hodgkin lymphoma (NHL) lines JeKo-1, SU-DHL-6, Raji, and RL (FIG. 1D). Importantly, chimeric mAbs readily bound MCL, DLBCL, and FL patient primary tumor samples (FIG. 1E and FIG. 11).

Figure 2A:
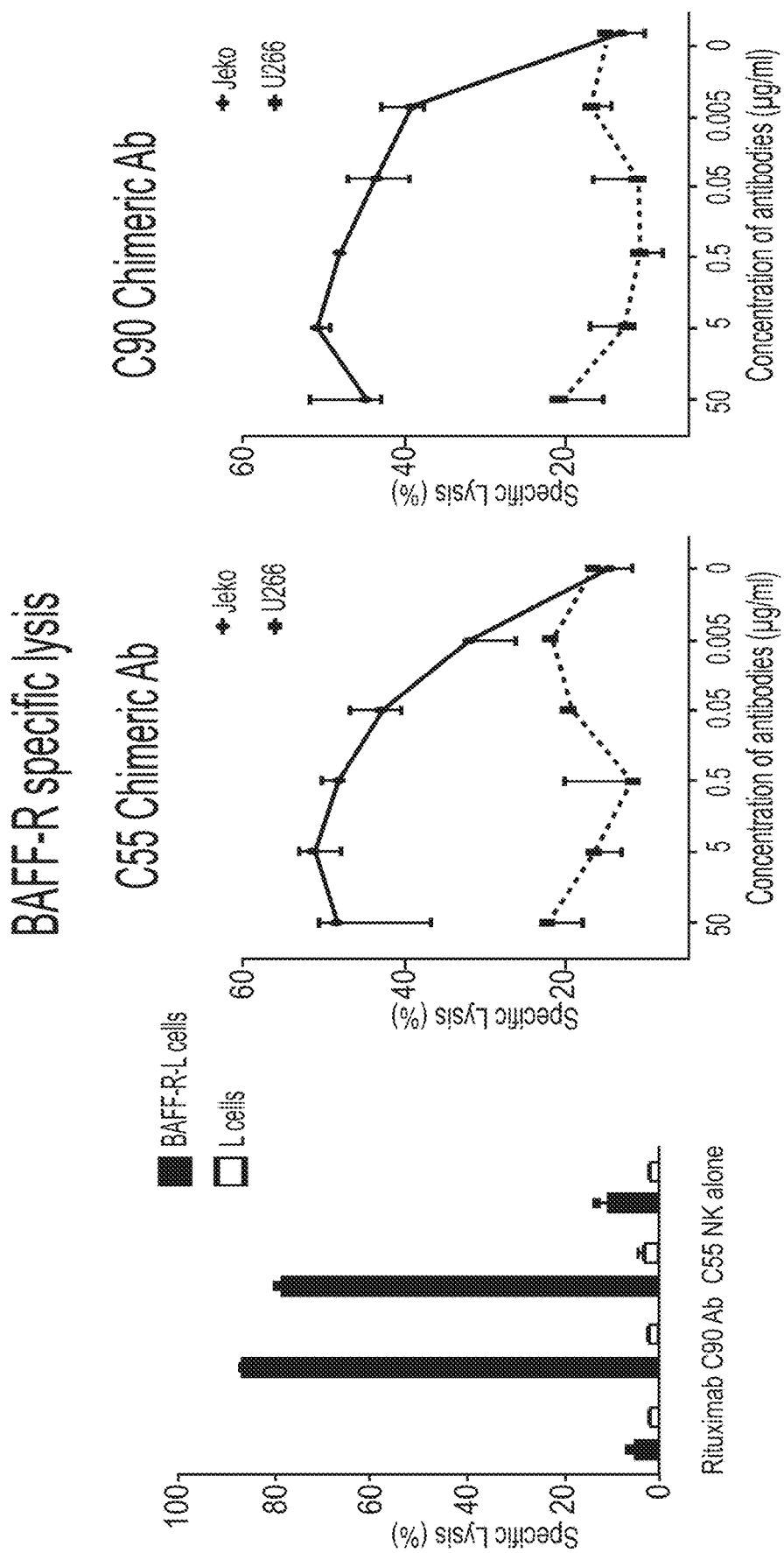
FIGS. 2A, 2B and 2C are graphs showing BAFF-R monoclonal antibodies exhibited specific in vitro cytotoxicity against B-cell tumor lines. Antibody-induced cytotoxicities measured by chromium-51 release after incubation with C55, C90, or rituximab and effectors (NK cells or complement containing serum). NK effector cell to target ratio (E:T) of 20:1. Percentage of cell specific lysis of target cells: the first panel shows BAFF-R-expressing L cell or control parental L cells; the second and third panels show BAFF-R positive JeKo-1 MCL or BAFF-R negative U266 multiple myeloma cells with varying antibody concentrations shown as dose response curves.
Figure 2B:
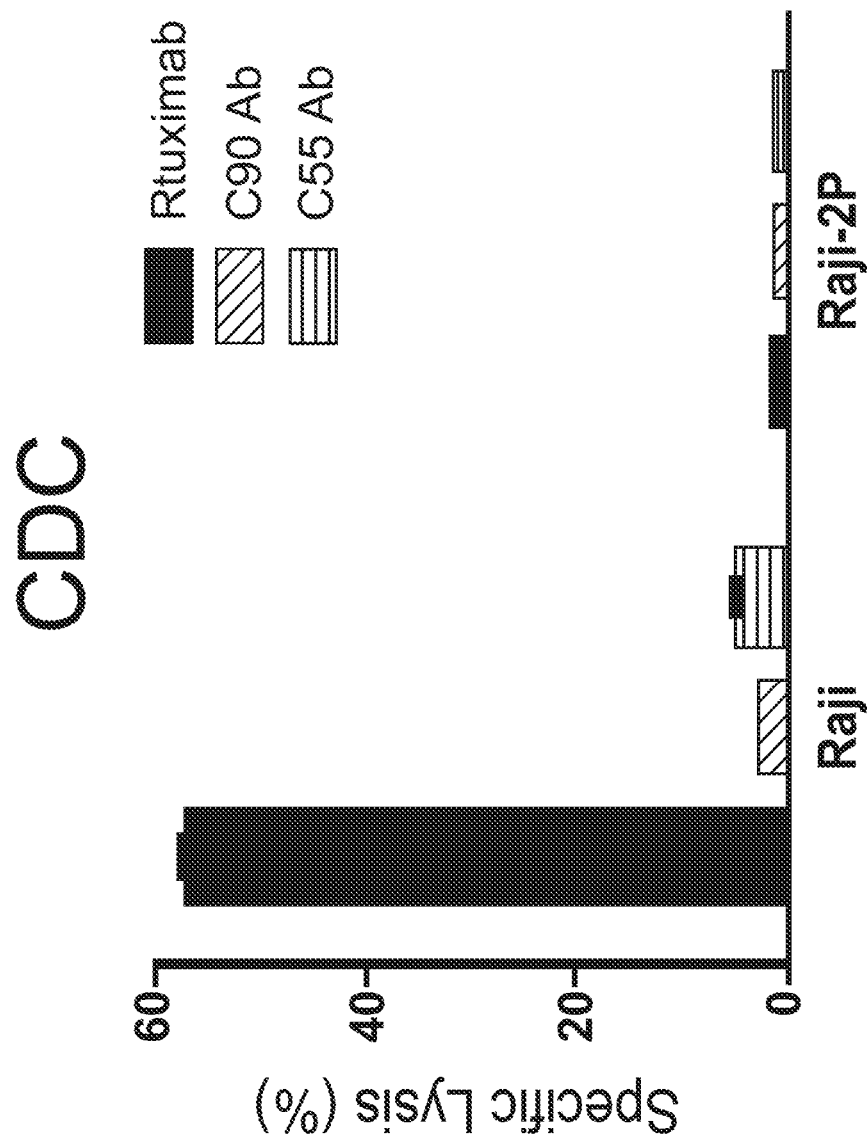
Figure 2C:
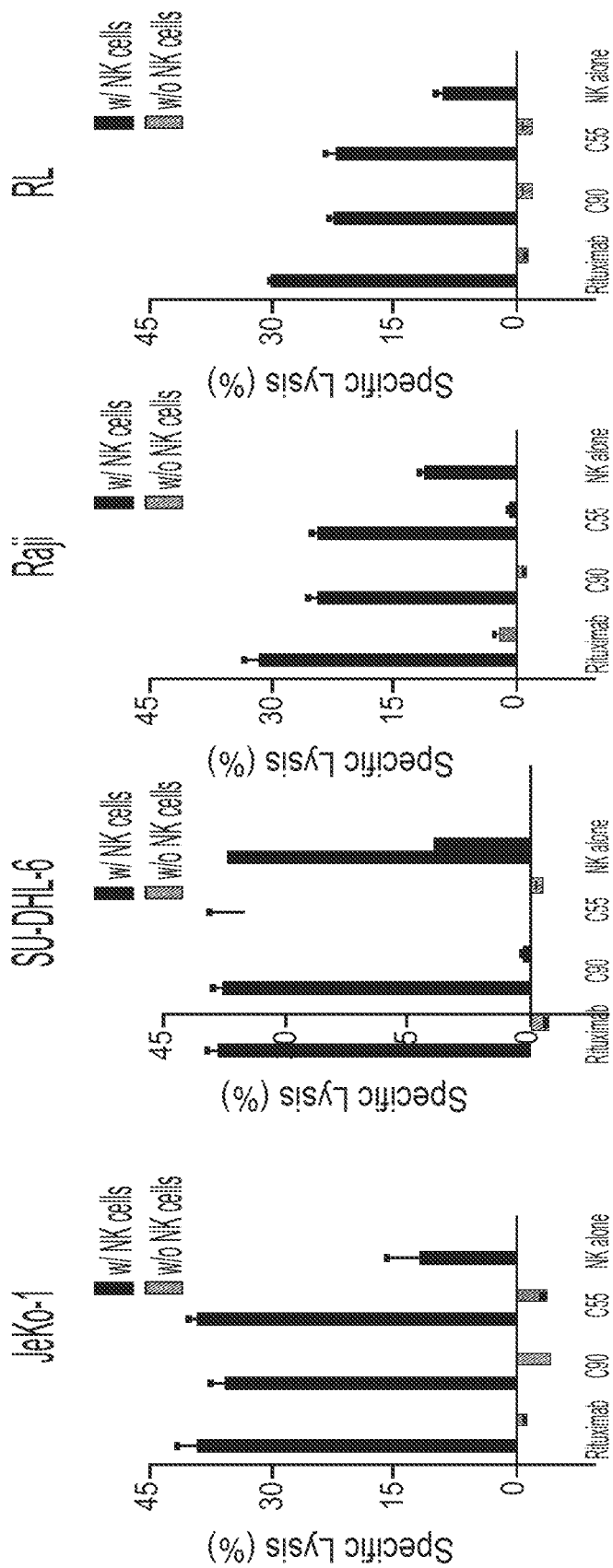
Figure 3A:
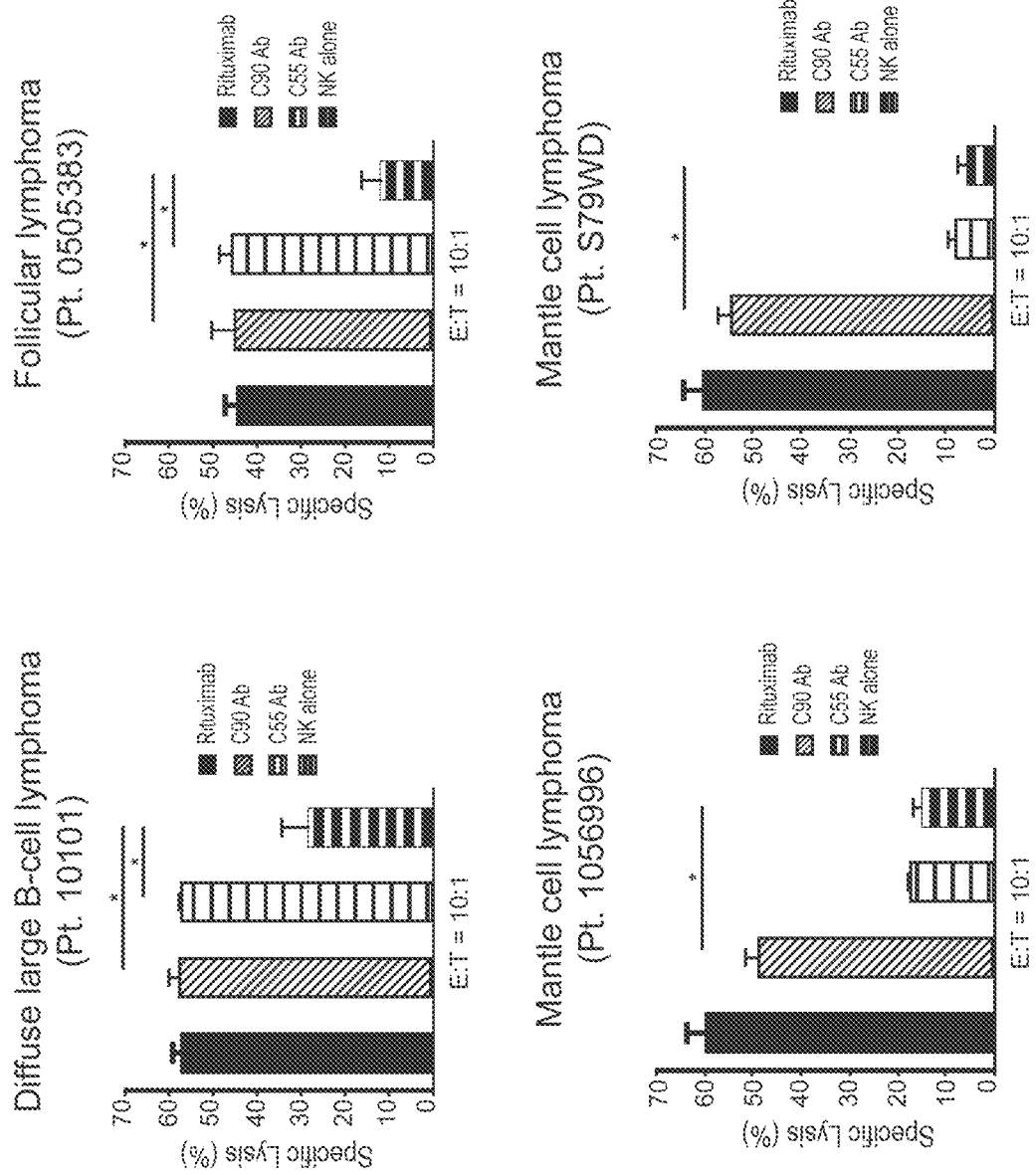
FIGS. 3A and 3B are graphs showing BAFF-R monoclonal antibodies induce in vitro Antibody Dependent Cell-Mediated Cytotoxicity (ADCC) against primary B-cell tumors. Antibody-dependent cell-mediated cytotoxicity (ADCC) effects were measured by chromium-51 release after incubation with C55, C90, or rituximab and effectors (NK cells). Percentage of cell specific lysis of target cells.
Figure 12:
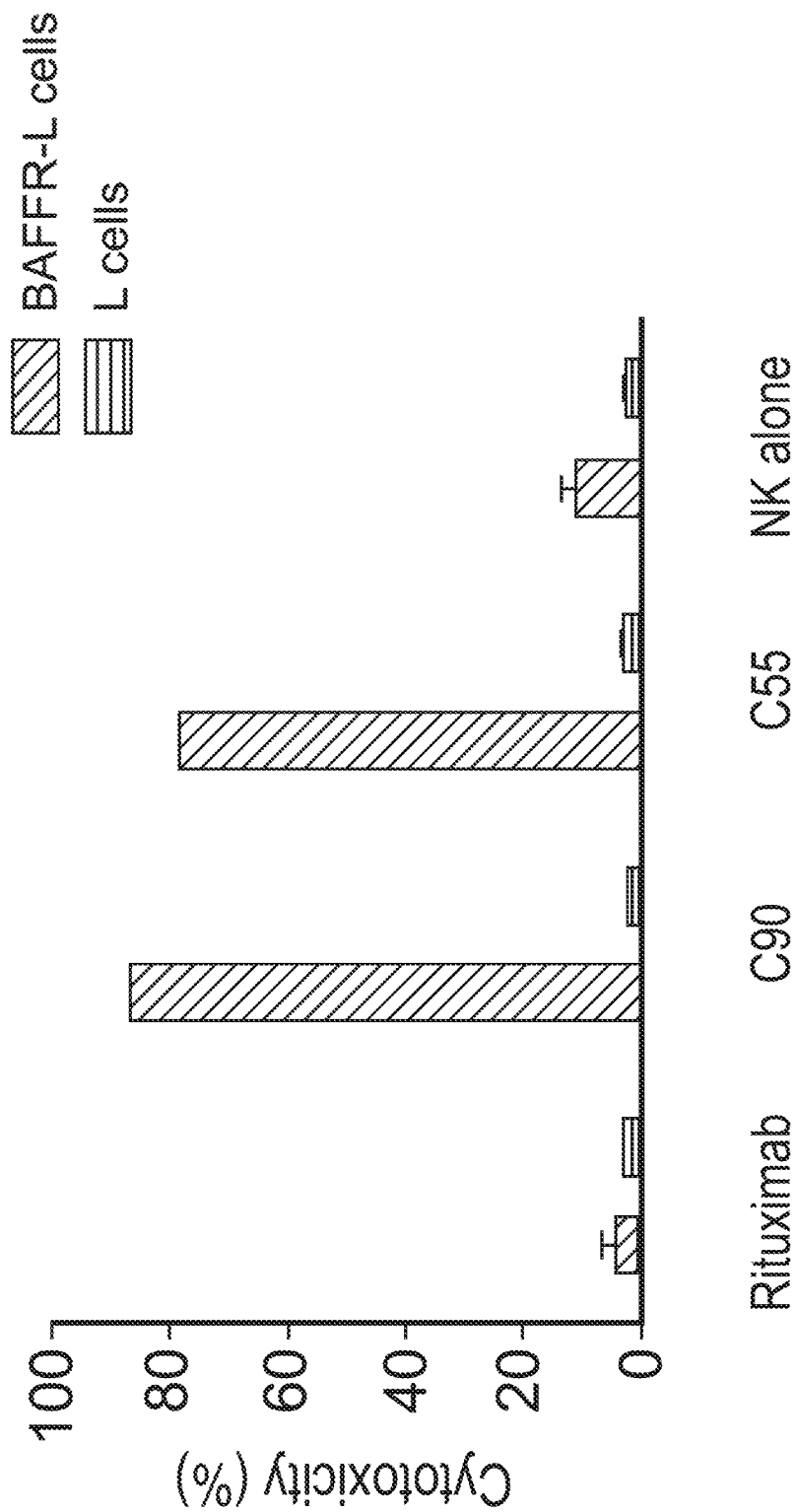
FIG. 12 is a graph showing chimeric antibodies induced ADCC against BAFF-R expressing L cells. BAFF-R-expressing D2C L cells (targets) were labeled with chromium-51 followed by incubation overnight with chimeric mAb+ NK cells (effector to target ratio, 20:1). Culture supernatant was analyzed for released chromium.
Figure 13:
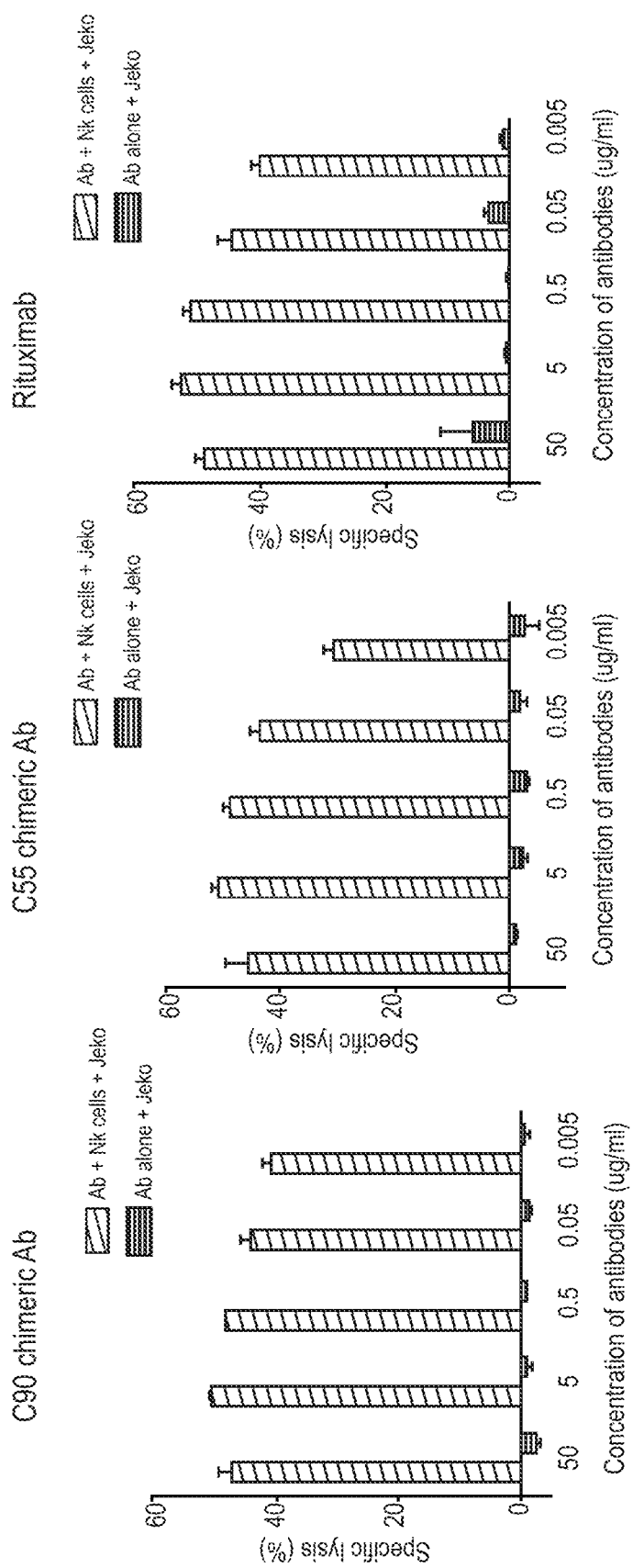
FIG. 13 are graphs showing chimeric antibodies required NK cells for cytotoxicity against tumor cells. JeKo-1 cells (target) were labeled with chromium-51. Cells were incubated with chimeric mAb (C55, C90, or rituximab) and with or without NK cells (effector) at effector to target ratio of 20:1. Chimeric antibodies were added at concentrations from 50 to 0.005 µg/mL. Culture supernatant was analyzed for released chromium.

C55 and C90 elicited antibody-dependent cell-mediated cytotoxicity (ADCC) specifically against BAFF-R-expressing L cells and JeKo-1, but not BAFF-R negative L cells nor the BAFF-R negative human multiple myeloma line, U266 (FIG. 2A, FIG. 12). In contrast, antibodies did not elicit in vitro complement dependent cytotoxicity (CDC, FIG. 2B). Cytotoxicity required the addition of NK cells, as shown for SU-DHL-6, Raji, and RL lymphoma cell lines (FIG. 2C and FIG. 13), suggesting ADCC as a principal mechanism of antibody-mediated cytotoxicity. Importantly, chimeric antibodies elicited ADCC against primary patient tumor samples (FIG. 3A).

Figure 14:
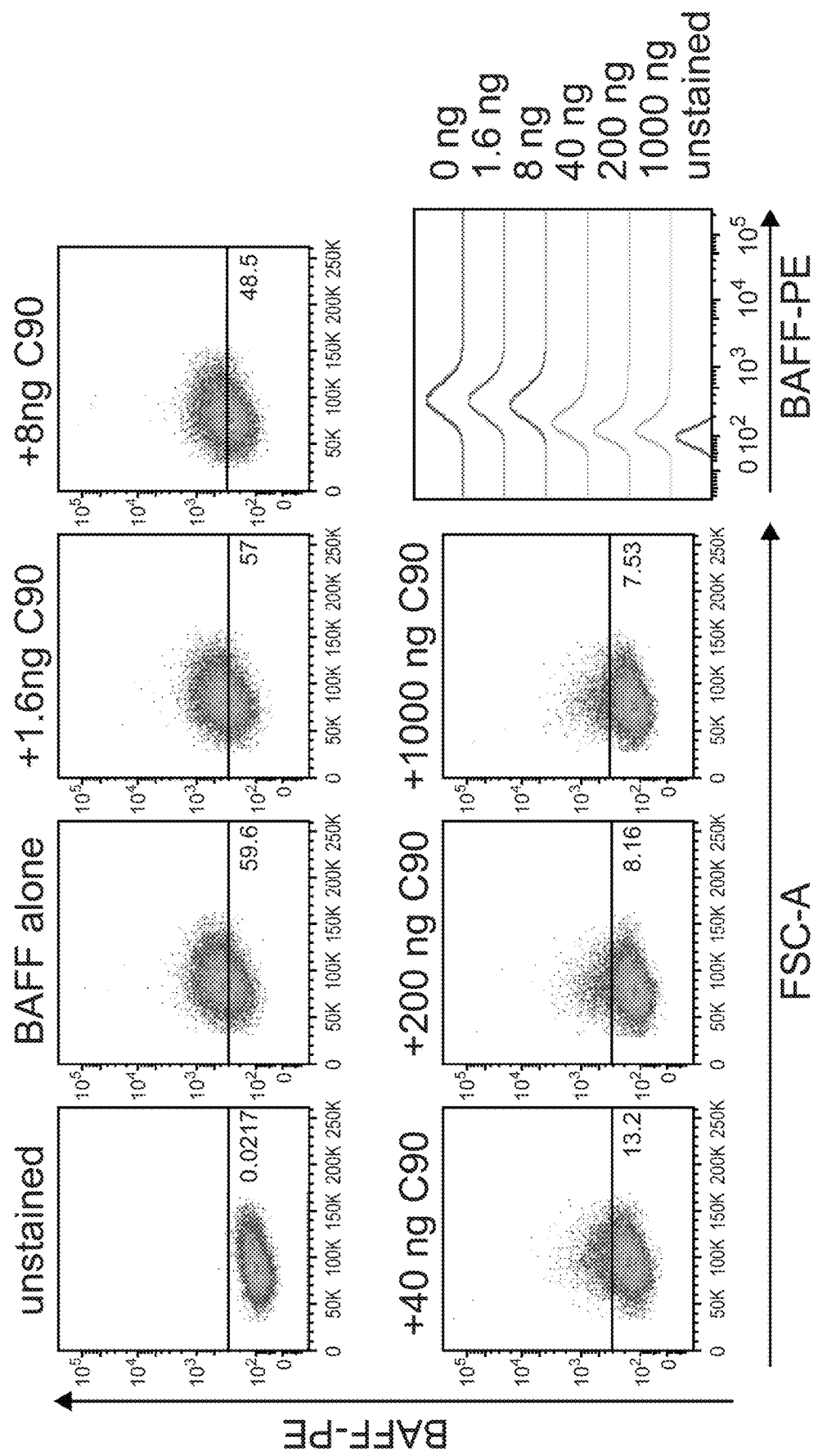
FIG. 14 are FACS results showing hBAFF-R mAb blocked BAFF/BAFF-R interaction. BAFF-R-expressing D2C L cell clones were incubated with C90 at 4° C. for 45 min (0-1000 ng/10$^6$ cells) followed by incubation with recombinant BAFF ligand (0.5 µg/10$^6$ cells) at 4° C. for 90 min. Flow cytometry was performed and gated for anti-BAFF-PE. The signal plot shows BAFF/BAFF-R binding signal in the presence of each mAb concentration. Concentrations shown in the signal plot are shown at the top of each of the FACS results.
Figure 15:
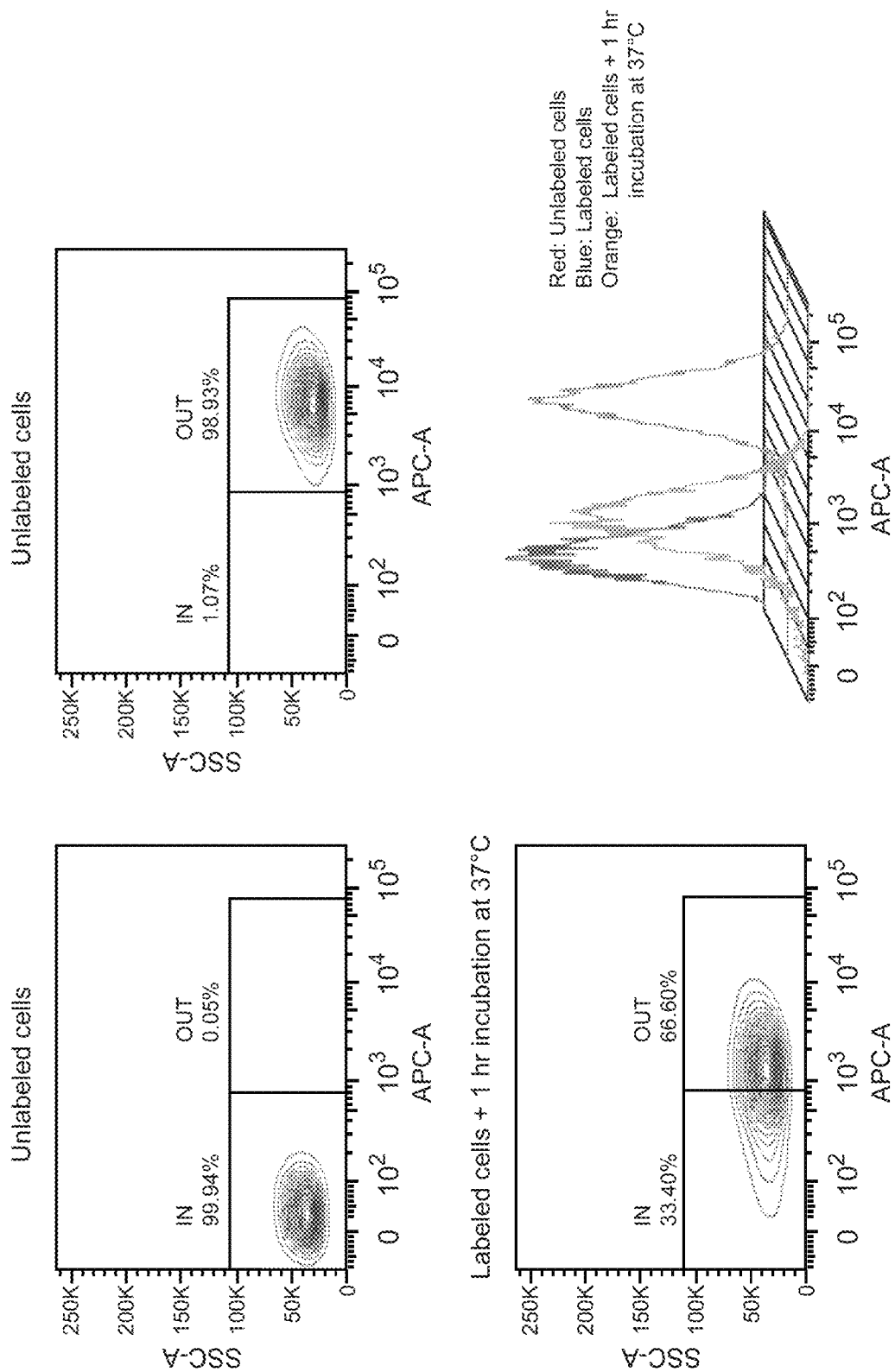
FIG. 15 are FACS results showing limited internalization was observed with BAFF-R mAbs. Mino cells were incubated with mAb C90 (0.05 µg/10$^6$ cells) at 4° C. for 20 minutes followed by incubation at 37° C. for 1 hour. Flow cytometry analysis was performed with anti-mouse IgG-APC. Cells were gated for surface localized antibodies (OUT) and loss of cell surface staining (IN).

The antibodies inhibited BAFF/BAFF-R binding in a dose-dependent manner (FIG. 14), suggesting potential disruption of BAFF/BAFF-R survival signaling in tumor cells. Furthermore, C55 and C90 exhibited limited internalization upon binding BAFF-R (FIG. 15).

In vivo, NSG mice were challenged with luciferase knock-in JeKo-1 MCL cell line followed by antibody treatments. Treatment followed the schedule in FIG. 4A. Mice receiving either C55 or C90 demonstrated significant retardation of tumor growth, compared with PBS or NK cells alone control groups (FIG. 4B). Similarly, C55 and C90 also markedly retarded tumor growth in RS4; 11 (acute lymphoblastic leukemia, ALL) challenged NSG mice, compared with no inhibition by rituximab or controls (FIG. 4C).

Figure 3B:
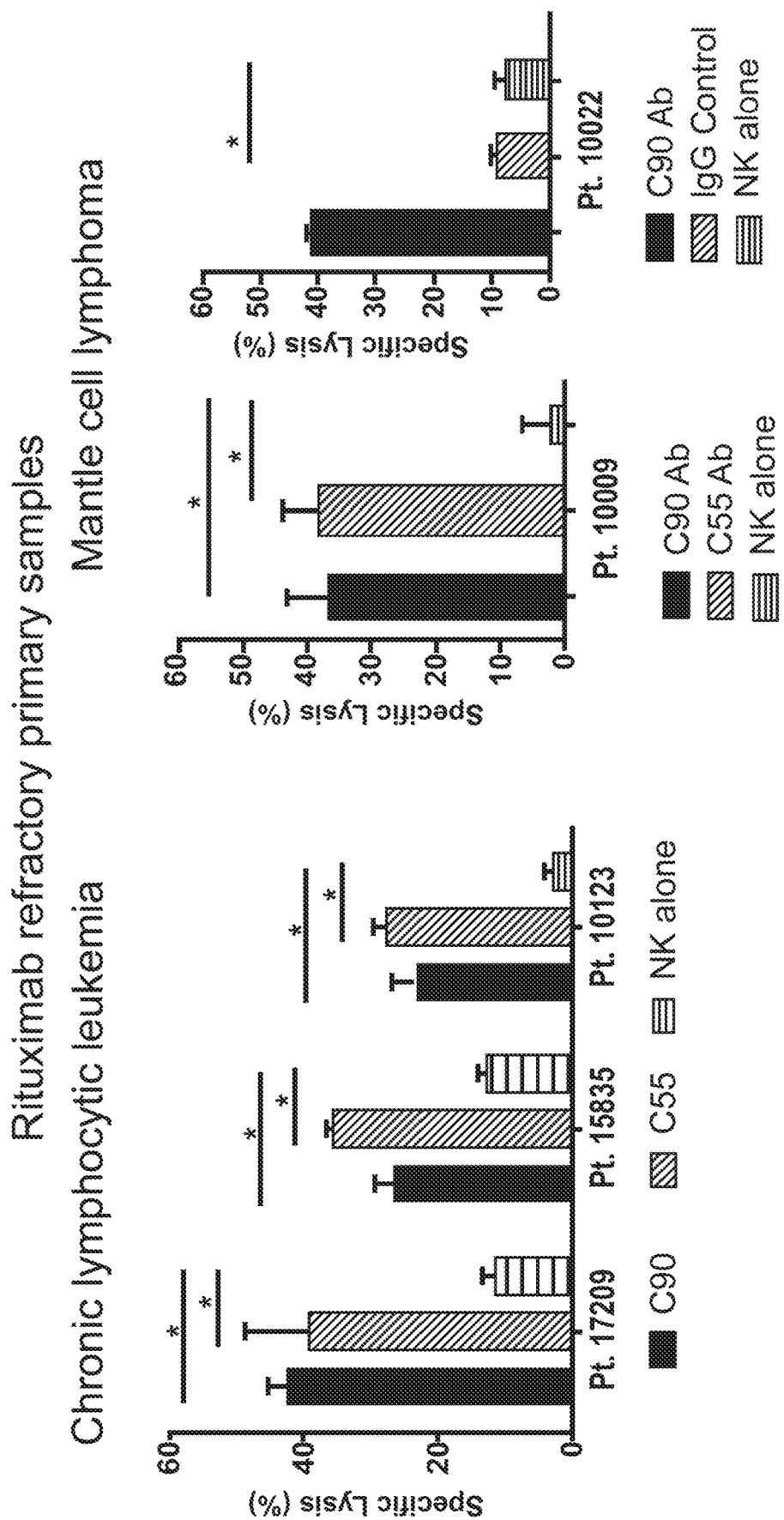

Chimeric mAb induced potent antitumor effects against drug-resistant lymphomas in vitro and in vivo. The antibodies were further tested against primary CLL (n=3) and MCL (n=2) samples from patients who had been previously treated with rituximab. All five primary samples were sensitive to killing by ADCC with C55 and C90, suggesting their effectiveness against tumors which progressed clinically after exposure to rituximab (FIG. 3B).

Figure 5A:
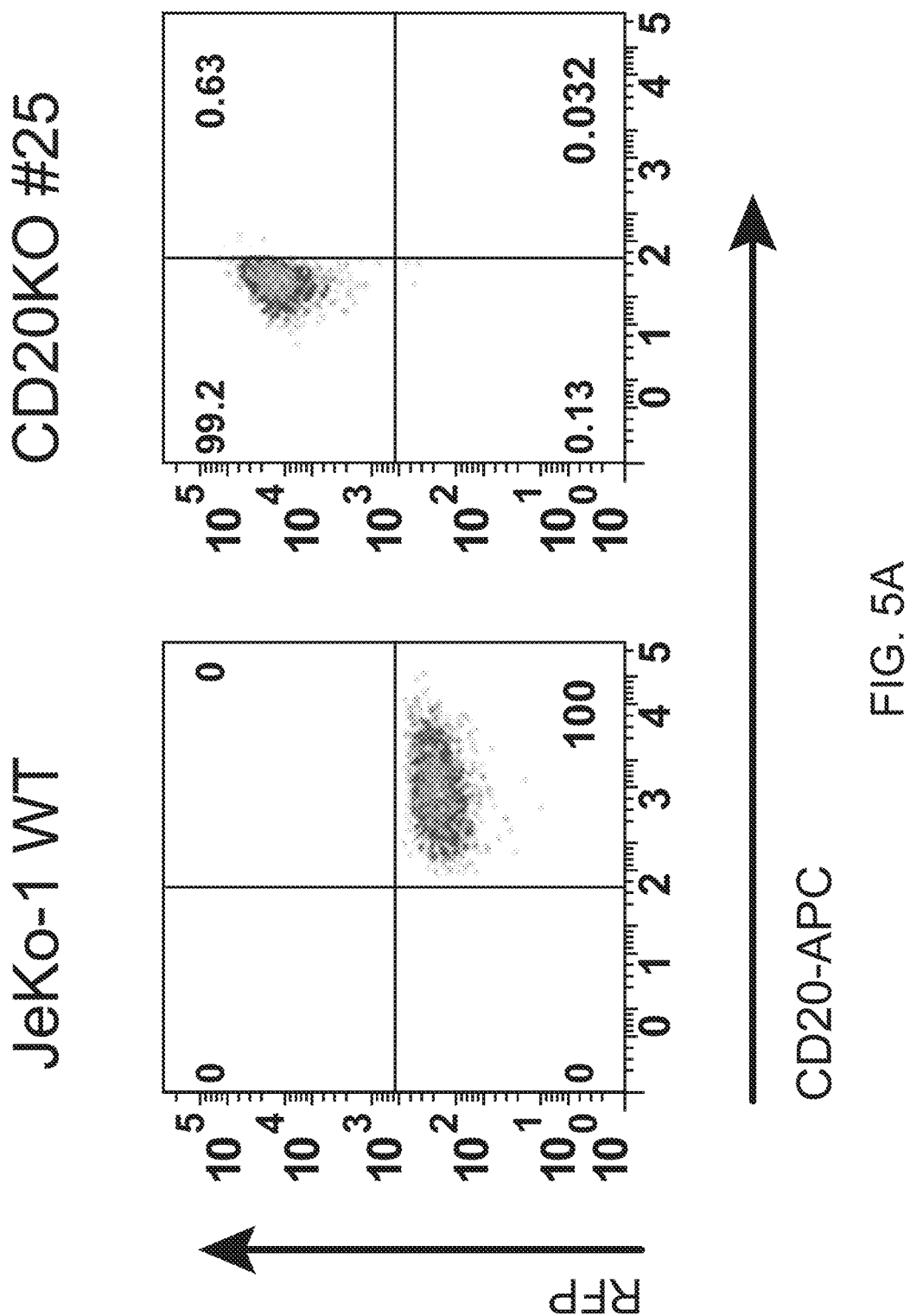
FIGS. 5A, 5B and 5C are images or graphs showing chimeric BAFF-R antibodies induce ADCC on drug resistant lymphoma models in vitro.
Figure 5B:
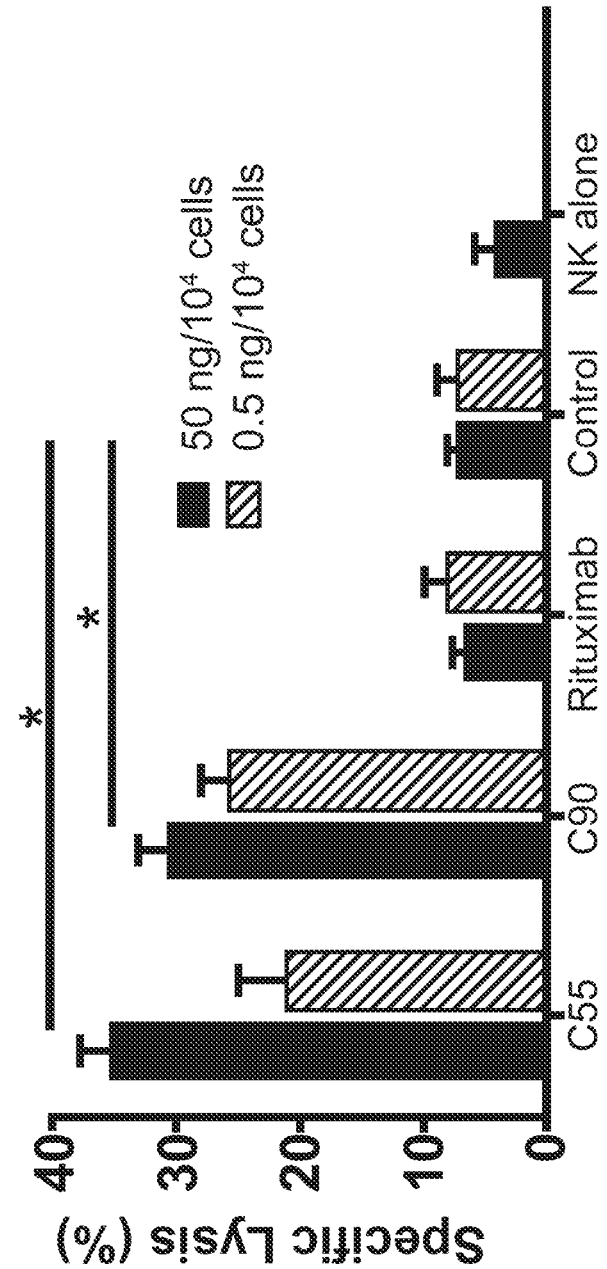

In order to create a model of drug-resistant lymphomas, a stable CD20 knock-out (KO) clone of JeKo-1 was generated using a CRISPR/HDR system. CD20-KO clones were confirmed for absence of CD20 surface expression by flow cytometry and Western blotting (FIG. 5A and FIGS. 16A and 16B) and the presence of BAFF-R surface expression by flow cytometry (FIG. 16C). JeKo-1-CD20-KO clone 25, selected for further studies, retained sensitivity to C55- and C90-mediated ADCC, but became insensitive to cytotoxicity mediated by anti-CD20 rituximab (FIG. 5B).

Figure 5C:
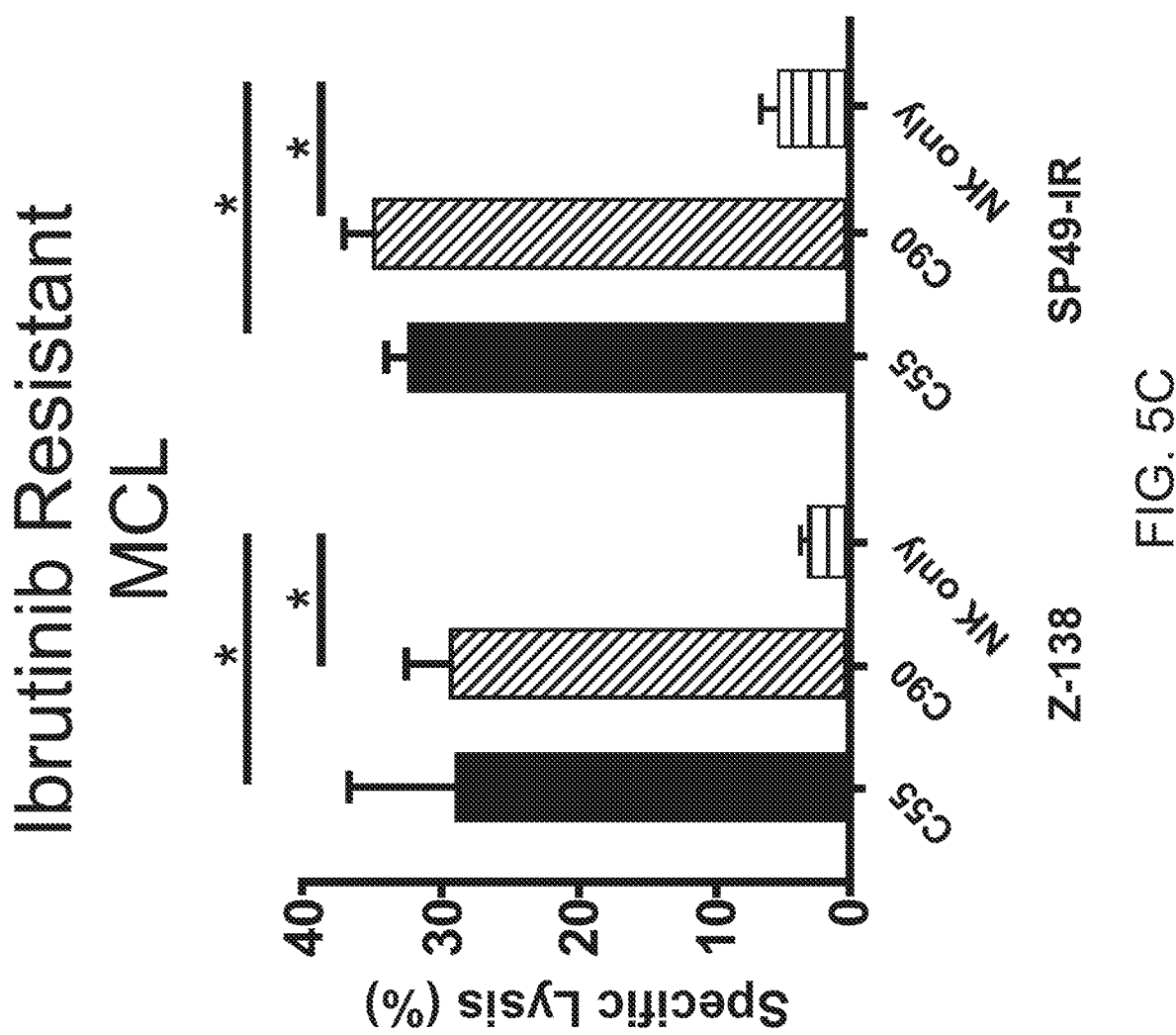

As a second model of drug-resistant lymphomas, the chimeric BAFF-R mAb was tested for ADCC against the naturally ibrutinib resistant human MCL line, Z-138, and the induced ibrutinib resistant MCL line, SP49-IR, which had been induced in vitro for resistance to ibrutinib (see Methods). Significant in vitro ADCC was observed with the antibodies against both ibrutinib resistant lines (FIG. 5C).

Figure 4A:
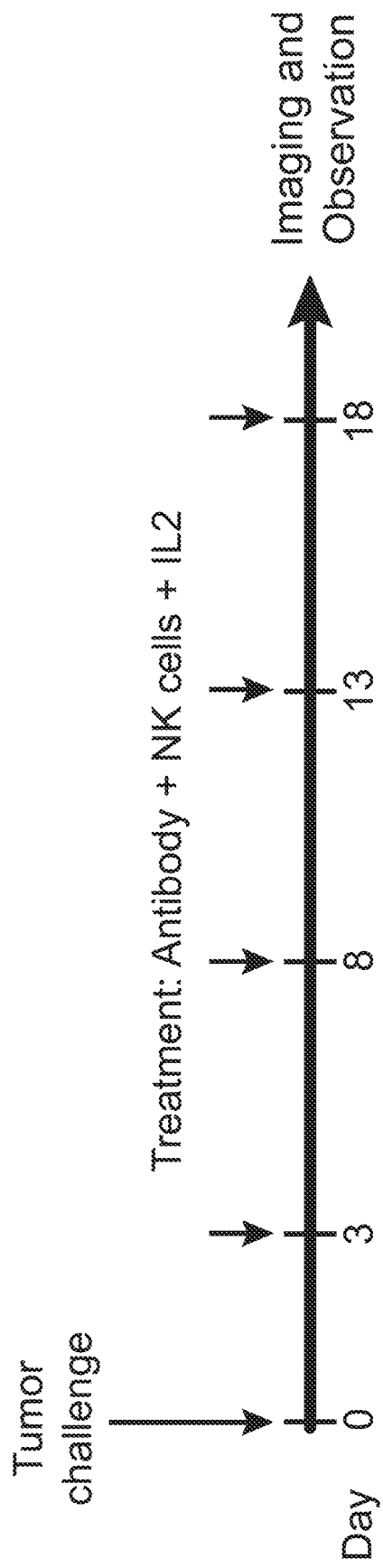
FIG. 4A is a schematic showing treatment schedule following Day 0 tumor challenge with minimum lethal dose of tumors. Treatments were given by IV tail vein injections.
Figure 4B:
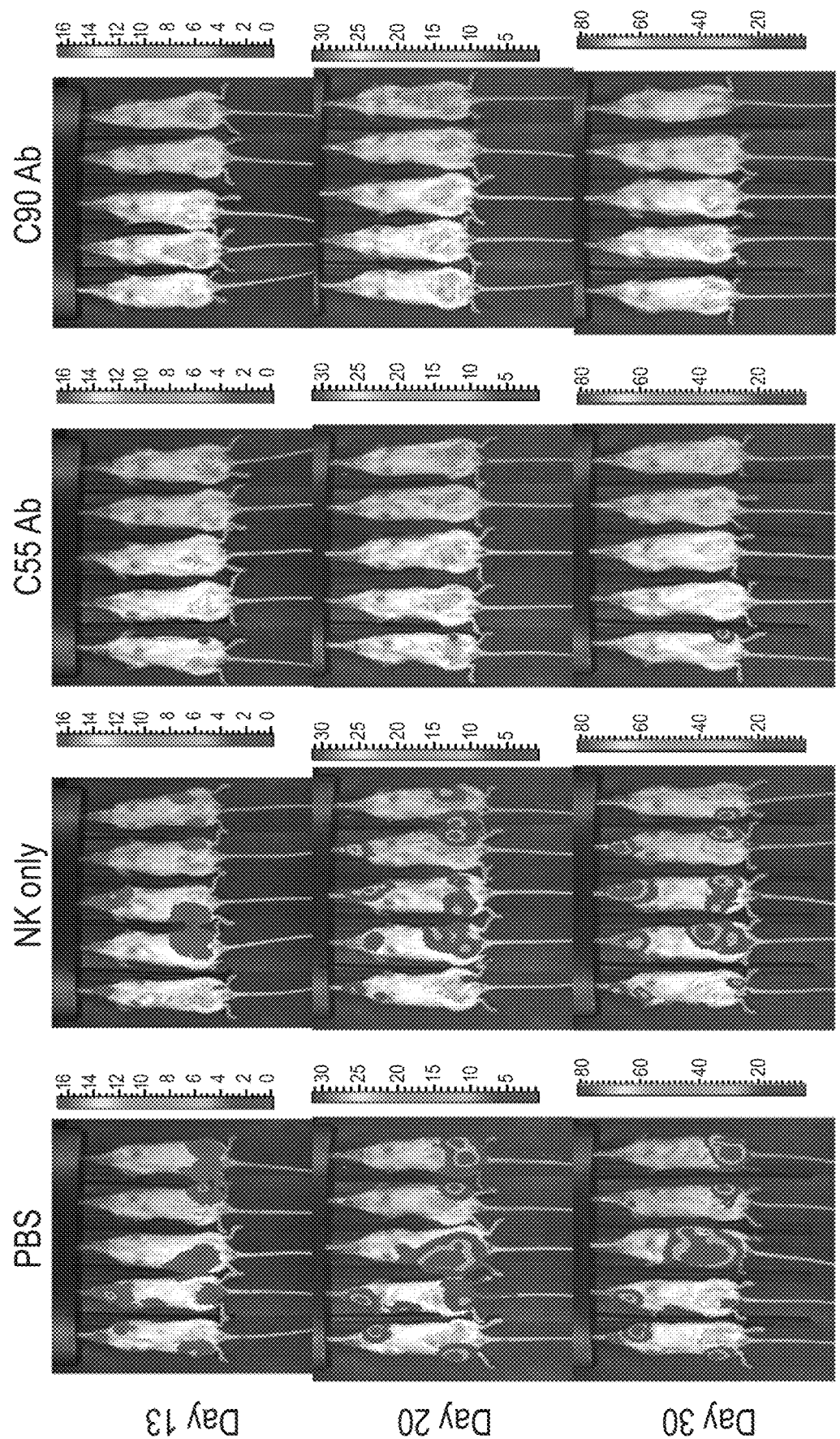
FIGS. 4B and 4C are images showing chimeric antibodies targeting human BAFF-R elicited in vivo therapeutic effects against B-cell tumors. Bioluminescence images of mice challenged with luciferase-expressing tumors: JeKo-1 (MCL) (FIG. 4B) or RS4;11 (ALL) (FIG. 4C). Experimental groups received treatment of chimeric BAFF-R mAbs (C55 or C90, as indicated). Control group mice received PBS, NK cells alone, or rituximab on the same schedule. Data are representative of three independent experiments.
Figure 4C:
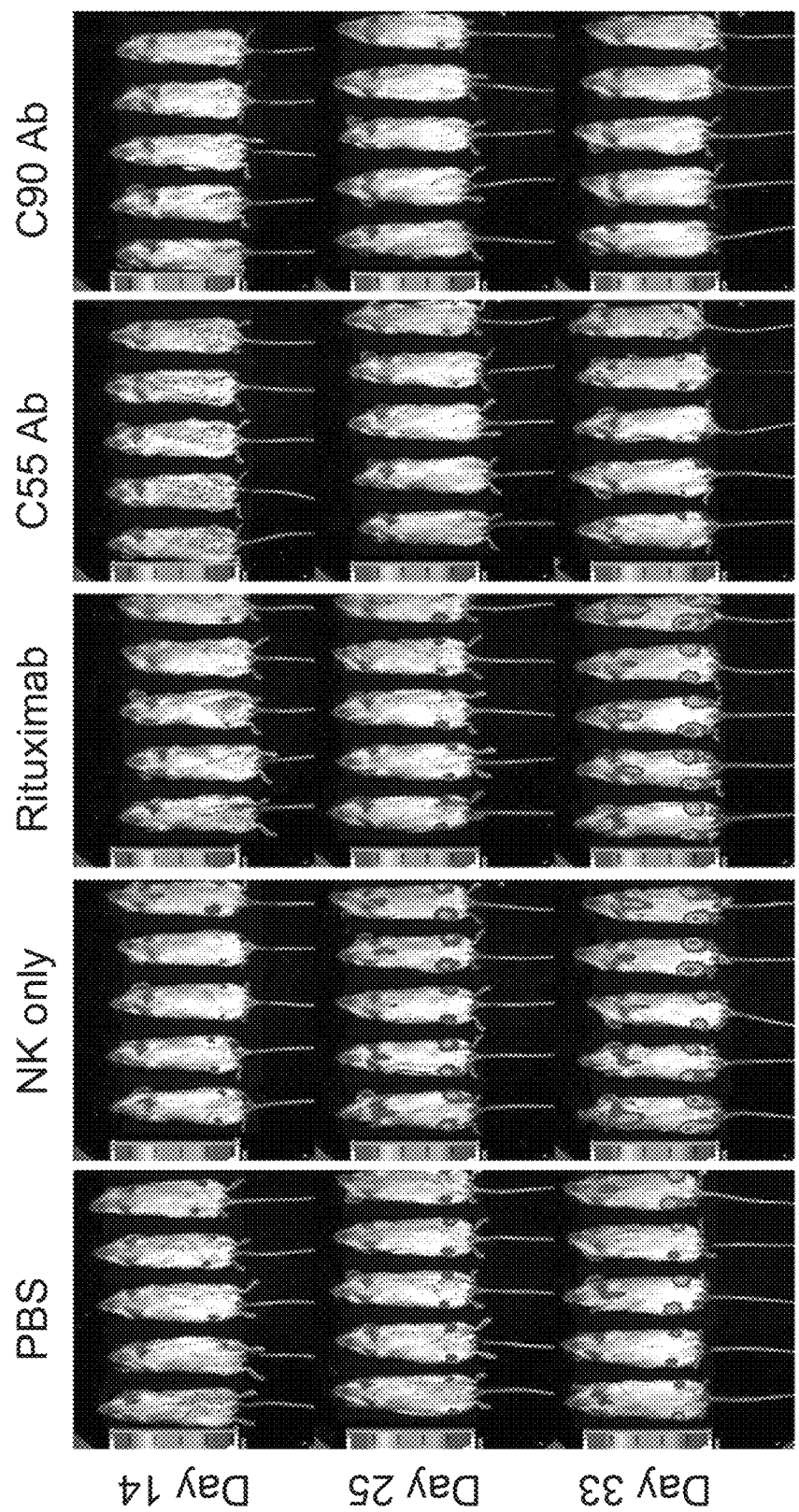
Figure 6A:
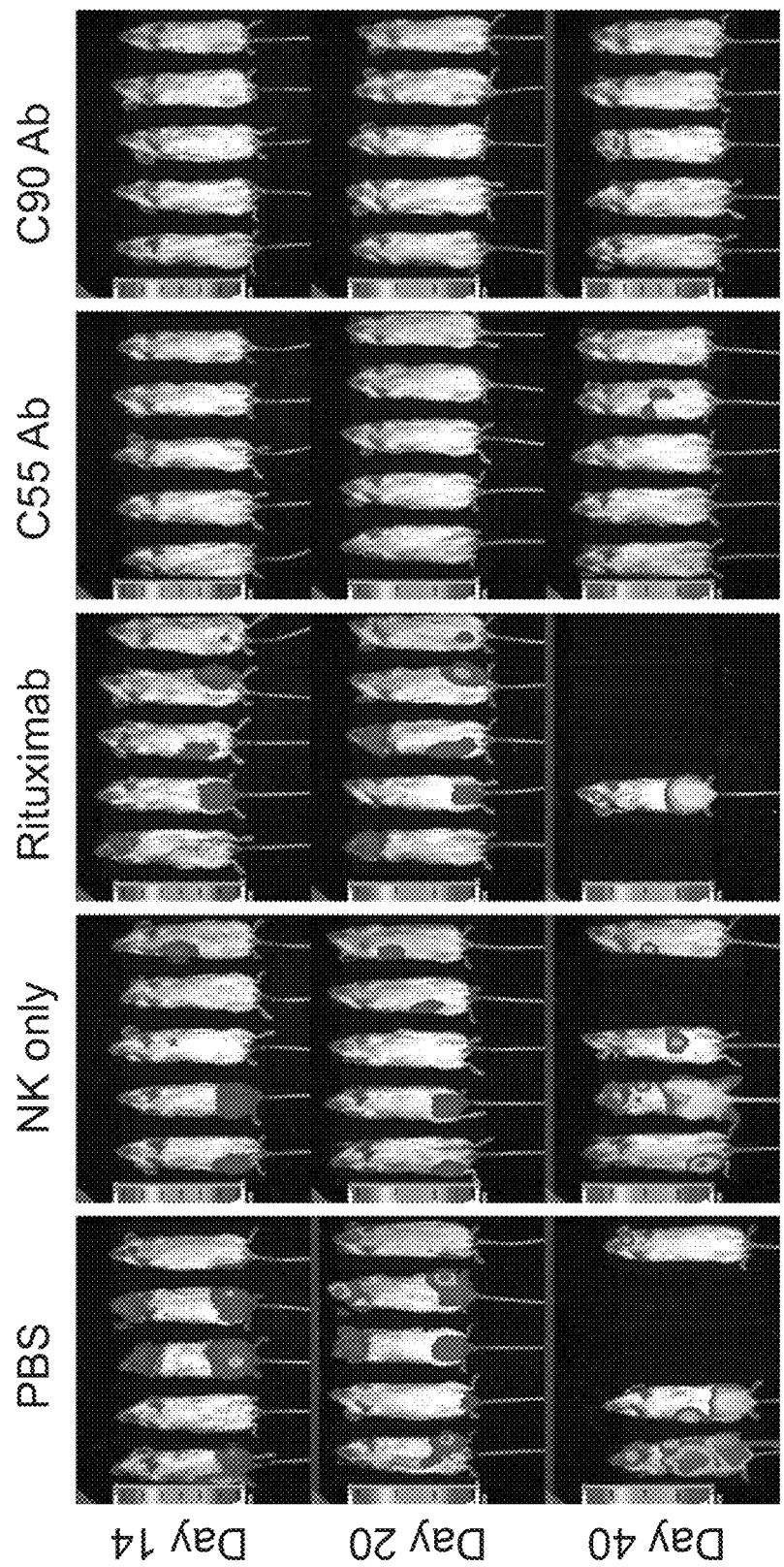
FIGS. 6A and 6B are images and FIG. 6C are graphs showing chimeric antibodies targeting human BAFF-R elicited in vivo therapeutic effects against drug resistant B-cell tumors. Bioluminescence images of mice challenged with luciferase-expressing tumors JeKo-1-CD20-KO cells (FIG. 6A) or ibrutinib-resistant Z-138 cells (FIG. 6B) followed by antibody treatments as in FIG. 4. Control group mice received PBS, NK cells alone, or rituximab on the same schedule.
Figure 6B:
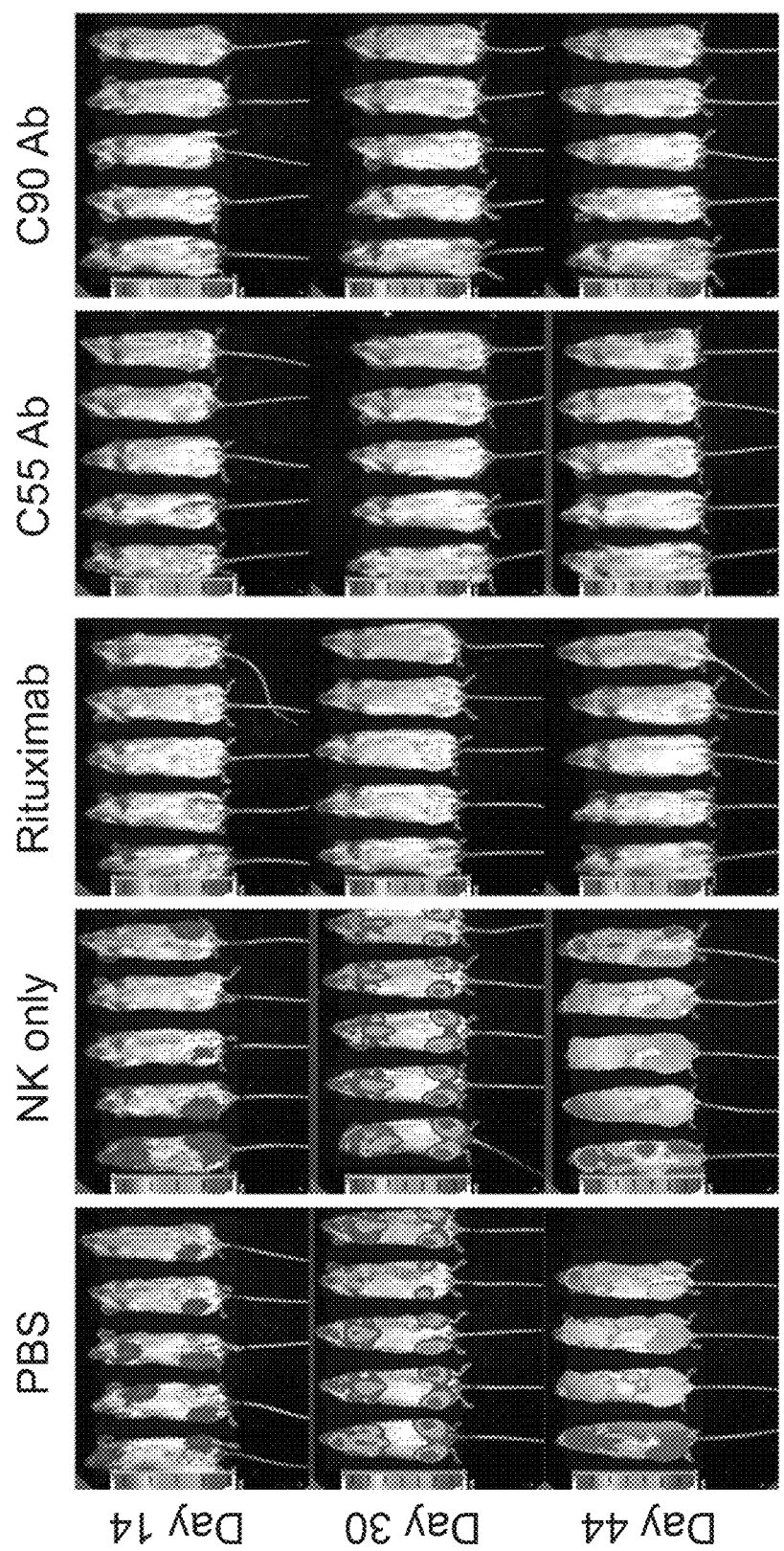
Figure 6C:
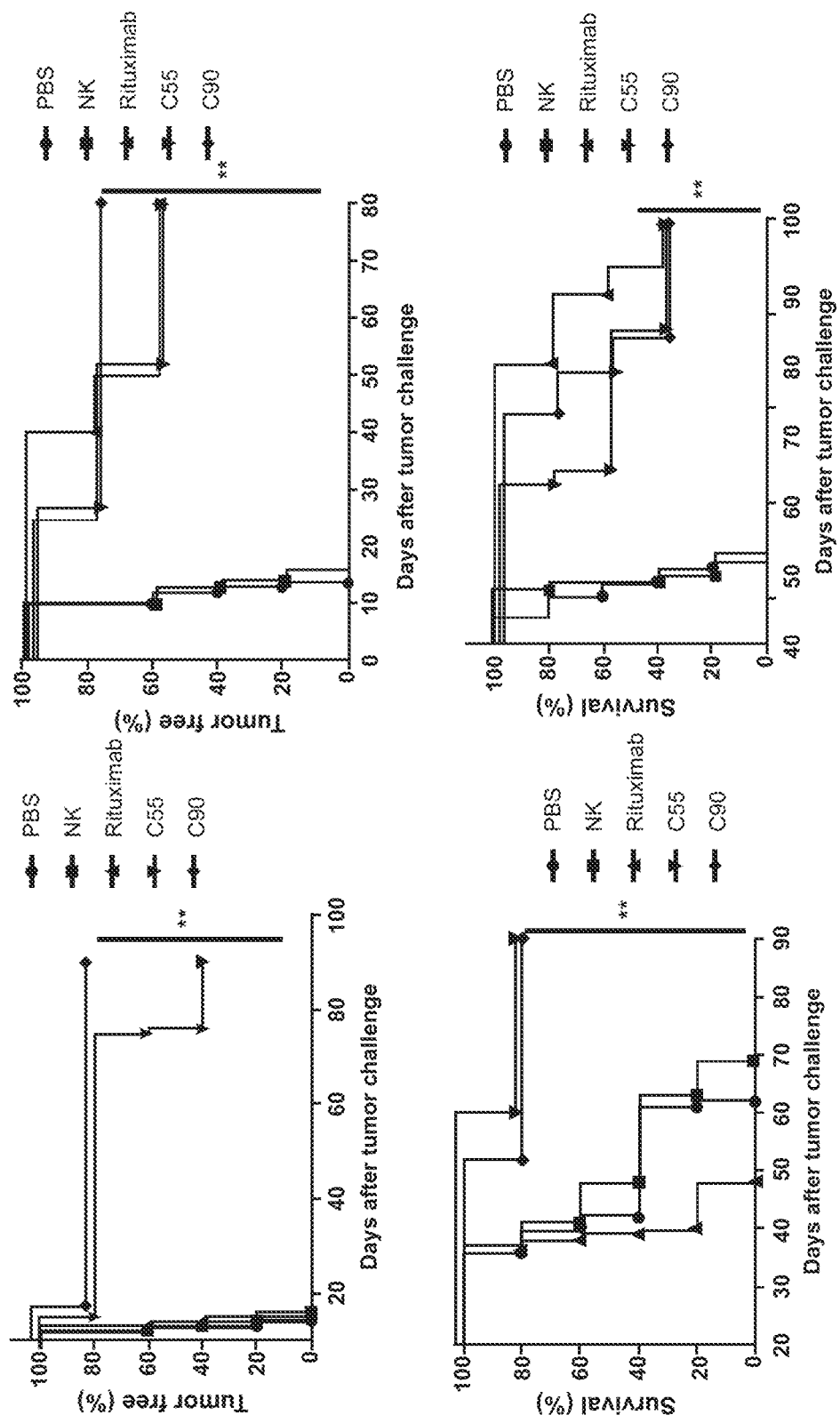

Finally, three days following IV challenge with JeKo-1-CD20-KO tumor cells in vivo, NSG mice (n=5 per group) received BAFF-R antibody treatments (C55 or C90) or rituximab as described in Methods and according to the schedule in FIG. 4A. Bioluminescent imaging on Day 20 revealed substantial tumor burden in controls and rituximab treated mice, but no visible tumors in BAFF-R antibody treatment groups (FIG. 6A). Monitoring tumor free and long-term overall survival confirmed the significant antitumor effects of both BAFF-R antibodies, but not rituximab (FIG. 6C). Similarly, significant effects were observed following treatment of ibrutinib-resistant Z-138 tumor-bearing mice with either BAFF-R antibody, compared with controls (PBS or NK only) (FIG. 6B-C).

BAFF-R mAbs also bind normal B cells. When tested against normal PBMC, anti-BAFF-R antibody C90 exhibited specific binding against B cells, as expected, without staining any T cells, NK cells, granulocytes, or monocytes (FIGS. 17A-17B). The positive staining results were verified on purified B cells (FIG. 18). Again, purified T cells, NK cells, and gated myeloid cells showed no binding.

Expanding our scope, immunohistochemistry studies showed positive staining of our antibodies on tonsil and spleen samples, leaving all other vital organs, including heart, lung, kidney, and brain, untouched (FIGS. 19A and 19B).

Discussion

The provided BAFF-R mAbs elicited robust in vivo antitumor effects as a single agent against multiple B-cell tumor types, including NHL, CLL, and ALL. Furthermore, the antibodies eradicated established tumors, which led to long-term, tumor-free survival in vivo.

The distinctive features of the BAFF-R mAbs may be due to the approach used to generate them. The provided approach was to express human BAFFF-R as a native surface protein on mouse fibroblast cells for immunization, increasing the likelihood of presenting a natively folded, glycosylated immunogen. Therefore, it is very likely that the antibodies are binding an accessible human BAFF-R epitope distinct from the other antibodies described. Thus, a technical strategy was demonstrated for generating monoclonal antibodies against a natively folded, eukaryotically glycosylated human BAFF-R that is able to specifically bind, lyse, and inhibit B-cell tumors in vivo. The results suggest the main anti-tumor mechanism of our mAbs is ADCC, as NK cells were required in addition to mAbs for in vitro activity (FIG. 2); no evidence of CDC was observed. Both antibodies were able to competitively inhibit BAFF ligand binding to BAFF-R (FIG. 14).

One clinically relevant mechanism of resistance to rituximab is down-regulation of CD20. This phenomenon of drug resistance was modeled with a CRISPR edited MCL line, JeKo-1, which is deficient in CD20. The significant in vivo antitumor effects of C55 or C90, but not rituximab treatment, against this line and similarly against the naturally ibrutinib resistant Z-138 MCL suggests efficacy against drug-resistant lymphomas (FIG. 5). Taken together with the in vitro cytotoxicity of these antibodies against primary tumors from lymphoma patients who were previously treated with, and progressed in response to rituximab, these data suggest C55 and C90 as a potential treatment strategy to overcome drug resistance (FIG. 3).

Example 2

Humanizing BAFF-R mAb

The chimeric antibody, clone 90, was humanized while retaining its binding specificity and cytotoxic effects. Through computational analysis of the CDRs and predicted structure, three variants of the heavy and three variants of the light chain were produced with varying degrees of likeness to human antibodies. A total of nine combinational variants was constructed from the humanized heavy and light chains. These variants all proved comparable in binding affinity to the parental chimeric antibody with $K_D$ values ranging from 2.6 to 5.0 nM (Table 1).

TABLE 1

Binding Affinity of Humanized BAFF-R Antibody Variants

| Loading Sample ID | Sample ID | KD (M) | kon(1/Ms) | kdis(1/s) | Full R^2 | Full X^2 |
| --- | --- | --- | --- | --- | --- | --- |
| Chimeric Parental | BAFF-R | 3.0E−09 | 9.9E+05 | 2.0E−03 | 0.0049 | 0.9809 |
| Humanized HC1 + LC1 | BAFF-R | 4.0E−09 | 6.1E+05 | 2.4E−03 | 0.0114 | 0.9619 |
| Humanized HC1 + LC2 | BAFF-R | 3.7E−09 | 6.2E+05 | 2.3E−03 | 0.005 | 0.9800 |
| Humanized HC1 + LC3 | BAFF-R | 5.0E−09 | 4.1E+05 | 2.1E−03 | 0.0125 | 0.9565 |
| Humanized HC2 + LC1 | BAFF-R | 2.6E−09 | 7.7E+05 | 2.0E−03 | 0.0051 | 0.9790 |
| Humanized HC2 + LC2 | BAFF-R | 3.6E−09 | 6.1E+05 | 2.2E−03 | 0.0047 | 0.9799 |
| Humanized HC2 + LC2 | BAFF-R | 3.2E−09 | 8.2E+05 | 3.1E−03 | 0.0045 | 0.9821 |
| Humanized HC3 + LC1 | BAFF-R | 3.8E−09 | 8.2E+05 | 3.1E−03 | 0.0045 | 0.9821 |
| Humanized HC3 + LC2 | BAFF-R | 3.1E−09 | 1.2E+06 | 3.7E−03 | 0.0074 | 0.9793 |
| Humanized HC3 + LC3 | BAFF-R | 3.4E−09 | 6.8E+05 | 2.3E−03 | 0.0025 | 0.9900 |

The nine candidate antibodies were further assessed and a lead candidate was determined. The binding of the humanized antibodies were observed to have specificity to BAFF-R and all had similar relative binding in a dose dependent manner (FIG. 20A). Additionally, the humanized antibodies were assessed for their ADCC effects. Again, it was found that the humanized candidates maintained their specific cytotoxicity, and performed equally well compared to the chimeric controls and rituximab (FIG. 20B).

Humanized clone 90 variants 4 and 5 were selected for further in vitro testing. The humanized antibody variants were biotinylated and visualized with a fluorescent streptavidin probe. Their binding against various non-Hodgkin's lymphoma, lymphoblastic leukemia, and multiple myeloma lines were assessed, including JeKo-1, Ly-10, MEC-2, RL, RS4, Raji, Z138, and U266 (FIG. 22A). The flow cytometry results reveal a significant binding to each of these cell lines. Further flow analysis with the humanized variants against normal PBMCs show specificity in the binding. When assessed for the binding of granulocytes, monocytes, B cells, T cells, and NK cells in normal healthy PBMCs, the antibodies only bind the B cells population (FIG. 22B).

The two variants were further assessed in their ability to initiate ADCC. The antibodies were administered in varying concentration to JeKo-1, Z138, and RS4 lines after a period of chromium uptake. The cells and antibodies were incubated with effector NK cells. The supernatant was analyzed 6 hours post treatment (FIG. 21A). The antibodies have a clear cytotoxic effect against tumor lines and demonstrate a dose dependency with each 10 fold dilution. The results are comparable to that of rituximab but can also be seen in RS4 acute lymphoblastic lymphoma, where rituximab is not active. Further assays with LY-10, MEC-2, RL, and Raji (FIG. 21B) continue to demonstrate the potency of the humanized antibody treatment. All results found were comparable to that of the current conventional treatment with rituximab.

Example 3

Chimeric Antigen Receptor T Cell

Antibodies with high binding affinity and bioactivity were used to construct chimeric antigen receptor (CAR) T cells for in vivo studies. DNA sequences for heavy and light chain variable domains were arranged into a single chain (sFv) format and engineered to a T cell signaling domain (δchain) along with a 4-1BB motif. The engineered CAR gene was introduced into purified healthy donor derived CD8+ T cells along with a co-expressing GFP via a lentivirus. CAR-T cells were cell sorted for their expression of GFP and expanded in vitro with CD3 and CD28 beads for animal studies. NSG mice were challenged with a luciferase expressing JeKo-1 MCL line (JeKo-1-luci). The tumor was allowed to develop and monitored by bioluminescent imaging until a visible population of tumor cells were observed; approximate 9 days post tumor challenge. Mice were administered two dose of 5×10$^6$ CAR-T cells (anti-BAFF-R and anti-CD19) on days 9 and 15 post tumor challenge. Control groups received untreated T cells or saline (PBS). Mice were monitored closely and imaged every 3 days to track the tumor development in order to evaluate the therapeutic anti-tumor effects of CAR-T therapy.

Humanized anti-BAFF-R mAbs were further assessed against primary patient tumor samples for their binding and cytotoxicity. Three mantel cell lymphoma patient samples were characterized with a majority of the tumor cells expressing BAFF-R. Flow cytometry results reveal distinct populations of these primary tumor cells that were bound by our humanized antibodies (FIG. 22A). Furthermore, chromium release cytotoxicity assays on the same primary tumor samples revealed high specific killing compared to controls. The results were comparable to the effects of rituximab and consistent with the chimeric antibodies developed earlier (FIG. 22B). The cell type specificity of the humanized antibodies was determined by assessing their binding to normal PBMC. No appreciable binding was noted for the major groups of PBMCs including granulocytes, monocytes, T cells and NK cells. The B cell population was the only detectable population that was bound by the antibody (FIG. 23). The results of the assay is also consistent with the previously characterized chimeric antibodies.

The anti-BAFF-R mAbs were further used to create chimeric antigen receptor (CAR) T cells. Experiments utilized the chimeric C55 variable region engineered into a single chain (sFv) format. The anti-BAFF-R C55 sFv was attached to a T cell receptor signaling domain containing a 4-1BB motif and successfully introduced into healthy normal human donor CD8+ T cells isolated form PBMC. The CAR-T cells were administered to tumor bearing mice with an appreciable tumor burden (FIG. 24). Mice treated with the anti-BAFF-R CAR-T cells had significant tumor clearance when compared to either saline or non-engineered T cell control groups. Additionally, the anti-tumor effects of our CAR-T cells are comparable to those of the anti-CD-19 CAR-T treated group.

The chimeric anti-BAFF-R antibody C90 was humanized with several variants. The humanization process took into consideration and analysis of the variable region and specifically the CDRs of the chimeric antibody. From there, three variants for each heavy and light chain was developed with varying degrees of human-likeness ranging from 1 the most human to 3 the most conservative to the chimeric. The variants were combined to produce 9 variants. Biacore analysis was performed on each variant as well as the chimeric parental C90 to determine their equilibrium dissociation constant $K_D$. The antigen was commercial, recombinant extracellular domain of human BAFF-R.

What is claimed is:

1. A pharmaceutical composition comprising a pharmaceutically acceptable excipient and a therapeutically effective amount of a B cell activating factor receptor (BAFF-R) antibody comprising a light chain variable region and a heavy chain variable region,
wherein said light chain variable region comprises:
a CDR L1 as set forth in SEQ ID NO:1, a CDR L2 as set forth in SEQ ID NO:2 and a CDR L3 as set forth in SEQ ID NO:3; and
wherein said heavy chain variable region comprises:
a CDR H1 as set forth in SEQ ID NO:4, a CDR H2 as set forth in SEQ ID NO:5, and a CDR H3 as set forth in SEQ ID NO:6.

2. The pharmaceutical composition of claim 1, wherein said antibody is a humanized antibody.

3. The pharmaceutical composition of claim 1, wherein said light chain variable region comprises the sequence of SEQ ID NO:18, SEQ ID NO:20 or SEQ ID NO:22.

4. The pharmaceutical composition of claim 1, wherein said heavy chain variable region comprises the sequence of SEQ ID NO:24, SEQ ID NO:26 or SEQ ID NO:28.

5. The pharmaceutical composition of claim 1, wherein said antibody is a chimeric antibody.

6. The pharmaceutical composition of claim 1, wherein said light chain variable region comprises the sequence of SEQ ID NO:14.

7. The pharmaceutical composition of claim 1, wherein said heavy chain variable region comprises the sequence of SEQ ID NO:16.

8. The pharmaceutical composition of claim 1, wherein the antibody is an IgG.

9. The pharmaceutical composition of claim 1, wherein said antibody is a Fab' fragment.

10. The pharmaceutical composition of claim 1, wherein said antibody is a single chain antibody (scFv).

11. The pharmaceutical composition of claim 1, wherein said antibody is capable of binding a BAFF-R protein with an equilibrium dissociation constant ($K_D$) of less than about 5 nM.

12. The pharmaceutical composition of claim 1, wherein said antibody is capable of binding a BAFF-R protein with an equilibrium dissociation constant ($K_D$) of less than about 4 nM.

13. The pharmaceutical composition of claim 1, wherein said antibody is bound to a BAFF-R protein.

14. The pharmaceutical composition of claim 13, wherein said BAFF-R protein is a human BAFF-R protein.

15. The pharmaceutical composition of claim 13, wherein said BAFF-R protein forms part of a cell.

16. The pharmaceutical composition of claim 13, wherein said BAFF-R protein is expressed on the surface of a cell.

17. The pharmaceutical composition of claim 16, wherein said cell is a lymphoid cell.

18. The pharmaceutical composition of claim 16, wherein said cell is a B cell.

19. The pharmaceutical composition of claim 16, wherein said cell is a cancer cell.

20. The pharmaceutical composition of claim 19, wherein said cancer cell is a lymphoma cell.

* * * * *